United States Patent
Hutchens et al.

(10) Patent No.: US 7,329,484 B2
(45) Date of Patent: Feb. 12, 2008

(54) RETENTATE CHROMATOGRAPHY AND PROTEIN CHIP ARRAYS WITH APPLICATIONS IN BIOLOGY AND MEDICINE

(75) Inventors: T. William Hutchens, Mountain View, CA (US); Tai-Tung Yip, Cupertino, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 495 days.

(21) Appl. No.: 10/626,302

(22) Filed: Jul. 23, 2003

(65) Prior Publication Data

US 2005/0233306 A1    Oct. 20, 2005

Related U.S. Application Data

(60) Continuation of application No. 10/150,472, filed on May 17, 2002, now abandoned, which is a division of application No. 09/745,388, filed on Dec. 21, 2000, now Pat. No. 6,844,165, which is a division of application No. 09/100,302, filed on Jun. 19, 1998, now Pat. No. 6,225,047.

(60) Provisional application No. 60/067,484, filed on Dec. 1, 1997, provisional application No. 60/054,333, filed on Jun. 20, 1997.

(51) Int. Cl.
    *G01N 33/543* (2006.01)

(52) U.S. Cl. .......... 435/4; 436/518; 436/524; 436/528; 436/529; 436/531; 436/532; 436/173

(58) Field of Classification Search .......... None
    See application file for complete search history.

(56) References Cited

U.S. PATENT DOCUMENTS 4,126,554 A    11/1978   Rainin (Continued)

FOREIGN PATENT DOCUMENTS

GB    2 281 122 A    2/1995

(Continued)

OTHER PUBLICATIONS

Dogruel, D. et al. Rapid Tryptic Mapping Using Enzymatically Active Mass Spectrometer Probe Tips. Anal. Chem. 67: 4343-4348 (1995).

(Continued)

*Primary Examiner*—Christopher L. Chin
(74) *Attorney, Agent, or Firm*—Townsend and Townsend and Crew LLP

(57) ABSTRACT

This invention provides methods of retentate chromatography for resolving analytes in a sample. The methods involve adsorbing the analytes to a substrate under a plurality of different selectivity conditions, and detecting the analytes retained on the substrate by desorption spectrometry The methods are useful in biology and medicine, including clinical diagnostics and drug discovery.

23 Claims, 44 Drawing Sheets

U.S. PATENT DOCUMENTS

| | | | |
|---|---|---|---|
| 4,313,906 A | 2/1982 | Filipi et al. | |
| 4,752,562 A | 6/1988 | Sheiman et al. | |
| 4,963,263 A | 10/1990 | Kauvar | 210/635 |
| 5,010,175 A | 4/1991 | Rutter et al. | 435/69.7 |
| 5,045,694 A | 9/1991 | Beavis et al. | 250/287 |
| 5,118,937 A | 6/1992 | Hillenkamp et al. | 250/282 |
| 5,133,866 A | 7/1992 | Kauvar | 210/635 |
| 5,135,627 A | 8/1992 | Soane | |
| 5,223,409 A | 6/1993 | Ladner et al. | 435/69.7 |
| 5,288,644 A | 2/1994 | Beavis et al. | 436/94 |
| 5,338,659 A | 8/1994 | Kauvar | 435/7.1 |
| 5,340,474 A | 8/1994 | Kauvar | 210/198.2 |
| 5,356,784 A | 10/1994 | Kauvar | 435/7.9 |
| 5,376,249 A | 12/1994 | Afeyan et al. | 204/180.1 |
| 5,445,934 A | 8/1995 | Fodor et al. | 435/6 |
| 5,453,199 A | 9/1995 | Afeyan et al. | |
| 5,498,545 A | 3/1996 | Vestal | |
| 5,538,897 A | 7/1996 | Yates, III et al. | |
| 5,541,070 A | 7/1996 | Kauvar | 435/7.9 |
| 5,547,835 A | 8/1996 | Koster | 435/6 |
| 5,571,698 A | 11/1996 | Ladner et al. | 435/69.7 |
| 5,587,293 A | 12/1996 | Kauvar et al. | 435/7.21 |
| 5,599,901 A | 2/1997 | Kauvar | 530/328 |
| 5,605,798 A | 2/1997 | Koster | 435/6 |
| 5,622,824 A | 4/1997 | Koster | 435/6 |
| 5,719,060 A | 2/1998 | Hutchens et al. | 436/174 |

FOREIGN PATENT DOCUMENTS

| | | |
|---|---|---|
| WO | WO 89/03430 | 4/1989 |
| WO | WO 89/09088 | 10/1989 |
| WO | WO 89/10977 | 11/1989 |
| WO | WO 91/18980 | 12/1991 |
| WO | WO 91/19818 | 12/1991 |
| WO | WO 92/18619 | 10/1992 |
| WO | WO 94/06920 | 3/1994 |
| WO | WO 94/28418 | 12/1994 |
| WO | WO 95/00530 | 1/1995 |
| WO | WO 95/35505 | 12/1995 |
| WO | WO 96/36986 | 11/1996 |
| WO | WO 96/37777 | 11/1996 |
| WO | WO 96/40888 | 12/1996 |
| WO | WO 97/06068 | 3/1997 |
| WO | WO 97/10365 | 3/1997 |

OTHER PUBLICATIONS

Krone, J. et al. BIA/MS: Interfacing Biomolecular Interaction Analysis with Mass Spectrometry. Anal. Biochem. 244: 124-132 (1997).

Krone, J. et al. Mass Spectrometric Immunoassay, in: Ultrasensitive Biochemical Diagnostics, Cohn G.E. et al. (Eds.), Proc. SPIE, 2680: 415-421 (1996).

Nelson, R.W. et al. Mass Spectrometric Immunoassay. Anal. Chem. 67: 1153-1158 (1995).

Nelson, R.W. et al. Peptide Chacterization Using Bioreactive Mass Spectrometer Probe Tips. Rapid Commun. Mass Spectrom. 9: 1380-1385 (1995).

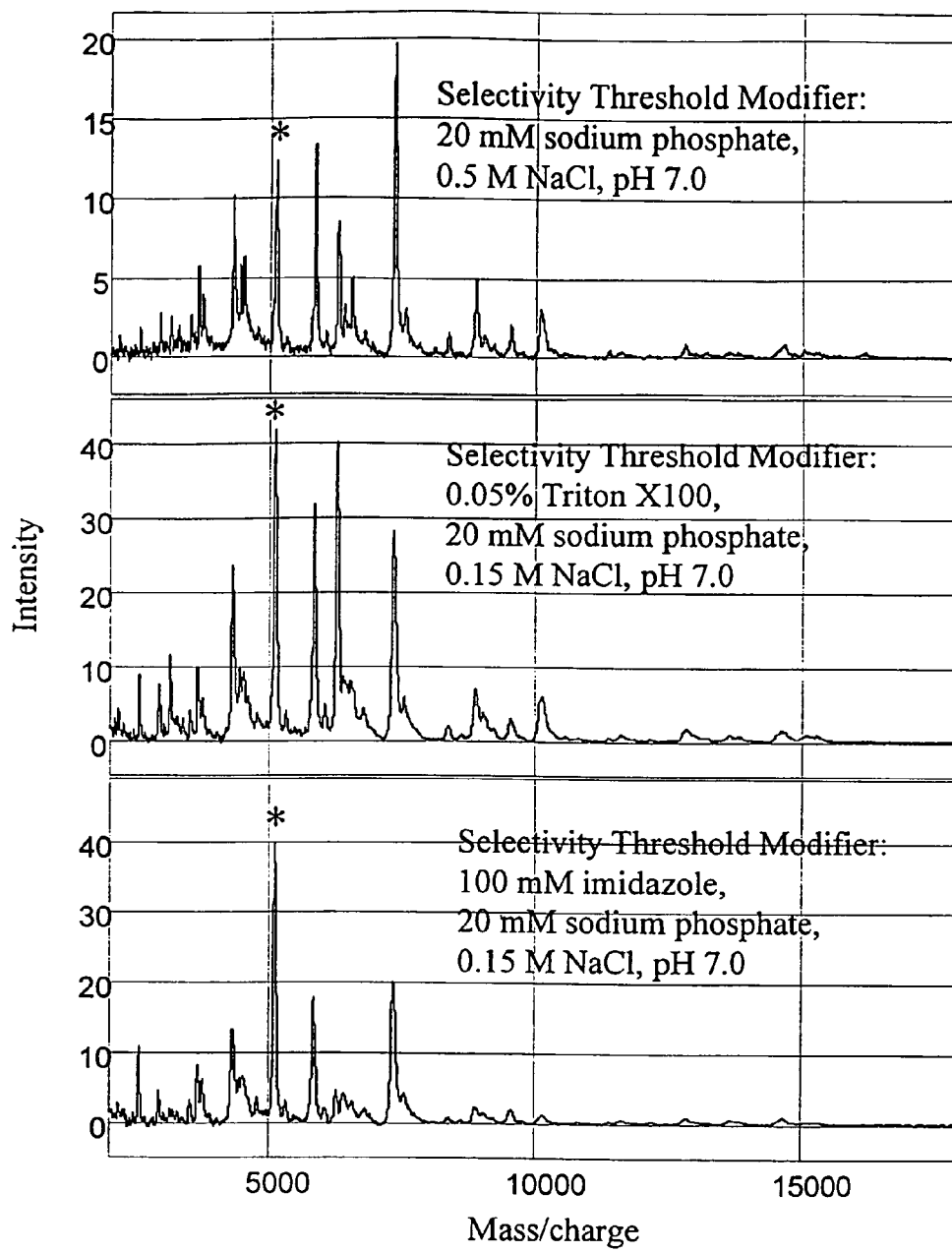

| Sample | Protein | Area | Intensity |
|---|---|---|---|
| Disease | Int std | 1139.044 | 3.340518 |
|  | marker | 695.4804 | 0.580081 |
| Drug treated | Int std | 1383.883 | 3.780178 |
|  | marker | 71.05119 | 0.143227 |

Normalized marker peak area (marker/internal std):
Control        0.0
Disease        0.61
Drug treated   0.05

Retentate Map™ of Human Urine
SELDI ProteinChip™ Array

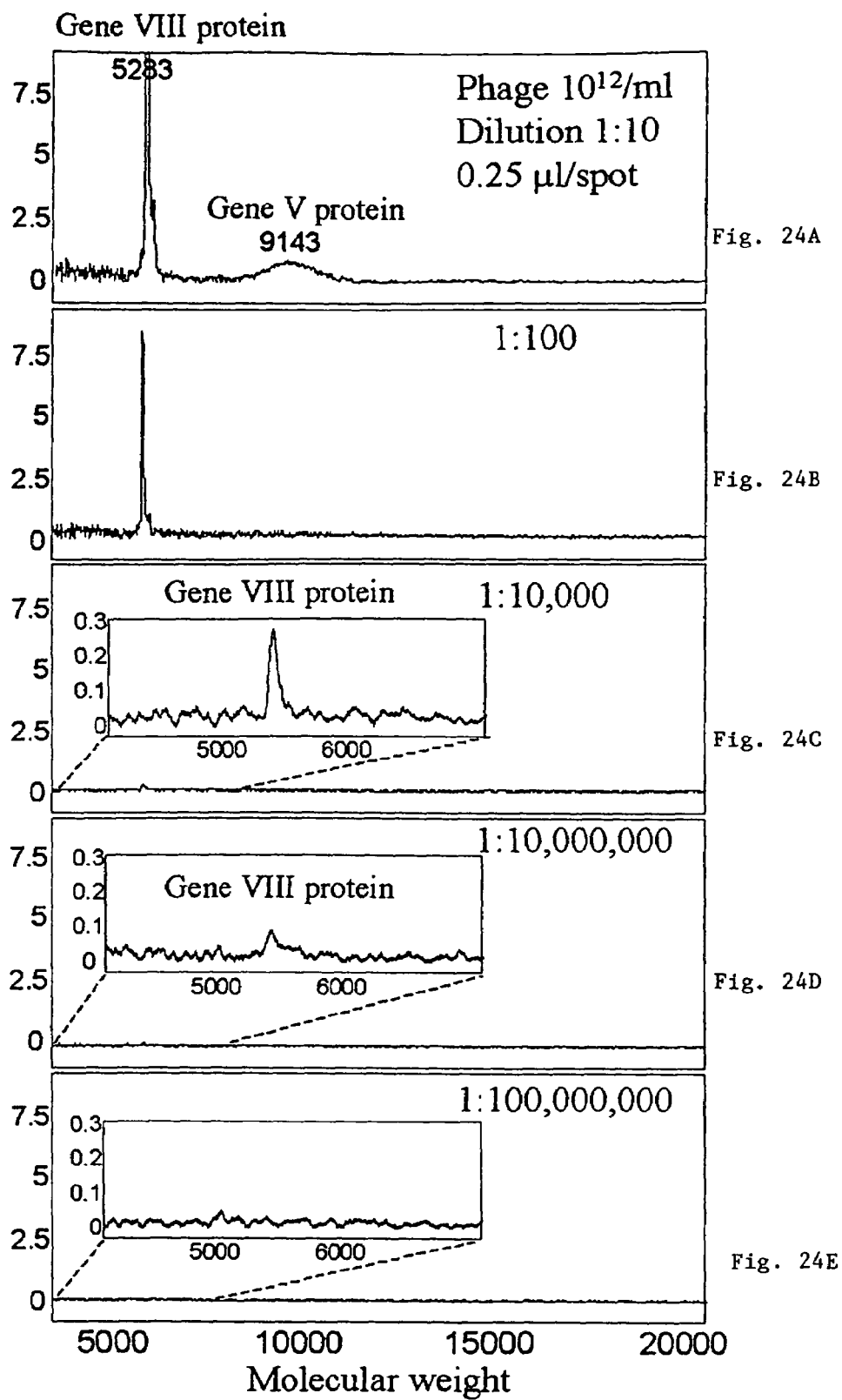

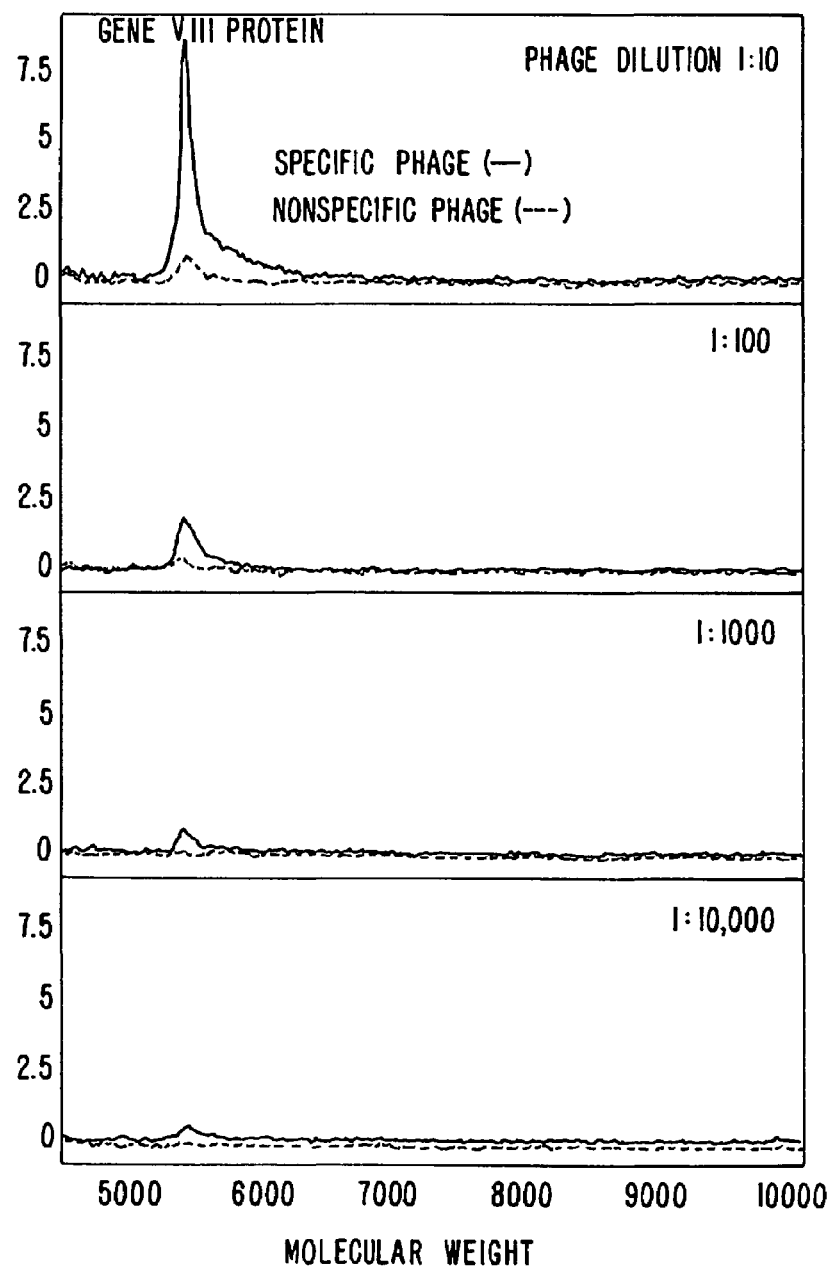

BINDING IN THE ABSENCE OF FREE RECEPTOR (—)
BINDING IN THE PRESENCE OF EXCESS FREE RECEPTOR (----)

MOLECULAR WEIGHT

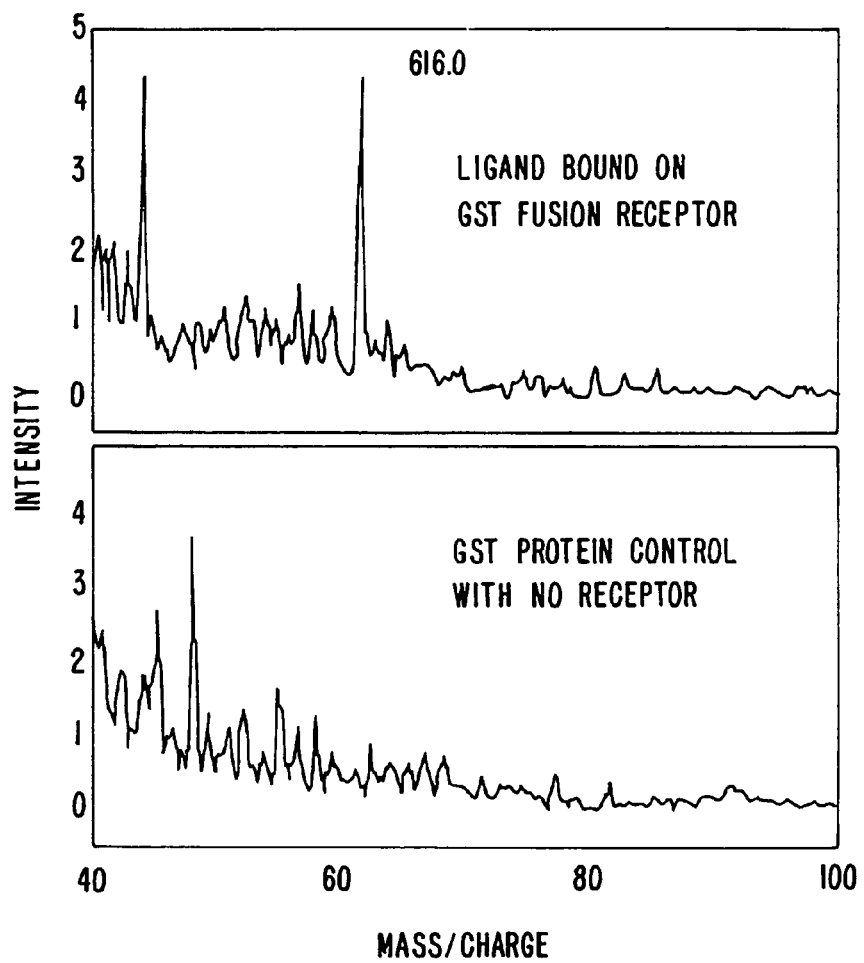

RETENTATE CHROMATOGRAPHY AND PROTEIN CHIP ARRAYS WITH APPLICATIONS IN BIOLOGY AND MEDICINE

CROSS-REFERENCE TO RELATED APPLICATION

This application claims the benefit of the priority dates of co-pending application 60/054,333 filed Jun. 20, 1997 and co-pending application 60/067,484 filed Dec. 1, 1997, the contents of which are incorporated herein by reference in their entirety.

FEDERALLY SPONSORED RESEARCH OR DEVELOPMENT

Not applicable.

BACKGROUND OF THE INVENTION

This invention relates to the field of separation science and analytical biochemistry.

The methods of this invention have applications in biology and medicine, including analysis of gene function, differential gene expression, protein discovery, cellular and clinical diagnostics and drug screening.

Cell function, both normal and pathologic, depends, in part, on the genes expressed by the cell (i.e., gene function). Gene expression has both qualitative and quantitative aspects. That is, cells may differ both in terms of the particular genes expressed and in terms of relative level of expression of the same gene. Differential gene expression can be manifested, for example, by differences in the expression of proteins encoded by the gene, or in post-translational modifications of expressed proteins. For example, proteins can be decorated with carbohydrates or phosphate groups, or they can be processed through peptide cleavage. Thus, at the biochemical level, a cell represents a complex mixture of organic biomolecules.

One goal of functional genomics ("proteomics") is the identification and characterization of organic biomolecules that are differentially expressed between cell types. By comparing expression one can identify molecules that may be responsible for a particular pathologic activity of a cell. For example, identifying a protein that is expressed in cancer cells but not in normal cells is useful for diagnosis and, ultimately, for drug discovery and treatment of the pathology. Upon completion of the Human Genome Project, all the human genes will have been cloned, sequenced and organized in databases. In this "post-genome" world, the ability to identify differentially expressed proteins will lead, in turn, to the identification of the genes that encode them. Thus, the power of genetics can be brought to bear on problems of cell function.

Differential chemical analyses of gene expression and function require tools that can resolve the complex mixture of molecules in a cell, quantify them and identify them, even when present in trace amounts. However, the current tools of analytical chemistry for this purpose are limited in each of these areas. One popular biomolecular separation method is gel electrophoresis. Frequently, a first separation of proteins by isoelectric focusing in a gel is coupled with a second separation by sodium dodecyl sulfate-polyacrylamide gel electrophoresis (SDS-PAGE). The result is a map that resolves proteins according to the dimensions of isoelectric point (net charge) and size (i.e., mass). However useful, this method is limited in several ways. First, the method provides information only about two characteristics of a biomolecule—mass and isoelectric point ("pI"). Second, the resolution power in each of the dimensions is limited by the resolving power of the gel. For example, molecules whose mass differ by less than about 5% or less than about 0.5 pI are often difficult to resolve. Third, gels have limited loading capacity, and thus sensitivity; one may not be able to detect biomolecules that are expressed in small quantities. Fourth, small proteins and peptides with a molecular mass below about 10-20 kDa are not observed.

Other analytical methods may overcome one or more of these limitations, but they are difficult to combine efficiently. For example, analytical chromatography can separate biomolecules based on a variety of analyte/adsorbent interactions, but multi-dimensional analysis is difficult and time consuming. Furthermore, the methods are limited in sensitivity.

Clinical diagnostics requires the ability to specifically detect known markers of disease. However, the development of such diagnostics is hampered by the time necessary to prepare reagents that specifically bind to markers, or that can discriminate the marker in a complex mixture.

Drug discovery requires the ability to rapidly screen agents that modulate ligand/receptor interactions. Often the rate-limiting step in such screens is the ability to detect the ligand/receptor interaction. Thus, rapid and specific methods for identifying binding events would be an advance in the art.

Until now, the process from identifying a potential marker or member of a ligand/receptor pair to producing an agent that specifically binds the marker or member has been difficult. In one method, normal and diseased tissue are compared to identify mRNA species or expressed sequence tags ("ESTs") that are elevated or decreased in the diseased tissue. These species are isolated and the polypeptides they encode are produced through routine methods of recombinant DNA. Then, the polypeptides are isolated and used as immunogens to raise antibodies specific for the marker. The antibodies can be used in, for example, ELISA assays to determine the amount of the marker in a patient sample.

This process is long and tedious. It can take nine months to a year to produce such antibodies, with much of the time being spent on developing protocols to isolate a sufficient quantity of the polypeptide for immunization. Furthermore, the method relies on the hope that differences in RNA expression are expressed as differences in protein expression. However, this assumption is not always reliable. Therefore, methods in which differentially expressed proteins are detected directly and in which specific ligands could be generated in significantly shorter time would be of great benefit to the field.

Thus, tools for resolving complex mixtures of organic biomolecules, identifying individual biomolecules in the mixture and identifying specific molecular recognition events involving one or more target analytes are desirable for analytical biochemistry, biology and medicine.

SUMMARY OF THE INVENTION

This invention provides devices and methods for retentate chromatography. Retentate chromatography is a combinatorial method to provide high information resolution of analytes in complex mixtures through the use of multi-dimensional separation methods. It provides a unified analyte detection and functional analysis capability for biology and medicine that is characterized by a single, integrated operating system for the direct detection of analyte expression patterns associated with gene function, protein function, cell function, and the function of whole organisms. In one aspect, this invention provides a unified operating system for the discovery or diagnosis of gene function, protein function, or the function of entire macromolecular assemblies, cells, and whole organisms.

More particularly, analytes can be resolved in a variety of two-dimensional formats, thereby providing multi-dimensional information. Analytes are first separated in at least two different first dimensions based on their ability to be adsorbed to a stationary phase under at least two different selectivity conditions, such as anionic/cationic potential, hydrophobicity/hydrophilicity, or specific biomolecular recognition. Then the analytes are separated in a second dimension based on mass by desorption spectrometry (e.g., laser desorption mass spectrometry), which further provides detection of the separated analytes. The nature of the adsorbent to which the analytes adsorb provides physico-chemical information about the analyte.

Thus, this invention provides a molecular discovery and diagnostic device that is characterized by the inclusion of both parallel and multiplex analyte processing capabilities. Because analytes are directly detected, the invention enables the simultaneous transmission of two or more independent target analyte signals from the same "circuit" (i.e., addressable "chip" location) during a single unit operation.

Retentate chromatography is distinct from conventional chromatography in several ways. First, in retentate chromatography, analytes which are retained on the adsorbent are detected. In conventional chromatographic methods analytes are eluted off of the adsorbent prior to detection. There is no routine or convenient means for detecting analyte which is not eluted off the adsorbent in conventional chromatography. Thus, retentate chromatography provides direct information about chemical or structural characteristics of the retained analytes. Second, the coupling of adsorption chromatography with detection by desorption spectrometry provides extraordinary sensitivity, in the femtomolar range, and unusually fine resolution. Third, in part because it allows direct detection of analytes, retentate chromatography provides the ability to rapidly analyze retentates with a variety of different selectivity conditions, thus providing rapid, multi-dimensional characterization of analytes in a sample. Fourth, adsorbents can be attached to a substrate in an array of predetermined, addressable locations. This allows parallel processing of analytes exposed to different adsorbent sites (i.e., "affinity sites" or "spots") on the array under different elution conditions.

Retentate chromatography has many uses in biology and medicine. These uses include combinatorial biochemical separation and purification of analytes, the study of differential gene expression and molecular recognition events, diagnostics and drug discovery.

One basic use of retentate chromatography as an analytical tool involves exposing a sample to a combinatorial assortment of different adsorbent/eluant combinations and detecting the behavior of the analyte under the different conditions. This both purifies the analyte and identifies conditions useful for detecting the analyte in a sample. Substrates having adsorbents identified in this way can be used as specific detectors of the analyte or analytes. In a progressive extraction method, a sample is exposed to a first adsorbent/eluant combination and the wash, depleted of analytes that are adsorbed by the first adsorbent, is exposed to a second adsorbent to deplete it of other analytes. Selectivity conditions identified to retain analytes also can be used in preparative purification procedures in which an impure sample containing an analyte is exposed, sequentially, to adsorbents that retain it, impurities are removed, and the retained analyte is collected from the adsorbent for a subsequent round.

One aspect of the invention is that each class or type of molecular recognition event (e.g., target adsorbent-target analyte interaction), characterized by a particular selectivity condition at an addressable location within the array, is detected directly while the associated molecules are still localized (i.e., "retained") at the addressable location. That is, selection and detection, by direct means, does not require elution, recovery, amplification, or labeling of the target analyte.

Another aspect of the present invention is that the detection of one or more desirable molecular recognition events, at one or more locations within the addressable array, does not require removal or consumption of more than a small fraction of the total adsorbent-analyte. Thus, the unused portion can be interrogated further after one or more "secondary processing" events conducted directly in situ (i.e., within the boundary of the addressable location) for the purpose of structure and function elucidation, including further assembly or disassembly, modification, or amplification (directly or indirectly).

Adsorbents with improved specificity for an analyte can be developed by an iterative process, referred to as "progressive resolution," in which adsorbents or eluants proven to retain an analyte are tested with additional variables to identity combinations with better binding characteristics. Another method allows the rapid creation of substrates with antibody adsorbents specific for an analyte. The method involves docking the analyte to an adsorbent, and screening phage display libraries for phage that bind the analyte.

Retentate chromatography has uses in molecular and cellular biology, as well. Analytes that are differentially present in two samples (e.g., differentially expressed proteins in two cell extracts) can be identified by exposing the samples to a variety of adsorbent/eluant combinations for analysis by desorption spectrometry, thereby making use of the high information resolving power of the system that other separation and detections systems cannot match. Unknown target proteins can be identified by determining physicochemical characteristics, including molecular mass, based on the chemical characteristics of the adsorbent/eluant combination, and this information can be used to screen databases for proteins having similar profiles.

The methods in separation biochemistry and the adsorbents produced from these methods, are useful in diagnostics. More particularly, adsorbents, either chemical or biospecific, can be developed to detect important diagnostic markers. In certain embodiments, a substrate can have an array of adsorbent spots selected for a combination of markers diagnostic for a disease or syndrome.

Retentate chromatography also is useful in drug discovery. One member of a receptor/ligand pair is docked to an adsorbent, and its ability to bind the binding partner is tested in the presence of the agent. Because of the rapidity with which adsorption can be tested, combinatorial libraries of agents can be easily tested for their ability to modulate the interaction.

In one aspect this invention provides a method for high information resolution of at least one analyte in a sample. The method is a combinatorial separation method that includes separation and detection of multiple analytes in parallel. The method comprises the steps of a) exposing the analyte to at least two different selectivity conditions, each selectivity condition defined by the combination of an adsorbent and an eluant, to allow retention of the analyte by the adsorbent; and b) detecting retained analyte under the different selectivity conditions by desorption spectrometry. Detection of retained analyte under the different selectivity conditions provides a high information resolution of the analyte.

In one embodiment each different selectivity condition is defined at a different predetermined, addressable location for parallel processing. In another embodiment, the method comprises the steps of i) exposing the analyte to a first selectivity condition at a defined location to allow retention of the analyte by the adsorbent; ii) detecting retained analyte under the first selectivity condition by desorption spectrometry; iii) washing the adsorbent under a second, different selectivity condition at the defined location to allow retention of the analyte to the adsorbent; and iv) detecting retained analyte under the second selectivity condition by desorption spectrometry.

In another embodiment the analyte is an organic biomolecule, a multimeric molecular complex or macromolecular assembly. In another embodiment the organic biomolecule is an enzyme, an immunoglobulin, a cell surface receptor or an intracellular receptor.

In another embodiment the adsorbent comprises an anion, a cation, a hydrophobic interaction adsorbent, a polypeptide, a nucleic acid, a carbohydrate, a lectin, a dye, a reducing agent, a hydrocarbon or a combination thereof. In another embodiment the adsorbent is attached to a substrate comprising glass, ceramic, a magnetic material, an organic polymer, a conducting polymer, a native biopolymer, a metal or a metal coated with an organic polymer. In another embodiment the adsorbent is in the form of a microemulsion, a latex, a layer or a bead. In another embodiment the locations on the substrate are arranged in a line or an orthogonal array. In another embodiment the adsorbents are located on a substrate at different locations before the analytes are exposed to the selectivity conditions. In another embodiment the adsorbents are located on a substrate at different locations after the analytes are exposed to the selectivity conditions. In another embodiment the different selectivity conditions comprise different binding conditions or different elution conditions.

In another embodiment the step of detecting comprises detecting the mass of the analyte by laser desorption mass spectrometry.

In another embodiment the selectivity conditions are selected to optimize retention of analyte by an adsorbent. In another embodiment the at least one analyte is more than one analyte. In another embodiment the plurality of selectivity conditions are defined by at different adsorbents and the same eluant.

Another embodiment further comprises the step of providing a substrate comprising adsorbents at addressable locations, each adsorbent being an adsorbent from a selectivity condition identified to retain the analyte. In another embodiment the elution conditions differ according to pH, buffering capacity, ionic strength, a water structure characteristic, detergent type, detergent strength, hydrophobicity or dielectric constant. In another embodiment the plurality of selectivity conditions are defined by the same eluant.

In another embodiment this invention provides a method for sequential extraction of analytes from a sample. This is a combinatorial, serial separation and purification development method for multiple analytes in parallel. The method comprises the steps of a) exposing a sample comprising analytes to a first selectivity condition to allow retention of analytes by a first adsorbent and to create un-retained sample; b) collecting the un-retained sample comprising analytes, exposing the un-retained sample to a second selectivity condition to allow retention of analytes by a second adsorbent and to create un-retained sample; and c) detecting retained analyte under the different selectivity conditions by desorption spectrometry.

In another aspect this invention provides a substrate for desorption spectrometry comprising an adsorbent whose binding characteristics vary in a gradient along one or more linear axes.

In another aspect this invention provides a method for progressively identifying a selectivity condition with improved resolution for an analyte in a sample. The method comprises the steps of: (a) identify a selectivity condition that retains an analyte in a sample by (i) exposing a sample to a set of selectivity conditions, each selectivity condition defined by at least one binding characteristic and at least one elution characteristic; (ii) detecting analyte retained under each selectivity condition by desorption spectrometry; and (iii) identifying a selectivity condition that retains the analyte; and (b) identifying a selectivity condition with improved resolution for the analyte by: (i) selecting at least one binding characteristic or elution characteristic from the identified selectivity condition and adding it to a selectivity characteristic constant set; (ii) exposing the sample to a modified set of selectivity conditions wherein each selectivity condition in the modified set comprises (1) the selectivity characteristics in the constant set and (2) a binding characteristic or elution characteristic that is not in the constant set; and (iii) identifying a selectivity condition from the modified set by desorption spectrometry that retains the analyte with improved resolution compared with a prior identified selectivity condition. One embodiment comprises the step of repeating step (b) at least once. Another embodiment comprises repeating steps (b) until a selectivity condition is identified that retains only the target analyte from the sample.

In another aspect this invention provides a substrate for desorption spectrometry comprising an adsorbent from a selectivity conditions identified to resolve an analyte by the method of progressive resolution. In one embodiment the substrate comes in the form of a kit further comprising an eluant from the selectivity condition or instructions on using the eluant in combination with the adsorbent.

In another aspect this invention provides a method for preparative purification an analyte from an impure sample. The method comprises the steps of a) exposing the sample to a substrate under a plurality of different selectivity conditions; detecting retained analyte under the different selectivity conditions by desorption spectrometry; and identifying selectivity conditions under which the analyte is retained; b) purifying the analyte by repeating, for a plurality of different identified selectivity conditions, a sequence of steps comprising i) exposing the sample to an adsorbent under the identified selectivity condition to allow retention of the analyte by the adsorbent; ii) separating the analyte from an impurity that is not retained by the substrate; and iii) collecting the analyte from the adsorbent.

In another aspect this invention provides a method for preparing a substrate for detecting at least one analyte in a sample. This method is a combinatorial method for the design and identification of analyte-specific adsorbents. It is useful in detecting target analytes. The method comprises the steps of a) exposing the sample to at least two different selectivity conditions, each selectivity condition defined by the combination of an adsorbent and an eluant, to allow retention of the analyte by the adsorbent; b) identifying by desorption spectrometry at least one selectivity condition under which the analyte is retained; and c) preparing a substrate comprising at least one adsorbent of an identified selectivity condition. In one embodiment, the step of identifying comprises identifying at least one selectivity condition under which a plurality of analytes are retained. In another embodiment the step of preparing comprises preparing a substrate comprising a plurality of adsorbents that retain the analyte under an elution condition as a multiplex adsorbent.

In another aspect this invention provides a method of diagnosing in a subject a disease characterized by at least one diagnostic marker. This is a combinatorial method for simultaneous detection of multiple diagnostic markers. The method comprises the steps of a) providing a substrate for use in desorption spectrometry that comprises at least one addressable location, each addressable location comprising an adsorbent that resolves at least one of the diagnostic markers under an elution condition; b) exposing the substrate to a biological sample from the subject under the elution condition to allow retention of the diagnostic marker; and c) detecting retained diagnostic marker by desorption spectrometry. Detecting retained diagnostic marker provides a diagnosis of the disease.

In another aspect this invention provides a kit for detecting an analyte in a sample comprising (1) a substrate for use in desorption spectrometry that comprises at least one addressable location, each addressable location comprising an adsorbent that resolves an analyte under a selectivity condition comprising the adsorbent and an eluant, and (2) the eluant or instructions for exposing the sample to the selectivity condition. In one embodiment the kit is characterized by a plurality of diagnostic markers and the substrate comprises a plurality of addressable locations, each addressable location comprising an adsorbent that resolves at least one of the diagnostic markers.

In another aspect this invention provides a substrate for desorption spectrometry comprising at least one adsorbent in at least one addressable location wherein the at least one adsorbent resolves a plurality of diagnostic markers for a pathological condition from a patient sample.

In another aspect this invention provides a method for selecting identity candidates for an analyte protein. This method is a combinatorial method for protein identification based on at least two physico-chemical properties. The method comprises the steps of a) determining a value set specifying match parameters for at least a first and second physico-chemical characteristic of a protein analyte in a sample by i) exposing the analyte to a plurality of different selectivity conditions, wherein adsorption of the protein analyte to the substrate is mediated by a basis of attraction that identifies a physico-chemical characteristic of the protein analyte; and ii) detecting retained analyte under the different selectivity conditions by desorption spectrometry; and b) performing, in a programmable digital computer, the steps of i) accessing a database comprising, for each member of a set of reference polypeptides, a value set specifying at least a first and second physico-chemical characteristic of the reference polypeptides; ii) inputting the value set specifying the physico-chemical characteristics of the protein analyte; iii) sorting from the database, reference polypeptides having value sets within the match parameters. The sorted reference polypeptides provide identity candidates for the protein analyte. Unsorted references polypeptides are those excluded as identity candidates.

In another aspect this invention provides a method for sequentially retaining analytes. This method is a multimeric macromolecular or supramolecular assembly monitoring method. It is useful as a method for drug discovery by molecular recognition interference. The method comprises the steps of a) exposing a first sample to a primary adsorbent and to an eluant to allow retention of a first analyte by the adsorbent, and detecting the adsorbed analyte by desorption spectrometry, whereby the retained first analyte becomes a secondary adsorbent; b) exposing a second sample to the secondary adsorbent and to an eluant to allow retention of a second analyte by the secondary adsorbent, and detecting the adsorbed second analyte by desorption spectrometry, whereby the retained second analyte becomes a tertiary adsorbent.

In another aspect this invention provides a method of detecting an enzyme in a sample. The method comprises the steps of: a) providing a solid phase comprising an adsorbent and an enzyme substrate bound to the adsorbent, wherein the activity of the enzyme on the enzyme substrate produces a product having a characteristic molecular mass; b) exposing the substrate to the sample; and c) detecting the product by desorption spectrometry. Detecting the product provides a detection of the enzyme.

In another aspect this invention provides a method for determining whether an analyte is differentially present (e.g., differentially expressed) in a first and second biological sample. The method is useful for combinatorial method for differential gene expression monitoring by differential protein display. The method comprises the steps of a) determining a first retention map for the analyte in the first sample for at least one selectivity condition; b) determining a second retention map for the analyte in the second sample for the same selectivity condition; and c) detecting a difference between the first and the second retention maps. A difference in the retention maps provides a determination that the analyte is differentially present in first and second samples.

In one embodiment the method is for determining whether a protein is differentially expressed between two different cells, and the first and second samples comprise the cells or material from the cells. In another embodiment the method if for determining whether an agent alters the expression of a protein in a biological sample further comprising the step of administering the agent to a first biological sample but not to a second biological sample. In another embodiment the first biological sample derives from a healthy subject and the second biological sample is from a subject suffering from a pathological condition. The sample can be selected from, for example, blood, urine, serum and tissue. Analytes that are found to be increased in samples from pathological subjects are candidate diagnostic markers. Generally, confirmation of a dianostic marker involves detection of the marker in many subjects.

In another aspect this invention provides a method for identifying a ligand for a receptor. The method comprises the steps of: a) providing a substrate comprising an adsorbent wherein the receptor is bound to the adsorbent; b) exposing the bound receptor to a sample containing the ligand under conditions to allow binding between the receptor and the ligand; and c) detecting bound ligand by desorption spectrometry.

In another aspect this invention provides a screening method for determining whether an agent modulates binding between a target analyte and an adsorbent. This is a combinatorial method for drug discovery. The method comprises the steps of a) providing a substrate comprising an adsorbent to which the target analyte binds under an elution condition; b) exposing the substrate to the target analyte and to the agent under the elution condition to allow binding between the target analyte and the adsorbent; c) detecting an amount of binding between the target analyte and the adsorbent by desorption spectrometry; and d) determining whether the measured amount is different than a control amount of binding when the substrate is exposed to the target analyte under the elution condition without the agent. A difference between the measured amount and the control amount indicates that the agent modulates binding.

In one aspect, this invention provides a method of detecting a genetic package containing a polynucleotide that encodes a polypeptide agent that specifically binds to a target adsorbent. This is, in one aspect, a combinatorial method for selecting analyte-specific phage from a display library, including the use of target proteins isolated by retentate mapping or target proteins generated in situ by in vitro transcription and translation. The method comprises the steps of: a) providing a substrate comprising a target adsorbent; b) providing a display library that comprises a plurality of different genetic packages, each different genetic package comprising a polynucleotide that comprises a nucleotide sequence that encodes a polypeptide agent, and each different genetic package having a surface on which the encoded polypeptide agent is displayed; c) exposing the substrate to the display library under elution conditions to allow specific binding between a polypeptide agent and the target adsorbent, whereby a genetic package comprising the polypeptide agent is retained on the substrate; and d) detecting a genetic package retained on the substrate by desorption spectrometry.

In one embodiment of this method, the display library is a phage display library. In another embodiment the phage is M13. In another embodiment the polypeptide is a single chain antibody. In another embodiment the target analyte is a polypeptide analyte that is differentially expressed between cells of different phenotypes. In another embodiment the substrate comprises a cell or cell membrane.

In one embodiment, the step of providing the substrate comprising the target adsorbent comprises the steps of: i) providing a substrate comprising an adsorbent, wherein the adsorbent retains a target analyte under an elution condition; and ii) exposing the adsorbent to the target analyte under the elution condition to allow retention of the target analyte by the adsorbent, whereby the target analyte becomes the target adsorbent. In one embodiment, the target analyte is a target polypeptide and the step of ii) exposing the adsorbent comprises the step of producing the target polypeptide in situ on the adsorbent by in vitro translation of a polynucleotide encoding the target polypeptide, and can further comprise amplifying the polynucleotide sequence in situ on the substrate.

In another embodiment the substrate comprises (1) an adsorbent that binds an anchoring polypeptide and (2) at least one target genetic package having a surface displaying the anchoring polypeptide and a target adsorbent polypeptide, the target genetic package comprising a polynucleotide that comprises a nucleotide sequence that encodes the target adsorbent, wherein the target genetic package is bound to the adsorbent through the anchoring polypeptide.

In another embodiment the method further comprises any of the following steps: sequencing the nucleotide sequence that encodes the polypeptide agent; isolating the retained genetic package or producing the polypeptide agent.

In another aspect this invention provides a substrate for desorption spectrometry comprising an adsorbent that binds an anchoring polypeptide displayed on a surface of a genetic package, wherein the surface of the genetic package further displays a target polypeptide and wherein the genetic package comprises a polynucleotide comprising a nucleotide sequence that encodes the target polypeptide.

In another aspect this invention provides a method for detecting translation of a polynucleotide. The method comprises the steps of: a) providing a substrate comprising an adsorbent for use in desorption spectrometry; b) contacting the substrate with the polynucleotide encoding a polypeptide and with agents for in vitro translation of the polynucleotide, whereby the polypeptide is produced; c) exposing the substrate to an eluant to allow retention of the polypeptide by the adsorbent; and d) detecting retained polypeptide by desorption spectrometry. Detection of the polypeptide provides detection of translation of the polynucleotide.

BRIEF DESCRIPTION OF THE DRAWINGS

FIG. 4A shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve computer programs including code incorporating the present invention. Although a CD-ROM 17 is shown as the computer readable storage medium, other computer readable storage media including floppy disks, DRAM, hard drives, flash memory, tape, and the like may be utilized. Cabinet 7 also houses familiar computer components (not shown) such as a processor, memory, and the like.

FIG. 19A: anionic adsorbent; FIG. 19B: Normal phase adsorbent; FIG. 19C: Ni(II) adsorbent; FIG. 19D: Hydrophobic adsorbent.

FIGS. 20A-20C show progressive resolution of an analyte in *Hemophilus* lysate. The adsorbent in each case was an anionic adsorbent. FIG. 20A: In a first step, after exposure to the sample, the spot was washed with 150 µl of 20 mM sodium phosphate, 0.5 M sodium chloride, pH 7.0. In a second step, the adsorbent and sodium phosphate characteristic of the eluant were added to a constant set of characteristics. A new elution characteristic was added. FIG. 20B: In addition to 20 mM sodium phosphate, pH 7.0, the spot was washed with 0.05% Triton X100 and 0.15 M NaCl (150 µl, total). FIG. 20C: In addition to 20 mM sodium phosphate, pH 7.0, the spot was washed with 100 mM imidazole, 0.15 M NaCl (150 µl total).

FIG. 21A: Retentate map of normal serum on an adsorbent array Cu(II) site. FIG. 21B: Retentate map of disease serum on an adsorbent array Cu(II) site. FIG. 21C: Retained analytes of both serum samples are combined in an overlay fashion. To simplify the presentation, each peak of retained analyte is converted to a bar, the dashed bars represent analytes retained from a normal serum, and the solid bars represent analytes retained from a disease serum. FIG. 21D: To differentiate more clearly the difference between the two samples, a comparison plot is generated, where the ratio of the retained analytes from the samples are calculated and displayed. The two analytes marked with "*" show significant increases in the disease serum (5 to 10 fold increases).

FIGS. 24A-24E show detection of M13 phage by laser desorption mass spectrometry through the detection of the gene VIII coat protein. The dilutions of the original 1012 phage per ml range from 1:10 to 1:100,000,000.

FIG. 22A shows captured M13 phage with peaks representing gene VIII and gene III proteins. FIG. 22B is a control showing peaks representing the antibody adsorbent (singly and doubly charged).

FIGS. 26A-26D show adsorption of M13 phage bearing an anti-tat single chain antibody by tat protein adsorbent. Single strength is shown under phage dilutions from 1.10 to 1:10,000.

FIGS. 28 to 31 show the resolving power of retentate chromatography. FIG. 30 shows combined resolution from 0 kD to 30 kD of *Hemophilus* proteins from each of the three adsorbents. FIG. 31 shows combined resolution from 20 kD to 100 kD of *Hemophilus* proteins from each of the three adsorbents.

FIGS. 33A-33B show binding of a specific ligand to GST fusion receptor docked to an adsorbent array (FIG. 33A) and lack of binding of the ligand to a control array that does not include the GST fusion receptor (FIG. 33B).

DETAILED DESCRIPTION OF THE INVENTION

I. Definitions

Figure 1:
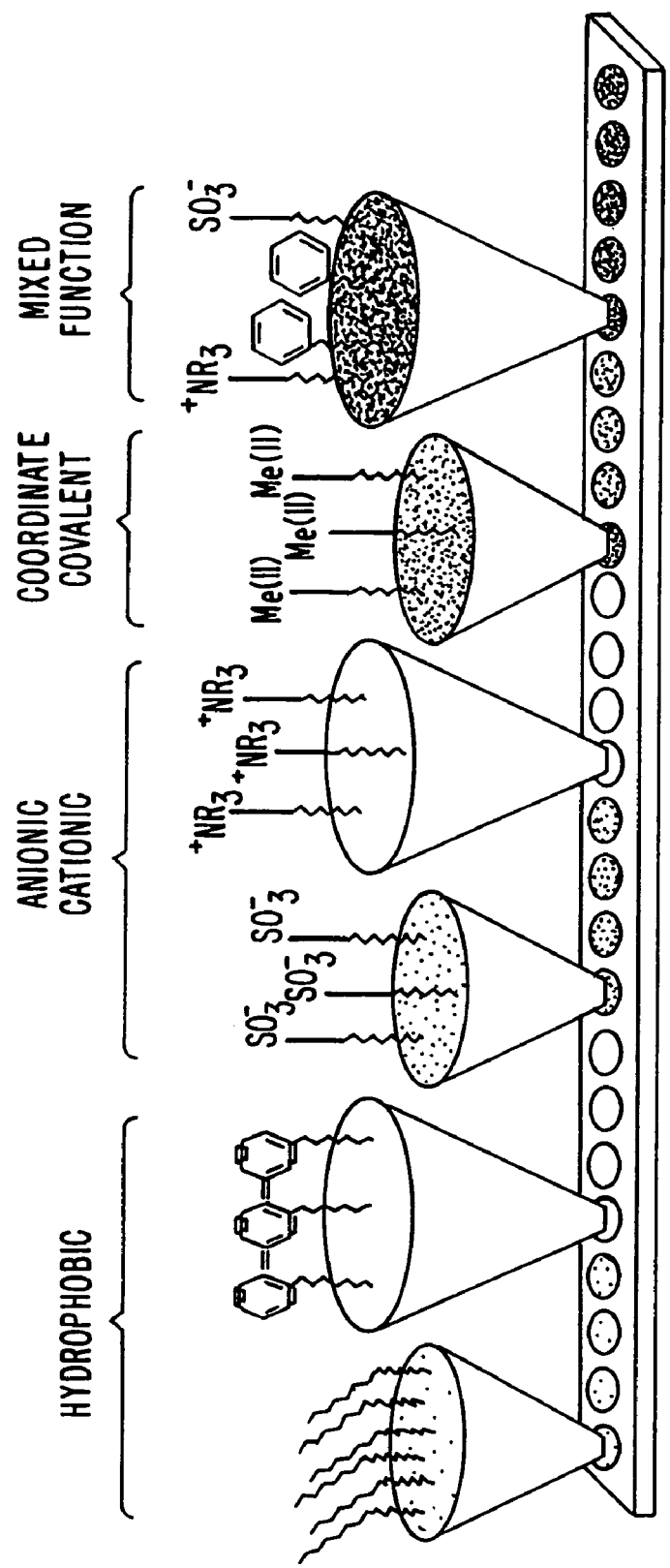
FIG. 1 depicts a substrate containing a plurality of adsorbent spots in the form of a strip. The strip contains six different sets adsorbents classified according to a basis of attraction (hydrophobic, ionic, coordinate covalent and mixed function). The strip contains several spots for each type of adsorbent, allowing interrogation of the spots at different times with different eluants, or for archiving and subsequent analysis.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

"Analyte" refers to a component of a sample which is desirably retained and detected. The term can refer to a single component or a set of components in the sample.

"Adsorbent" refers to any material capable of adsorbing an analyte. The term "adsorbent" is used herein to refer both to a single material ("monoplex adsorbent") (e.g., a compound or functional group) to which the analyte is exposed, and to a plurality of different materials ("multiplex adsorbent") to which a sample is exposed. The adsorbent materials in a multiplex adsorbent are referred to as "adsorbent species." For example, an addressable location on a substrate can comprise a multiplex adsorbent characterized by many different adsorbent species (e.g., anion exchange materials, metal chelators, or antibodies), having different binding characteristics.

"Adsorb" refers to the detectable binding between an absorbent and an analyte either before or after washing with an eluant (selectivity threshold modifier).

"Substrate" refers to a solid phase to which an adsorbent is attached or deposited.

"Binding characteristic" refers to a chemical and physical feature that dictates the attraction of an adsorbent for an analyte. Two adsorbents have different binding characteristics if, under the same elution conditions, the adsorbents bind the same analyte with different degrees of affinity. Binding characteristics include, for example, degree of salt-promoted interaction, degree of hydrophobic interaction, degree of hydrophilic interaction, degree of electrostatic interaction, and others described herein.

"Binding conditions" refer to the binding characteristics to which an analyte is exposed.

"Eluant" refers to an agent, typically a solution, that is used to mediate adsorption of an analyte to an adsorbent. Eluants also are referred to as "selectivity threshold modifiers."

"Elution characteristic" refers to a feature that dictates the ability of a particular eluant (selectivity threshold modifier) to mediate adsorption between an analyte and an absorbent. Two eluants have different elution characteristics if, when put in contact with an analyte and adsorbent, the degree of affinity of the analyte for the adsorbent differs. Elution characteristics include, for example, pH, ionic strength, modification of water structure, detergent strength, modification of hydrophobic interactions, and others described herein.

"Elution conditions" refer to the elution characteristics to which an analyte is exposed.

"Selectivity characteristic" refers to a feature of the combination of an adsorbent having particular binding characteristics and an eluant having particular elution characteristics that dictate the specificity with which the analyte is retained to the adsorbent after washing with the eluant.

"Selectivity conditions" refer to the selectivity characteristics to which an analyte is exposed.

"Basis for attraction" refers to the chemical and/or physico-chemical properties which cause one molecule to be attracted to another.

"Strength of attraction" refers to the intensity of the attraction of one molecule for another (also known as affinity).

"Resolve," "resolution," or "resolution of analyte" refers to the detection of at least one analyte in a sample. Resolution includes the detection of a plurality of analytes in a sample by separation and subsequent differential detection. Resolution does not require the complete separation of an analyte from all other analytes in a mixture. Rather, any separation that allows the distinction between at least two analytes suffices.

"High information resolution" refers to resolution of an analyte in a manner that permits not only detection of the analyte, but also at least one physico-chemical property of the analyte to be evaluated, e.g., molecular mass.

"Desorption spectrometry" refers to a method of detecting an analyte in which the analyte is exposed to energy which desorbs the analyte from a stationary phase into a gas phase, and the desorbed analyte or a distinguishable portion of it is directly detected by a detector, without an intermediate step of capturing the analyte on a second stationary phase.

"Detect" refers to identifying the presence, absence or amount of the object to be detected.

"Retention" refers to an adsorption of an analyte by an adsorbent after washing with an eluant.

"Retention data" refers to data indicating the detection (optionally including detecting mass) of an analyte retained under a particular selectivity condition.

"Retention map" refers to a value set specifying retention data for an analyte retained under a plurality of selectivity conditions.

"Recognition profile" refers to a value set specifying relative retention of an analyte under a plurality of selectivity conditions.

"Complex" refers to analytes formed by the union of 2 or more analytes.

"Fragment" refers to the products of the chemical, enzymatic, or physical breakdown of an analyte. Fragments may be in a neutral or ionic state.

"Differential expression" refers to a detectable difference in the qualitative or quantitative presence of an analyte.

"Biological sample" refers to a sample derived from a virus, cell, tissue, organ or organism including, without limitation, cell, tissue or organ lysates or homogenates, or body fluid samples, such as blood, urine or cerebrospinal fluid.

"Organic biomolecule" refers to an organic molecule of biological origin, e.g., steroids, amino acids, nucleotides, sugars, polypeptides, polynucleotides, complex carbohydrates or lipids.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

"Biopolymer" refers to a polymer of biological origin, e.g., polypeptides, polynucleotides, polysaccharides or polyglycerides (e.g., di- or tri-glycerides).

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, Bio/Technology (1988) 6:1165.) Quantitation of the signal is achieved by, e.g., scintillation counting, densitometry, or flow cytometry.

"Plurality" means at least two.

"Purify" or "purification" means removing at least one contaminant from the composition to be purified. Purification does not require that the purified compound be 100% pure.

A "ligand" is a compound that specifically binds to a target molecule.

A "receptor" is compound that specifically binds to a ligand.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

"Agent" refers to a chemical compound, a mixture of chemical compounds, a sample of undetermined composition, a combinatorial small molecule array, a biological macromolecule, a bacteriophage peptide display library, a bacteriophage antibody (e.g., scFv) display library, a polysome peptide display library, or an extract made from biological materials such as bacteria, plants, fungi, or animal cells or tissues. Suitable techniques involve selection of libraries of recombinant antibodies in phage or similar vectors. See, Huse et al. (1989) *Science* 246: 1275-1281; and Ward et al. (1989) *Nature* 341: 544-546. The protocol described by Huse is rendered more efficient in combination with phage display technology. See, e.g., Dower et al., WO 91/17271 and McCafferty et al., WO 92/01047.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well. Appropriate unicellular hosts include any of those routinely used in expressing eukaryotic or mammalian polynucleotides, including, for example, prokaryotes, such as *E. coli*; and eukaryotes, including for example, fungi, such as yeast; and mammalian cells, including insect cells (e.g., Sf9) and animal cells such as CHO, R1.1, B-W, L-M, African Green Monkey Kidney cells (e.g. COS 1, COS 7, BSC 1, BSC 40 and BMT 10) and cultured human cells.

"Expression control sequence" refers to a nucleotide sequence in a polynucleotide that regulates the expression (transcription and/or translation) of a nucleotide sequence operatively linked to it. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible, repressible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Energy absorbing molecule" refers to refers to a molecule that absorbs energy from an energy source in a desorption spectrometer thereby enabling desorption of analyte from a probe surface. Energy absorbing molecules used in MALDI are frequently referred to as "matrix." Cinnamic acid derivatives, cinapinic acid and dihydroxybenzoic acid are frequently used as energy absorbing molecules in laser desorption of bioorganic molecules.

II. Retentate Chromatography

Retentate chromatography is a method for the multidimensional resolution of analytes in a sample. The method involves (1) selectively adsorbing analytes from a sample to a substrate under a plurality of different adsorbent/eluant combinations ("selectivity conditions") and (2) detecting the retention of adsorbed analytes by desorption spectrometry. Each selectivity condition provides a first dimension of separation, separating adsorbed analytes from those that are not adsorbed. Desorption mass spectrometry provides a second dimension of separation, separating adsorbed analytes from each other according to mass. Because retentate chromatography involves using a plurality of different selectivity conditions, many dimensions of separation are achieved. The relative adsorption of one or more analytes under the two selectivity conditions also can be determined. This multidimensional separation provides both resolution of the analytes and their characterization.

Further, the analytes thus separated remain docked in a retentate map that is amenable to further manipulation to examine, for example, analyte structure and/or function. Also, the docked analytes can, themselves, be used as adsorbents to dock other analytes exposed to the substrate. In sum, the present invention provides a rapid, multidimensional and high information resolution of analytes.

The method can take several forms. In one embodiment, the analyte is adsorbed to two different adsorbents at two physically different locations and each adsorbent is washed with the same eluant (selectivity threshold modifier). In another embodiment, the analyte is adsorbed to the same adsorbent at two physically different locations and washed with two different eluants. In another embodiment, the analyte is adsorbed to two different adsorbents in physically different locations and washed with two different eluants. In another embodiment, the analyte is adsorbed to an adsorbent and washed with a first eluant, and retention is detected; then, the adsorbed analyte is washed with a second, different eluant, and subsequent retention is detected.

A. Methods of Performing Retentate Chromatography

1. Exposing the Analyte to Selectivity Conditions a. Substrate Preparation

In performing retentate chromatography an analyte that is retained by an adsorbent is presented to an energy source on a substrate. A sample containing the analyte may be contacted to the adsorbent before or after the adsorbent is affixed to the substrate that will serve to present the analyte to the desorption means. For contacting purposes, the adsorbent may be in liquid form or solid form (i.e., on a substrate or solid phase). Specifically, the adsorbent may be in the form of a solution, suspension, dispersion, water-in-oil emulsion, oil-in-water emulsion, or microemulsion. When the adsorbent is provided in the form of a suspension, dispersion, emulsion or microemulsion, a suitable surfactant may also be present. In this embodiment, the sample may be contacted with the adsorbent by admixing a liquid sample with the liquid adsorbent. Alternatively, the sample may be provided on a solid support and contacting will be accomplished by bathing, soaking, or dipping the sample-containing solid support in the liquid adsorbent. In addition, the sample may be contacted by spraying or washing over the solid support with the liquid adsorbent. In this embodiment, different adsorbents may be provided in different containers.

In one embodiment, the adsorbent is provided on a substrate. The substrate can be any material which is capable of binding or holding the adsorbent. Typically, the substrate is comprised of glass; ceramic; electrically conducting polymers (e.g. carbonized PEEK); TEFLON® coated materials; organic polymers; native biopolymers; metals (e.g., nickel, brass, steel or aluminum); films; porous and non-porous beads of cross-linked polymers (e.g., agarose, cellulose or dextran); other insoluble polymers; or combinations thereof.

In one embodiment, the substrate takes the form of a probe or a sample presenting means that is inserted into a desorption detector. For example, referring to FIG. 1, the substrate can take the form of a strip. The adsorbent can be attached to the substrate in the form of a linear array of spots, each of which can be exposed to the analyte. Several strips can be joined together so that the plurality of adsorbents form an array 30 having discrete spots in defined rows. The substrate also can be in the form of a plate having an array of horizontal and vertical rows of adsorbents which form a regular geometric pattern such as a square, rectangle or circle.

Probes can be produced as follows. The substrate can be any solid material, for example, stainless steel, aluminum or a silicon wafer. A metal substrate can then be coated with a material that allows derivitization of the surface. For example a metal surface can be coated with silicon oxide, titanium oxide or gold.

The surface is then derivatized with a bifunctional linker. The linker includes at one end a functional group that can covalently bind with a functional group on the surface. Thus the functional group can be an inorganic oxide or a sulfhydryl group for gold. The other end of the linker generally has an amino functionality. Useful bifunctional linkers include aminopropyl triethoxysilane or aminoethyl disulfide.

Once bound to the surface, the linkers are further derivatized with groups that function as the adsorbent. Generally the adsorbent is added to addressable locations on the probe. In one type of probe spots of about 3 mm in diameter are arrange in an orthogonal array. The adsorbents can, themselves, be part of bifunctional molecules containing a group reactive with the available amino group and the functional group that acts as the adsorbent. Functional groups include, for example, normal phase (silicon oxide), reverse phase ($C_{18}$ aliphatic hydrocarbon), quaternary amine and sulphonate. Also, the surface can be further derivatized with other bifunctional molecules such as carbodiimide and N-hydroxysuccinimide, creating a pre-activated blank. These blanks can be functionalized with bioorganic adsorbents (e.g., nucleic acids, antibodies and other protein ligands). Biopolymers can bind the functional groups on the blanks through amine residues or sulfhydryl residues. In one embodiment, the adsorbents are bound to cross-linked polymers (e.g., films) that are themselves bound to the surface of the probe through the available functional groups. Such polymers include, for example, cellulose, dextran, carboxymethyl dextran, polyacrylamide and mixtures of these. Probes with attached adsorbents are ready for use.

In another embodiment, the adsorbent is attached to a first substrate to provide a solid phase, such as a polymeric or glass bead, which is subsequently positioned on a second substrate which functions as the means for presenting the sample to the desorbing energy of the desorption detector. For example, the second substrate can be in the form a plate having a series of wells at predetermined addressable locations. The wells can function as containers for a first substrate derivatized with the adsorbent, e.g., polymeric beads derivatized with the adsorbent. One advantage of this embodiment is that the analyte can be adsorbed to the first substrate in one physical context, and transferred to the sample presenting substrate for analysis by desorption spectrometry.

Typically, the substrate is adapted for use with the detectors employed in the methods of the present invention for detecting the analyte bound to and retained by the adsorbent. In one embodiment, the substrate is removably insertable into a desorption detector where an energy source can strike the spot and desorb the analyte. The substrate can be suitable for mounting in a horizontally and/or vertically translatable carriage that horizontally and/or vertically moves the substrate to successively position each predetermined addressable location of adsorbent in a path for interrogation by the energy source and detection of the analyte bound thereto. The substrate can be in the form of a conventional mass spectrometry probe The strips, plates, or probes of substrate can be produced using conventional techniques. Thereafter, the adsorbent can be directly or indirectly coupled, fitted, or deposited on the substrate prior to contacting with the sample containing the analyte. The adsorbent may be directly or indirectly coupled to the substrate by any suitable means of attachment or immobilization. For example, the adsorbent can be directly coupled to the substrate by derivatizing the substrate with the adsorbent to directly bind the adsorbent to the substrate through covalent or non-covalent bonding.

Attachment of the adsorbent to the substrate can be accomplished through a variety of mechanisms. The substrate can be derivatized with a fully prepared adsorbent molecule by attaching the previously prepared adsorbent molecule to the substrate. Alternatively, the adsorbent can be formed on the substrate by attaching a precursor molecule to the substrate and subsequently adding additional precursor molecules to the growing chain bound to the substrate by the first precursor molecule. This mechanism of building the adsorbent on the substrate is particularly useful when the adsorbent is a polymer, particularly a biopolymer such as a DNA or RNA molecule. A biopolymer adsorbent can be provided by successively adding bases to a first base attached to the substrate using methods known in the art of oligonucleotide chip technology. See, e.g., U.S. Pat. No. 5,445,934 (Fodor et al.).

Figure 2:
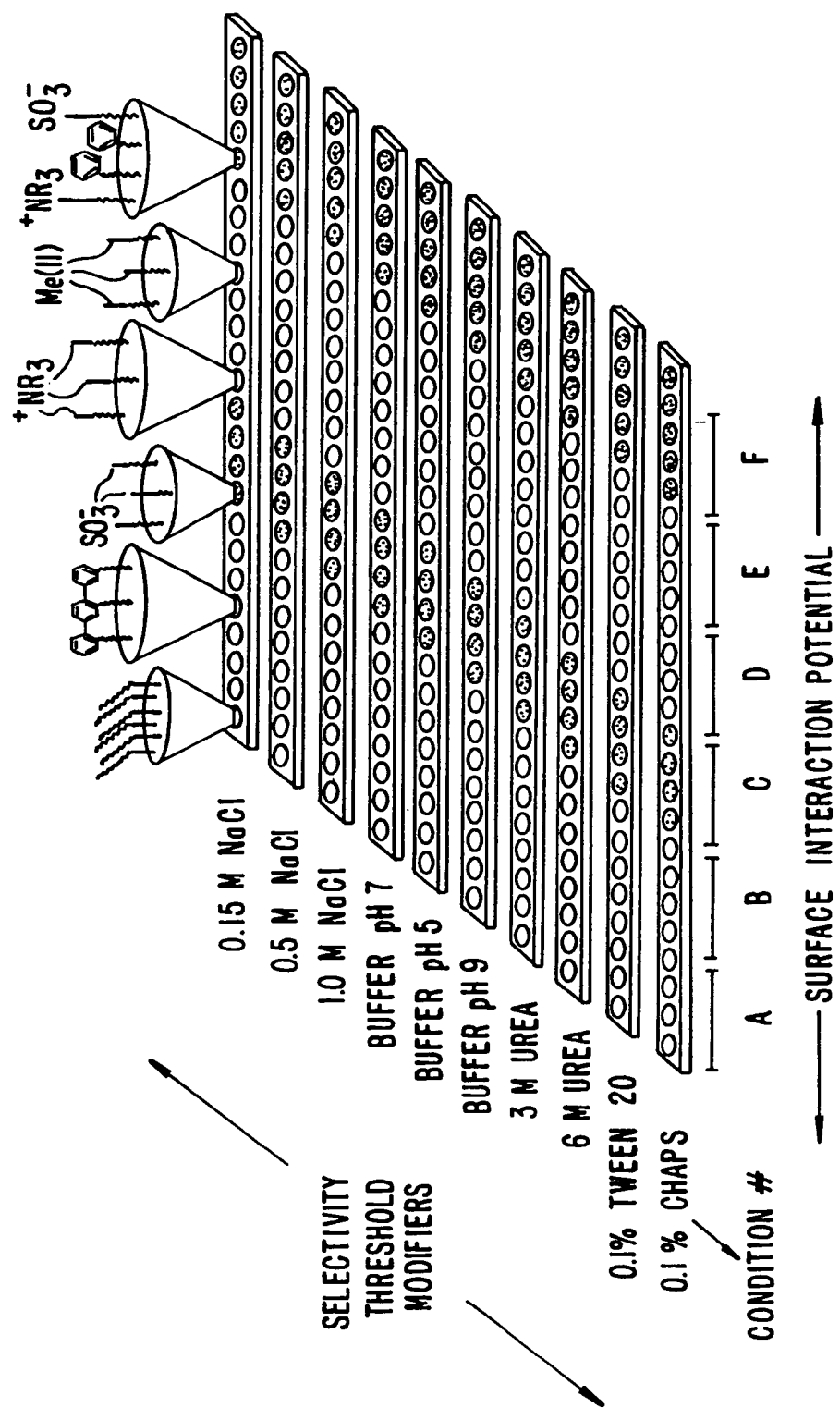
FIG. 2 depicts an orthogonal array of adsorbents (surface interaction potentials) in predetermined, addressable locations. The array also can take the form of a plate. The array includes various adsorbents. Upon exposure to the analyte, each strip can be washed by a variety of eluants (selectivity threshold modifiers). Analysis of retention under different selectivity conditions results in retention map or recognition profile.
Figure 3:
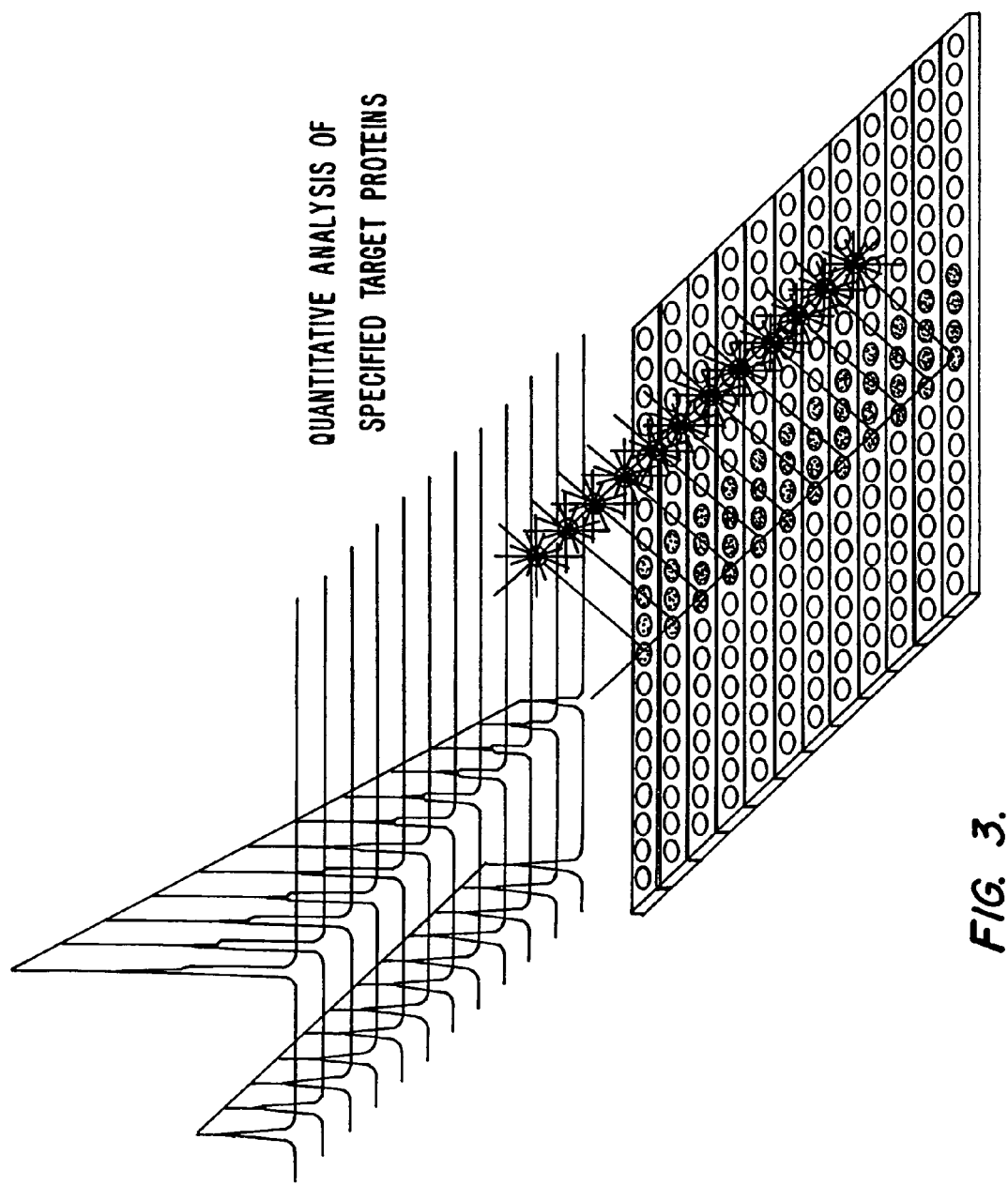
FIG. 3 is a representation of the quantitative analysis of analytes by desorption of analyte from given locations on the array and quantitative detection of the desorbed analyte by laser desorption mass spectrometry.
Figure 4A:
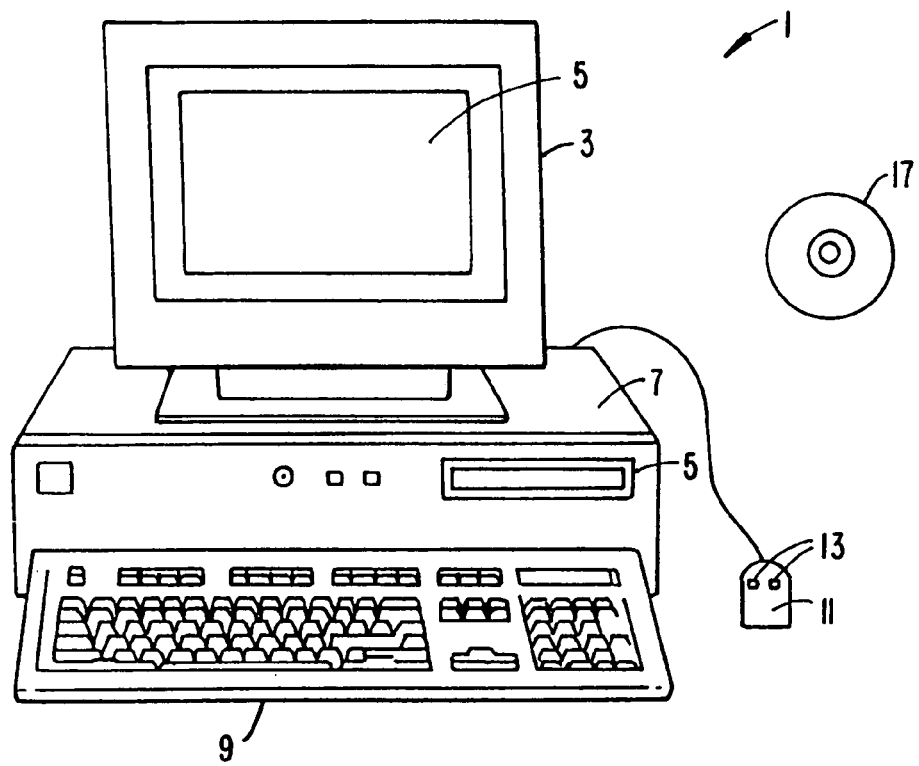
FIG. 4A illustrates an example of a computer system used to execute software that can be used to analyze data generated by the present invention.
Figure 4B:
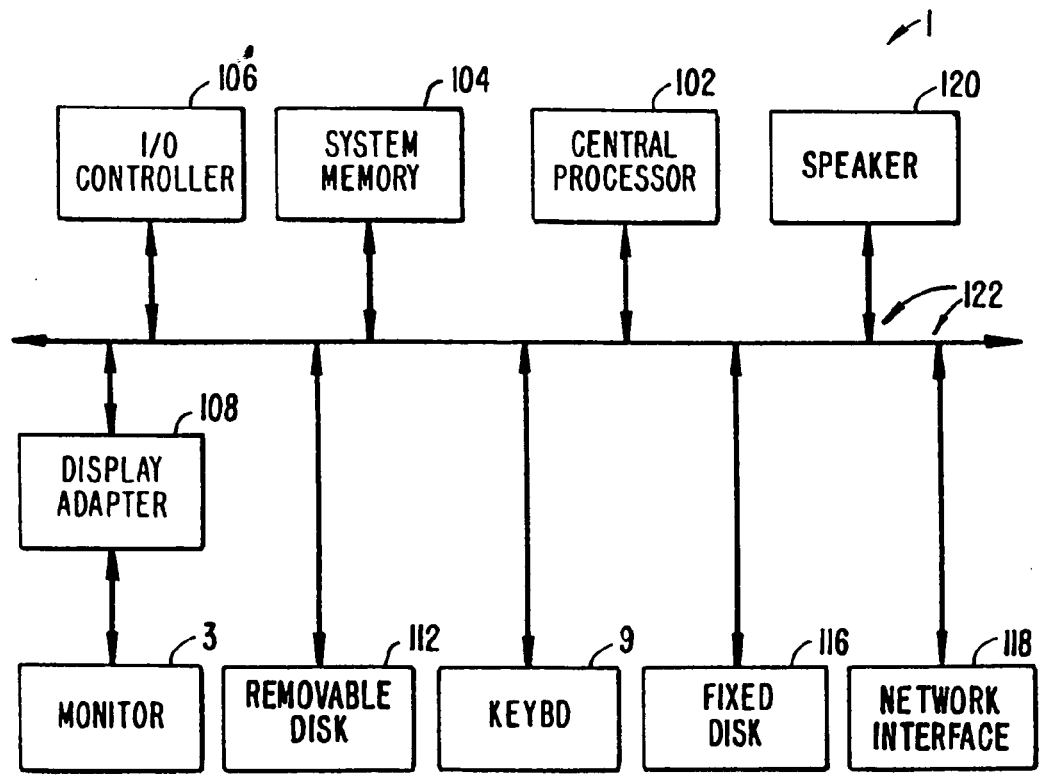
FIG. 4B shows a system block diagram of computer system 1 used to execute software that can be used to analyze data generated by the present invention. As in FIG. 4A, computer system 1 includes monitor 3 and keyboard 9. Computer system 1 further includes subsystems such as a central processor 102, system memory 104, I/O controller 106, display adapter 108, removable disk 112, fixed disk 116, network interface 118, and speaker 120. Removable disk 112 is representative of removable computer readable media like floppies, tape, CD-ROM, removable hard drive, flash memory, and the like. Fixed disk 116 is representative of an internal hard drive, DRAM, or the like. Other computer systems suitable for use with the present invention may include additional or fewer subsystems. For example, another computer system could include more than one processor 102 (i.e., a multi-processor system) or memory cache.

As can be seen from FIG. 2, as few as two and as many as 10, 100, 1000, 10,000 or more adsorbents can be coupled to a single substrate. The size of the adsorbent site may be varied, depending on experimental design and purpose. However, it need not be larger than the diameter of the impinging energy source (e.g., laser spot diameter). The spots can continue the same or different adsorbents. In some cases, it is advantageous to provide the same adsorbent at multiple locations on the substrate to permit evaluation against a plurality of different eluants or so that the bound analyte can be preserved for future use or reference, perhaps in secondary processing. By providing a substrate with a plurality of different adsorbents, it is possible to utilize the plurality of binding characteristics provided by the combination of different adsorbents with respect to a single sample and thereby bind and detect a wider variety of different analytes. The use of a plurality of different adsorbents on a substrate for evaluation of a single sample is essentially equivalent to concurrently conducting multiple chromatographic experiments, each with a different chromatography column, but the present method has the advantage of requiring only a single system.

When the substrate includes a plurality of adsorbents, it is particularly useful to provide the adsorbents in predetermined addressable locations. By providing the adsorbents in predetermined addressable locations, it is possible to wash an adsorbent at a first predetermined addressable location with a first eluant and to wash an adsorbent at a second predetermined addressable location with a second eluant. In this manner, the binding characteristics of a single adsorbent for the analyte can be evaluated in the presence of multiple eluants which each selectively modify the binding characteristics of the adsorbent in a different way. The addressable locations can be arranged in any pattern, but preferably in regular patters, such as lines, orthogonal arrays, or regular curves, such as circles. Similarly, when the substrate includes a plurality of different adsorbents, it is possible to evaluate a single eluant with respect to each different adsorbent in order to evaluate the binding characteristics of a given adsorbent in the presence of the eluant. It is also possible to evaluate the binding characteristics of different adsorbents in the presence of different eluants.

(1) Incremental or Gradient Adsorbent Surfaces

A series of adsorbents having different binding characteristics can be provided by synthesizing a plurality of different polymeric adsorbents on the substrate. The different polymeric adsorbents can be provided by attaching a precursor molecule to the substrate, initializing the polymerization reaction, and terminating the polymerization reaction at varied degrees of completion for each adsorbent. Also, the terminal functional groups in the polymers can be reacted so as to chemically derivatize them to varying degrees with different affinity reagent (e.g., —$NH_3$, or $COO^-$). By terminating the polymerization or derivatization reaction, adsorbents of varying degrees of polymerization or derivatization are produced. The varying degrees of polymerization or derivatization provide different binding characteristics for each different polymeric adsorbent. This embodiment is particularly useful for providing a plurality of different biopolymer adsorbents on a substrate.

If desired, the polymerization reactions can be carried out in a reaction vessel, rather than on the substrate itself. For example, polymeric adsorbents of varying binding characteristics can be provided by extracting an aliquot of product from the reaction vessel as the polymerization/derivatization reaction is proceeding. The aliquots, having been extracted at various points during the polymerization/derivatization reaction will exhibit varied degrees of polymerization/derivatization to yield a plurality of different adsorbents. The different aliqouts of product can then be utilized as adsorbents having different binding characteristics. Alternatively, a plurality of different adsorbents can be provided by sequentially repeating the steps of terminating the reaction, withdrawing an aliquot of product, and re-starting the polymerization/derivatization reaction. The products extracted at each termination point will exhibit varying degrees of polymerization/derivatization and as a result will provide a plurality of adsorbents having different binding characteristics.

In one embodiment, a substrate is provided in the form of a strip or a plate that is coated with adsorbent in which one or more binding characteristic varies in a one- or two-dimensional gradient. For example, a strip is provided having an adsorbent that is weakly hydrophobic at one end and strongly hydrophobic at the other end. Or, a plate is provided that is weakly hydrophobic and anionic in one corner, and strongly hydrophobic and anionic in the diagonally opposite corner. Such adsorption gradients are useful in the qualitative analysis of an analyte. Adsorption gradients can be made by a controlled spray application or by flowing material across a surface in a time-wise manner to allow incremental completion of a reaction over the dimension of the gradient. This process can be repeated, at right angles, to provide orthogonal gradients of similar or different adsorbents with different binding characteristics.

The sample containing the analyte may be contacted to the adsorbent either before or after the adsorbent is positioned on the substrate using any suitable method which will enable binding between the analyte and the adsorbent. The adsorbent can simply be admixed or combined with the sample. The sample can be contacted to the adsorbent by bathing or soaking the substrate in the sample, or dipping the substrate in the sample, or spraying the sample onto the substrate, by washing the sample over the substrate, or by generating the sample or analyte in contact with the adsorbent. In addition, the sample can be contacted to the adsorbent by solubilizing the sample in or admixing the sample with an eluant and contacting the solution of eluant and sample to the adsorbent using any of the foregoing techniques (i.e., bathing, soaking, dipping, spraying, or washing over).

b. Contacting the Analyte to the Adsorbent

Exposing the sample to an eluant prior to binding the analyte to the adsorbent has the effect of modifying the selectivity of the adsorbent while simultaneously contacting the sample to the adsorbent. Those components of the sample which will bind to the adsorbent and thereby be retained will include only those components which will bind the adsorbent in the presence of the particular eluant which has been combined with the sample, rather than all components which will bind to the adsorbent in the absence of elution characteristics which modify the selectivity of the adsorbent.

The sample should be contacted to the adsorbent for a period of time sufficient to allow the analyte to bind to the adsorbent. Typically, the sample is contacted with the analyte for a period of between about 30 seconds and about 12 hours. Preferably, the sample is contacted to the analyte for a period of between about 30 seconds and about 15 minutes.

The temperature at which the sample is contacted to the adsorbent is a function of the particular sample and adsorbents selected. Typically, the sample is contacted to the adsorbent under ambient temperature and pressure conditions, however, for some samples, modified temperature (typically 4° C. through 37° C.) and pressure conditions can be desirable and will be readily determinable by those skilled in the art.

Another advantage of the present invention over conventional detection techniques is that the present invention enables the numerous different experiments to be conducted on a very small amount of sample. Generally, a volume of sample containing from a few atommoles to 100 picomoles of analyte in about 1 µl to 500 µl is sufficient for binding to the adsorbent. Analyte may be preserved for future experiments after binding to the adsorbent because any adsorbent locations which are not subjected to the steps of desorbing and detecting all of the retained analyte will retain the analyte thereon. Therefore, in the case where only a very small fraction of sample is available for analysis, the present invention provides the advantage of enabling a multitude of experiments with different adsorbents and/or eluants to be carried out at different times without wasting sample.

c. Washing the Adsorbent with Eluants

After the sample is contacted with the analyte, resulting in the binding of the analyte to the adsorbent, the adsorbent is washed with eluant. Typically, to provide a multi-dimensional analysis, each adsorbent location is washed with at least a first and a second different eluants. Washing with the eluants modifies the analyte population retained on a specified adsorbent. The combination of the binding characteristics of the adsorbent and the elution characteristics of the eluant provide the selectivity conditions which control the analytes retained by the adsorbent after washing. Thus, the washing step selectively removes sample components from the adsorbent.

The washing step can be carried out using a variety of techniques. For example, as seen above, the sample can be solubilized in or admixed with the first eluant prior to contacting the sample to the adsorbent. Exposing the sample to the first eluant prior to or simultaneously with contacting the sample to the adsorbent has, to a first approximation, the same net effect as binding the analyte to the adsorbent and subsequently washing the adsorbent with the first eluant. After the combined solution is contacted to the adsorbent, the adsorbent can be washed with the second or subsequent eluants.

Washing an adsorbent having the analyte bound thereto can be accomplished by bathing, soaking, or dipping the substrate having the adsorbent and analyte bound thereon in an eluant; or by rinsing, spraying, or washing over the substrate with the eluant. The introduction of eluant to small diameter spots of affinity reagent is best achieved by a microfluidics process.

When the analyte is bound to adsorbent at only one location and a plurality of different eluants are employed in the washing step, information regarding the selectivity of the adsorbent in the presence of each eluant individually may be obtained. The analyte bound to adsorbent at one location may be determined after each washing with eluant by following a repeated pattern of washing with a first eluant, desorbing and detecting retained analyte, followed by washing with a second eluant, and desorbing and detecting retained analyte. The steps of washing followed by desorbing and detecting can be sequentially repeated for a plurality of different eluants using the same adsorbent. In this manner the adsorbent with retained analyte at a single location may be reexamined with a plurality of different eluants to provide a collection of information regarding the analytes retained after each individual washing.

The foregoing method is also useful when adsorbents are provided at a plurality of predetermined addressable locations, whether the adsorbents are all the same or different. However, when the analyte is bound to either the same or different adsorbents at a plurality of locations, the washing step may alternatively be carried out using a more systematic and efficient approach involving parallel processing. Namely, the step of washing can be carried out by washing an adsorbent at a first location with eluant, then washing a second adsorbent with eluant, then desorbing and detecting the analyte retained by the first adsorbent and thereafter desorbing and detecting analyte retained by the second adsorbent. In other words, all of the adsorbents are washed with eluant and thereafter analyte retained by each is desorbed and detected for each location of adsorbent. If desired, after detection at each adsorbent location, a second stage of washings for each adsorbent location may be conducted followed by a second stage of desorption and detection. The steps of washing all adsorbent locations, followed by desorption and detection at each adsorbent location can be repeated for a plurality of different eluants. In this manner, and entire array may be utilized to efficiently determine the character of analytes in a sample. The method is useful whether all adsorbent locations are washed with the same eluant in the first washing stage or whether the plurality of adsorbents are washed with a plurality of different eluants in the first washing stage.

2. Detection

Analytes retained by the adsorbent after washing are adsorbed to the substrate. Analytes retained on the substrate are detected by desorption spectrometry: desorbing the analyte from the adsorbent and directly detecting the desorbed analytes.

a. Methods For Desorption

Desorbing the analyte from the adsorbent involves exposing the analyte to an appropriate energy source. Usually this means striking the analyte with radiant energy or energetic particles. For example, the energy can be light energy in the form of laser energy (e.g., UV laser) or energy from a flash lamp. Alternatively, the energy can be a stream of fast atoms. Heat may also be used to induce/aid desorption.

Methods of desorbing and/or ionizing analytes for direct analysis are well known in the art. One such method is called matrix-assisted laser desorption/ionization, or MALDI. In MALDI, the analyte solution is mixed with a matrix solution and the mixture is allowed to crystallize after being deposited on an inert probe surface, trapping the analyte within the crystals may enable desorption. The matrix is selected to absorb the laser energy and apparently impart it to the analyte, resulting in desorption and ionization. Generally, the matrix absorbs in the UV range. MALDI for large proteins is described in, e.g., U.S. Pat. No. 5,118,937 (Hillenkamp et al.) and U.S. Pat. No. 5,045,694 (Beavis and Chait).

Surface-enhanced laser desorption/ionization, or SELDI, represents a significant advance over MALDI in terms of specificity, selectivity and sensitivity. SELDI is described in U.S. Pat. No. 5,719,060 (Hutchens and Yip). SELDI is a solid phase method for desorption in which the analyte is presented to the energy stream on a surface that enhances analyte capture and/or desorption. In contrast, MALDI is a liquid phase method in which the analyte is mixed with a liquid material that crystallizes around the analyte.

One version of SELDI, called SEAC (Surface-Enhanced Affinity Capture), involves presenting the analyte to the desorbing energy in association with an affinity capture device (i.e., an adsorbent). It was found that when an analyte is so adsorbed, it can be presented to the desorbing energy source with a greater opportunity to achieve desorption of the target analyte. An energy absorbing material can be added to the probe to aid desorption. Then the probe is presented to the energy source for desorbing the analyte Another version of SELDI, called SEND (Surface-Enhanced Neat Desorption), involves the use of a layer of energy absorbing material onto which the analyte is placed. A substrate surface comprises a layer of energy absorbing molecules chemically bond to the surface and/or essentially free of crystals. Analyte is then applied alone (i.e., neat) to the surface of the layer, without being substantially mixed with it. The energy absorbing molecules, as do matrix, absorb the desorbing energy and cause the analyte to be desorbed. This improvement is substantial because analytes can now be presented to the energy source in a simpler and more homogeneous manner because the performance of solution mixtures and random crystallization is eliminated. This provides more uniform and predictable results that enable automation of the process. The energy absorbing material can be classical matrix material or can be matrix material whose pH has been neutralized or brought into the basic range. The energy absorbing molecules can be bound to the probe through covalent or noncovalent means.

Another version of SELDI, called SEPAR (Surface-Enhanced Photolabile Attachment and Release), involves the use of photolabile attachment molecules. A photolabile attachment molecule is a divalent molecule having one site covalently bound to a solid phase, such a flat probe surface or another solid phase, such as a bead, that can be made part of the probe, and a second site that can be covalently bound with the affinity reagent or analyte. The photolabile attachment molecule, when bound to both the surface and the analyte, also contains a photolabile bond that can release the affinity reagent or analyte upon exposure to light. The photolabile bond can be within the attachment molecule or at the site of attachment to either the analyte (or affinity reagent) or the probe surface.

b. Method for Direct Detection of Analytes

The desorbed analyte can be detected by any of several means. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them.

Alternatively, the analyte can be detectably labeled with, e.g., a fluorescent moiety or with a radioactive moiety. In these cases, the detector can be a fluorescence or radioactivity detector.

A plurality of detection means can be implemented in series to fully interrogate the analyte components and function associated with retentate at each location in the array.

c. Desorption Detectors

Desorption detectors comprise means for desorbing the analyte from the adsorbent and means for directly detecting the desorbed analyte. That is, the desorption detector detects desorbed analyte without an intermediate step of capturing the analyte in another solid phase and subjecting it to subsequent analysis. Detection of an analyte normally will involve detection of signal strength. This, in turn, reflects the quantity of analyte adsorbed to the adsorbent.

Beyond these two elements, the desorption detector also can have other elements. One such element is means to accelerate the desorbed analyte toward the detector. Another element is means for determining the time-of-flight of analyte from desorption to detection by the detector.

A preferred desorption detector is a laser desorption/ionization mass spectrometer, which is well known in the art. The mass spectrometer includes a port into which the substrate that carries the adsorbed analytes, e.g., a probe, is inserted. Desorption is accomplished by striking the analyte with energy, such as laser energy. The device can include means for translating the surface so that any spot on the array is brought into line with the laser beam. Striking the analyte with the laser results in desorption of the intact analyte into the flight tube and its ionization. The flight tube generally defines a vacuum space. Electrified plates in a portion of the vacuum tube create an electrical potential which accelerate the ionized analyte toward the detector. A clock measures the time of flight and the system electronics determines velocity of the analyte and converts this to mass. As any person skilled in the art understands, any of these elements can be combined with other elements described herein in the assembly of desorption detectors that employ various means of desorption, acceleration, detection, measurement of time, etc.

B. Selectivity Conditions

One advantage of the invention is the ability to expose the analytes to a variety of different binding and elution conditions, thereby providing both increased resolution of analytes and information about them in the form of a recognition profile. As in conventional chromatographic methods, the ability of the adsorbent to retain the analyte is directly related to the attraction or affinity of the analyte for the adsorbent as compared to the attraction or affinity of the analyte for the eluant or the eluant for the adsorbent. Some components of the sample may have no affinity for the adsorbent and therefore will not bind to the adsorbent when the sample is contacted to the adsorbent. Due to their inability to bind to the adsorbent, these components will be immediately separated from the analyte to be resolved. However, depending upon the nature of the sample and the particular adsorbent utilized, a number of different components can initially bind to the adsorbent.

1. Adsorbents

Adsorbents are the materials that bind analytes. A plurality of adsorbents can be employed in retentate chromatography. Different adsorbents can exhibit grossly different binding characteristics, somewhat different binding characteristics, or subtly different binding characteristics. Adsorbents which exhibit grossly different binding characteristics typically differ in their bases of attraction or mode of interaction. The basis of attraction is generally a function of chemical or biological molecular recognition. Bases for attraction between an adsorbent and an analyte include, for example, (1) a salt-promoted interaction, e.g., hydrophobic interactions, thiophilic interactions, and immobilized dye interactions; (2) hydrogen bonding and/or van der Waals forces interactions and charge transfer interactions, such as in the case of a hydrophilic interactions; (3) electrostatic interactions, such as an ionic charge interaction, particularly positive or negative ionic charge interactions; (4) the ability of the analyte to form coordinate covalent bonds (i.e., coordination complex formation) with a metal ion on the adsorbent; (5) enzyme-active site binding; (6) reversible covalent interactions, for example, disulfide exchange interactions; (7) glycoprotein interactions; (8) biospecific interactions; or (9) combinations of two or more of the foregoing modes of interaction. That is, the adsorbent can exhibit two or more bases of attraction, and thus be known as a "mixed functionality" adsorbent.

a. Salt-Promoted Interaction Adsorbents

Adsorbents which are useful for observing salt-promoted interactions include hydrophobic interaction adsorbents. Examples of hydrophobic interaction adsorbents include matrices having aliphatic hydrocarbons, specifically $C_1$-$C_{18}$ aliphatic hydrocarbons; and matrices having aromatic hydrocarbon functional groups such as phenyl groups. Hydrophobic interaction adsorbents bind analytes which include uncharged solvent exposed amino acid residues, and specifically amino acid residues which are commonly referred to as nonpolar, aromatic and hydrophobic amino acid residues, such as phenylalanine and tryptophan. Specific examples of analytes which will bind to a hydrophobic interaction adsorbent include lysozyme and DNA. Without wishing to be bound by a particular theory, it is believed that DNA binds to hydrophobic interaction adsorbents by the aromatic nucleotides in DNA, specifically, the purine and pyrimidine groups.

Another adsorbent useful for observing salt-promoted interactions includes thiophilic interaction adsorbents, such as for example T-GEL® which is one type of thiophilic adsorbent commercially available from Pierce, Rockford, Ill. Thiophilic interaction adsorbents bind, for example, immunoglobulins such as IgG. The mechanism of interaction between IgG and T-GEL® is not completely known, but solvent exposed trp residues are suspected to play a role.

A third adsorbent which involves salt-promoted ionic interactions and also hydrophobic interactions includes immobilized dye interaction adsorbents. Immobilized dye interaction adsorbents include matrices of immobilized dyes such as for example CIBACHRON™ blue available from Pharmacia Biotech, Piscataway, N.J. Immobilized dye interaction adsorbents bind proteins and DNA generally. One specific example of a protein which binds to an immobilized dye interaction adsorbent is bovine serum albumin (BSA).

b. Hydrophilic Interaction Adsorbents

Adsorbents which are useful for observing hydrogen bonding and/or van der Waals forces on the basis of hydrophilic interactions include surfaces comprising normal phase adsorbents such as silicon-oxide (i.e., glass). The normal phase or silicon-oxide surface, acts as a functional group. In addition, adsorbents comprising surfaces modified with hydrophilic polymers such as polyethylene glycol, dextran, agarose, or cellulose can also function as hydrophilic interaction adsorbents. Most proteins will bind hydrophilic interaction adsorbents because of a group or combination of amino acid residues (i.e., hydrophilic amino acid residues) that bind through hydrophilic interactions involving hydrogen bonding or van der Waals forces. Examples of proteins which will bind hydrophilic interaction adsorbents include myoglobin, insulin and cytochrome C.

In general, proteins with a high proportion of polar or charged amino acids will be retained on a hydrophilic surface. Alternatively, glycoproteins with surface exposed hydrophilic sugar moieties, also have high affinity for hydrophilic adsorbents.

c. Electrostatic Interaction Adsorbents

Adsorbents which are useful for observing electrostatic or ionic charge interactions include anionic adsorbents such as, for example, matrices of sulfate anions (i.e., $SO_3^-$) and matrices of carboxylate anions (i.e., $COO^-$) or phosphate anions ($OPO_3^-$). Matrices having sulfate anions are permanent negatively charged. However, matrices having carboxylate anions have a negative charge only at a pH above their pKa. At a pH below the pKa, the matrices exhibit a substantially neutral charge. Suitable anionic adsorbents also include anionic adsorbents which are matrices having a combination of sulfate and carboxylate anions and phosphate anions. The combination provides an intensity of negative charge that can be continuously varied as a function of pH. These adsorbents attract and bind proteins and macromolecules having positive charges, such as for example ribonuclease and lactoferrin. Without wishing to be bound by a particular theory, it is believed that the electrostatic interaction between an adsorbent and positively charged amino acid residues including lysine residues, arginine residues, and histidyl residues are responsible for the binding interaction.

Other adsorbents which are useful for observing electrostatic or ionic charge interactions include cationic adsorbents. Specific examples of cationic adsorbents include matrices of secondary, tertiary or quaternary amines. Quaternary amines are permanently positively charged. However, secondary and tertiary amines have charges that are pH dependent. At a pH below the pKa, secondary and tertiary amines are positively charged, and at a pH above their pKa, they are negatively charged. Suitable cationic adsorbents also include cationic adsorbents which are matrices having combinations of different secondary, tertiary, and quaternary amines. The combination provides an intensity of positive charge that can be continuously varied as a function of pH. Cationic interaction adsorbents bind anionic sites on molecules including proteins having solvent exposed amino acid residues, such as aspartic acid and glutamic acid residues.

In the case of ionic interaction adsorbents (both anionic and cationic) it is often desirable to use a mixed mode ionic adsorbent containing both anions and cations. Such adsorbents provide a continuous buffering capacity as a function of pH. The continuous buffering capacity enables the exposure of a combination of analytes to eluants having differing buffering components especially in the pH range of from 2 to 11. This results in the generation of local pH environments on the adsorbent which are defined by immobilized titratable proton exchange groups. Such systems are equivalent to the solid phase separation technique known as chromatofocusing. Follicle stimulating hormone isoforms, which differ mainly in the charged carbohydrate components are separated on a chromatofocusing adsorbent.

Still other adsorbents which are useful for observing electrostatic interactions include dipole-dipole interaction adsorbents in which the interactions are electrostatic but no formal charge or titratable proton donor or acceptor is involved.

d. Coordinate Covalent Interaction Adsorbents

Adsorbents which are useful for observing the ability to form coordinate covalent bonds with metal ions include matrices bearing, for example, divalent and trivalent metal ions. Matrices of immobilized metal ion chelators provide immobilized synthetic organic molecules that have one or more electron donor groups which form the basis of coordinate covalent interactions with transition metal ions. The primary electron donor groups functioning as immobilized metal ion chelators include oxygen, nitrogen, and sulfur. The metal ions are bound to the immobilized metal ion chelators resulting in a metal ion complex having some number of remaining sites for interaction with electron donor groups on the analyte. Suitable metal ions include in general transition metal ions such as copper, nickel, cobalt, zinc, iron, and other metal ions such as aluminum and calcium. Without wishing to be bound by any particular theory, metals ions are believed to interact selectively with specific amino acid residues in peptides, proteins, or nucleic acids. Typically, the amino acid residues involved in such interactions include histidine residues, tyrosine residues, tryptophan residues, cysteine residues, and amino acid residues having oxygen groups such as aspartic acid and glutamic acid. For example, immobilized ferric ions interact with phosphoserine, phosphotyrosine, and phosphothreonine residues on proteins. Depending on the immobilized metal ion, only those proteins with sufficient local densities of the foregoing amino acid residues will be retained by the adsorbent. Some interactions between metal ions and proteins can be so strong that the protein cannot be severed from the complex by conventional means. Human β casein, which is highly phosphorylated, binds very strongly to immobilized Fe(III).

Recombinant proteins which are expressed with a 6-Histidine tag, binds very strongly to immobilized Cu(II) and Ni(II).

e. Enzyme-Active Site Interaction Adsorbents

Adsorbents which are useful for observing enzyme-active site binding interactions include proteases (such as trypsin), phosphatases, kinases, and nucleases. The interaction is a sequence-specific interaction of the enzyme binding site on the analyte (typically a biopolymer) with the catalytic binding site on the enzyme. Enzyme binding sites of this type include, for example, active sites of trypsin interacting with proteins and peptides having lysine-lysine or lysine-arginine pairs in their sequence. More specifically, soybean trypsin inhibitor interacts with and binds to an adsorbent of immobilized trypsin. Alternatively, serine proteases are selectively retained on immobilized L-arginine adsorbent.

f. Reversible Covalent Interaction Adsorbents

Adsorbents which are useful for observing reversible covalent interactions include disulfide exchange interaction adsorbents. Disulfide exchange interaction adsorbents include adsorbents comprising immobilized sulfhydryl groups, e.g., mercaptoethanol or immobilized dithiothrietol. The interaction is based upon the formation of covalent disulfide bonds between the adsorbent and solvent exposed cysteine residues on the analyte. Such adsorbents bind proteins or peptides having cysteine residues and nucleic acids including bases modified to contain reduced sulfur compounds.

g. Glycoprotein Interaction Adsorbents

Adsorbents which are useful for observing glycoprotein interactions include glycoprotein interaction adsorbents such as adsorbents having immobilize lectins (i.e., proteins bearing oligosaccharides) therein, an example of which is CONCONAVALIN™, which is commercially available from Pharmacia Biotech of Piscataway, N.J. Such adsorbents function on the basis of the interaction involving molecular recognition of carbohydrate moieties on macromolecules. Examples of analytes which interact with and bind to glycoprotein interaction adsorbents include glycoproteins, particularly histidine-rich glycoproteins, whole cells and isolated subcellular fractions.

h. Biospecific Interaction Adsorbents

Adsorbents which are useful for observing biospecific interactions are generically termed "biospecific affinity adsorbents." Adsorption is considered biospecific if it is selective and the affinity (equilibrium dissociation constant, Kd) is at least $10^{-3}$ M to (e.g., $10^{-5}$ M, $10^{-7}$ M, $10^{-9}$ M). Examples of biospecific affinity adsorbents include any adsorbent which specifically interacts with and binds a particular biomolecule. Biospecific affinity adsorbents include for example, immobilized antibodies which bind to antigens; immobilized DNA which binds to DNA binding proteins, DNA, and RNA; immobilized substrates or inhibitors which bind to proteins and enzymes; immobilized drugs which bind to drug binding proteins; immobilized ligands which bind to receptors; immobilized receptors which bind to ligands; immobilized RNA which binds to DNA and RNA binding proteins; immobilized avidin or streptavidin which bind biotin and biotinylated molecules; immobilized phospholipid membranes and vesicles which bind lipid-binding proteins. Enzymes are useful adsorbents that can modify an analyte adsorbent thereto. Cells are useful as adsorbents. Their surfaces present complex binding characteristics. Adsorption to cells is useful for identifying, e.g., ligands or signal molecules that bind to surface receptors. Viruses or phage also are useful as adsorbents. Viruses frequently have ligands for cell surface receptors (e.g., gp120 for CD4). Also, in the form a phage display library, phage coat proteins act as agents for testing binding to targets. Biospecific interaction adsorbents rely on known specific interactions such as those described above. Other examples of biospecific interactions for which adsorbents can be utilized will be readily apparent to those skilled in the art and are contemplated by the present invention.

In one embodiment, the biospecific adsorbent can further comprise an auxiliary, or "helper", molecule that does not directly participate in binding the target analyte.

i. Degrees of Binding Specificity

By exposure to adsorbents having different modes of interaction, the components of a sample can be grossly divided based upon their interaction with the different adsorbents. Thus, the attraction of the analyte for adsorbents having different modes of interaction provides a first separation parameter. For example, by exposing a sample containing the analyte to a first adsorbent with a basis of attraction involving hydrophobicity and a second adsorbent with a basis of attraction involving ionic charge, it is possible to separate from the sample those analytes which bind to a hydrophobic adsorbent and to separate those analytes which bind to an adsorbent having the particular ionic charge.

Adsorbents having different bases of attraction provide resolution of the analyte with a low degree of specificity because the adsorbent will bind not only the analyte, but any other component in the sample which also exhibits an attraction for the adsorbent by the same basis of attraction. For example, a hydrophobic adsorbent will bind not only a hydrophobic analyte, but also any other hydrophobic components in the sample; a negatively charged adsorbent will bind not only a positively charged analyte, but also any other positively charged component in the sample; and so on.

The resolution of analytes based upon the basis of attraction of the analyte for the adsorbent can be further refined by exploiting binding characteristics of relatively intermediate specificity or altered strength of attraction. Resolution of the analyte on the basis of binding characteristics of intermediate specificity can be accomplished, for example, by utilizing mixed functionality adsorbents. Once the resolution of the analyte is accomplished with relatively low specificity, the binding characteristic found to attract the analyte of interest can be exploited in combination with a variety of other binding and elution characteristics to remove still more undesired components and thereby resolve the analyte.

For example, if the analyte binds to hydrophobic adsorbents, the analyte can be further resolved from other hydrophobic sample components by providing a mixed functionality adsorbent which exhibits as one basis of attraction a hydrophobic interaction and also exhibits a second, different basis of attraction. The mixed functionality adsorbent may exhibit hydrophobic interactions and negatively charged ionic interactions so as to bind hydrophobic analytes which are positively charged. Alternatively, the mixed functionality adsorbent can exhibit hydrophobic interactions and the ability to form coordinate covalent bonds with metal ions so as to bind hydrophobic analytes having the ability to form coordination complexes with metal ions on the adsorbent. Still further examples of adsorbents exhibiting binding characteristics of intermediate specificity will be readily apparent to those skilled in the art based upon the disclosure and examples set forth above.

The resolution of analytes on the basis of binding characteristics of intermediate specificity can be further refined by exploiting binding characteristics of relatively high specificity. Binding characteristics of relatively high specificity can be exploited by utilizing a variety of adsorbents exhibiting the same basis of attraction but a different strength of attraction. In other words, although the basis of attraction is the same, further resolution of the analyte from other sample components can be achieved by utilizing adsorbents having different degrees of affinity for the analyte.

For example, an analyte that binds an adsorbent based upon the analyte's acidic nature may be further resolved from other acidic sample components by utilizing adsorbents having affinity for analytes in specific acidic pH ranges. Thus the analyte may be resolved using one adsorbent attracted to sample components of pH 1-2, another adsorbent attracted to sample components of pH of 3-4, and a third adsorbent attracted to sample components of pH of 5-6. In this manner, an analyte having a specific affinity for an adsorbent which binds analyte of pH of 5-6 will be resolved from sample components of pH of 1-4. Adsorbents of increasing specificity can be utilized by decreasing the interval of attraction, i.e., the difference between the binding characteristics of adsorbents exhibiting the same basis of attraction.

A primary analyte adsorbed to a primary adsorbent can, itself, have adsorbent properties. In this case, the primary analyte adsorbed to a substrate can become a secondary adsorbent for isolating secondary analytes. In turn, the retained secondary analyte can function as a tertiary adsorbent to isolate a tertiary analyte from a sample. This process can continue through several iterations.

2. Eluants

The eluants, or wash solutions, selectively modify the threshold of absorption between the analyte and the adsorbent. The ability of an eluant to desorb and elute a bound analyte is a function of its elution characteristics. Different eluants can exhibit grossly different elution characteristics, somewhat different elution characteristics, or subtly different elution characteristics.

The temperature at which the eluant is contacted to the adsorbent is a function of the particular sample and adsorbents selected. Typically, the eluant is contacted to the adsorbent at a temperature of between 0° C. and 100° C., preferably between 4° C. and 37° C. However, for some eluants, modified temperatures can be desirable and will be readily determinable by those skilled in the art.

As in the case of adsorbents, eluants which exhibit grossly different elution characteristics generally differ in their basis of attraction. For example, various bases of attraction between the eluant and the analyte include charge or pH, ionic strength, water structure, concentrations of specific competitive binding reagents, surface tension, dielectric constant and combinations of two or more of the above.

a. pH-Based Eluants

Eluants which modify the selectivity of the adsorbent based upon pH (i.e., charge) include known pH buffers, acidic solutions, and basic solutions. By washing an analyte bound to a given adsorbent with a particular pH buffer, the charge can be modified and therefore the strength of the bond between the adsorbent and the analyte in the presence of the particular pH buffer can be challenged. Those analytes which are less competitive than others for the adsorbent at the pH of the eluant will be desorbed from the adsorbent and eluted, leaving bound only those analytes which bind more strongly to the adsorbent at the pH of the eluant.

b. Ionic Strength-Based Eluants

Eluants which modify the selectivity of the adsorbent with respect to ionic strength include salt solutions of various types and concentrations. The amount of salt solubilized in the eluant solution affects the ionic strength of the eluant and modifies the adsorbent binding ability correspondingly. Eluants containing a low concentration of salt provide a slight modification of the adsorbent binding ability with respect to ionic strength. Eluants containing a high concentration of salt provide a greater modification of the adsorbent binding ability with respect to ionic strength.

c. Water Structure-Based Eluants

Eluants which modify the selectivity of the adsorbent by alteration of water structure or concentration include urea and chaotropic salt solutions. Typically, urea solutions include, e.g., solutions ranging in concentration from 0.1 to 8 M. Chaotropic salts which can be used to provide eluants include sodium thiocyanate. Water structure-based eluants modify the ability of the adsorbent to bind the analyte due to alterations in hydration or bound water structure. Eluants of this type include for example, glycerol, ethylene glycol and organic solvents. Chaotropic anions increase the water solubility of nonpolar moieties thereby decreasing hydrophobic interactions between the analyte and the adsorbent.

d. Detergent-Based Eluants

Eluants which modify the selectivity of the adsorbent with respect to surface tension and analyte structure include detergents and surfactants. Suitable detergents for use as eluants include ionic and nonionic detergents such as CHAPS, TWEEN and NP-40. Detergent-based eluants modify the ability of the adsorbent to bind the analyte as the hydrophobic interactions are modified when the hydrophobic and hydrophilic groups of the detergent are introduced. Hydrophobic interactions between the analyte and the adsorbent, and within the analyte are modified and charge groups are introduced, e.g., protein denaturation with ionic detergents such as SDS.

e. Hydrophobicity-Based Eluants

Eluants which modify the selectivity of the adsorbent with respect to dielectric constant are those eluants which modify the selectivity of the adsorbent with respect to hydrophobic interaction. Examples of suitable eluants which function in this capacity include urea (0.1-8M) organic solvents such as propanol, acetonitrile, ethylene glycol and glycerol, and detergents such as those mentioned above. Use of acetonitrile as eluant is typical in reverse phase chromatography. Inclusion of ethylene glycol in the eluant is effective in eluting immunoglobulins from salt-promoted interactions with thiophilic adsorbents.

f. Combinations of Eluants

Suitable eluants can be selected from any of the foregoing categories or can be combinations of two or more of the foregoing eluants. Eluants which comprise two or more of the foregoing eluants are capable of modifying the selectivity of the adsorbent for the analyte on the basis of multiple elution characteristics.

3. Variability of Two Parameters

The ability to provide different binding characteristics by selecting different adsorbents and the ability to provide different elution characteristics by washing with different eluants permits variance of two distinct parameters each of which is capable of individually effecting the selectivity with which analytes are bound to the adsorbent. The fact that these two parameters can be varied widely assures a broad range of binding attraction and elution conditions so that the methods of the present invention can be useful for binding and thus detecting many different types of analytes.

The selection of adsorbents and eluants for use in analyzing a particular sample will depend on the nature of the sample, and the particular analyte or class of analytes to be characterized, even if the nature of the analytes are not known. Typically, it is advantageous to provide a system exhibiting a wide variety of binding characteristics and a wide variety of elution characteristics, particularly when the composition of the sample to be analyzed is unknown. By providing a system exhibiting broad ranges of selectivity characteristics, the likelihood that the analyte of interest will be retained by one or more of the adsorbents is significantly increased.

One skilled in the art of chemical or biochemical analysis is capable of determining the selectivity conditions useful for retaining a particular analyte by providing a system exhibiting a broad range of binding and elution characteristics and observing binding and elution characteristics which provide the best resolution of the analyte. Because the present invention provides for systems including broad ranges of selectivity conditions, the determination by one skilled in the art of the optimum binding and elution characteristics for a given analyte can be easily accomplished without the need for undue experimentation.

C. Analytes

The present invention permits the resolution of analytes based upon a variety of biological, chemical, or physicochemical properties of the analyte by exploiting the properties of the analyte through the use of appropriate selectivity conditions. Among the many properties of analytes which can be exploited through the use of appropriate selectivity conditions are the hydrophobic index (or measure of hydrophobic residues in the analyte), the isoelectric point (i.e., the pH at which the analyte has no charge), the hydrophobic moment (or measure of amphipathicity of an analyte or the extent of asymmetry in the distribution of polar and nonpolar residues), the lateral dipole moment (or measure of asymmetry in the distribution of charge in the analyte), a molecular structure factor (accounting for the variation in surface contour of the analyte molecule such as the distribution of bulky side chains along the backbone of the molecule), secondary structure components (e.g., helix, parallel and antiparallel sheets), disulfide bands, solvent-exposed electron donor groups (e.g., His), aromaticity (or measure of pi-pi interaction among aromatic residues in the analyte) and the linear distance between charged atoms.

These are representative examples of the types of properties which can be exploited for the resolution of a given analyte from a sample by the selection of appropriate selectivity characteristics in the methods of the present invention. Other suitable properties of analytes which can form the basis for resolution of a particular analyte from the sample will be readily known and/or determinable by those skilled in the art and are contemplated by the instant invention.

The inventive method is not limited with respect to the types of samples which can be analyzed. Samples can be in the solid, liquid, or gaseous state, although typically the sample will be in a liquid state. Solid or gaseous samples are preferably solubilized in a suitable solvent to provide a liquid sample according to techniques well within the skill of those in the art. The sample can be a biological composition, non-biological organic composition, or inorganic composition. The technique of the present invention is particularly useful for resolving analytes in a biological sample, particularly biological fluids and extracts; and for resolving analytes in non-biological organic compositions, particularly compositions of small organic and inorganic molecules.

The analytes may be molecules, multimeric molecular complexes, macromolecular assemblies, cells, subcellular organelles, viruses, molecular fragments, ions, or atoms. The analyte can be a single component of the sample or a class of structurally, chemically, biologically, or functionally related components having one or more characteristics (e.g., molecular weight, isoelectric point, ionic charge, hydrophobic/hydrophilic interaction, etc.) in common.

Specific examples of analytes which may be resolved using the retentate chromatography methods of the present invention include biological macromolecules such as peptides, proteins, enzymes, polynucleotides, oligonucleotides, nucleic acids, carbohydrates, oligosaccharides, polysaccharides; fragments of biological macromolecules set forth above, such as nucleic acid fragments, peptide fragments, and protein fragments; complexes of biological macromolecules set forth above, such as nucleic acid complexes, protein-DNA complexes, receptor-ligand complexes, enzyme-substrate, enzyme inhibitors, peptide complexes, protein complexes, carbohydrate complexes, and polysaccharide complexes; small biological molecules such as amino acids, nucleotides, nucleosides, sugars, steroids, lipids, metal ions, drugs, hormones, amides, amines, carboxylic acids, vitamins and coenzymes, alcohols, aldehydes, ketones, fatty acids, porphyrins, carotenoids, plant growth regulators, phosphate esters and nucleoside diphospho-sugars, synthetic small molecules such as pharmaceutically or therapeutically effective agents, monomers, peptide analogs, steroid analogs, inhibitors, mutagens, carcinogens, antimitotic drugs, antibiotics, ionophores, antimetabolites, amino acid analogs, antibacterial agents, transport inhibitors, surface-active agents (surfactants), mitochondrial and chloroplast function inhibitors, electron donors, carriers and acceptors, synthetic substrates for proteases, substrates for phosphatases, substrates for esterases and lipases and protein modification reagents; and synthetic polymers, oligomers, and copolymers such as polyalkylenes, polyamides, poly(meth)acrylates, polysulfones, polystyrenes, polyethers, polyvinyl ethers, polyvinyl esters, polycarbonates, polyvinyl halides, polysiloxanes, POMA, PEG, and copolymers of any two or more of the above.

III. Information Processing

Detection of analytes adsorbed to an adsorbent under particular elution conditions provides information about analytes in a sample and their chemical character. Adsorption depends, in part, upon the binding characteristics of the adsorbent: Analytes that bind to an adsorbent possess the characteristic that makes binding possible. For example, molecules that are cationic at a particular pH will bind to an anionic adsorbent under elution conditions that include that pH. Strongly cationic molecules will only be eluted from the adsorbent under very strong elution conditions. Molecules with hydrophobic regions will bind to hydrophobic adsorbents, while molecules with hydrophilic regions will bind to hydrophilic adsorbents. Again, the strength of the interaction will depend, in part, upon extent to which an analyte contains hydrophobic or hydrophilic regions. Thus, the determination that certain analytes in a sample bind to an adsorbent under certain elution conditions not only resolves analytes in a mixture by separating them from each other and from analytes that do not possess the appropriate chemical character for binding, but also identifies a class of analytes or individual analytes having the particular chemical character. Collecting information about analyte retention on one or more particular adsorbents under a variety of elution conditions provides not only detailed resolution of analytes in a mixture, but also chemical information about the analytes, themselves that can lead to their identity. This data is referred to as "retention data."

Data generated in retention assays is most easily analyzed with the use of a programmable digital computer. The computer program generally contains a readable medium that stores codes. Certain code is devoted to memory that includes the location of each feature on a substrate array, the identity of the adsorbent at that feature and the elution conditions used to wash the adsorbent. Using this information, the program can then identify the set of features on the array defining certain selectivity characteristics. The computer also contains code that receives as input, data on the strength of the signal at various molecular masses received from a particular addressable location on the probe. This data can indicate the number of analytes detected, optionally including for each analyte detected the strength of the signal and the determined molecular mass.

The computer also contains code that processes the data. This invention contemplates a variety of methods for processing the data. In one embodiment, this involves creating an analyte recognition profile. For example, data on the retention of a particular analyte identified by molecular mass can be sorted according to a particular binding characteristic, for example, binding to anionic adsorbents or hydrophobic adsorbents. This collected data provides a profile of the chemical properties of the particular analyte. Retention characteristics reflect analyte function which, in turn, reflects structure. For example, retention to coordinate covalent metal chelators can reflect the presence of histidine residues in a polypeptide analyte. Using data of the level of retention to a plurality of cationic and anionic adsorbents under elution at a variety of pH levels reveals information from which one can derive the isoelectric point of a protein. This, in turn, reflects the probable number of ionic amino acids in the protein. Accordingly, the computer can include code that transforms the binding information into structural information. Furthermore, secondary processing of the analyte (e.g., post-translational modifications) results in an altered recognition profile reflected by differences in binding or mass.

In another embodiment, retention assays are performed under the same set of selectivity thresholds on two different cell types, and the retention data from the two assays is compared. Differences in the retention maps (e.g., presence or strength of signal at any feature) indicate analytes that are differentially expressed by the two cells. This can include, for example, generating a difference map indicating the difference in signal strength between two retention assays, thereby indicating which analytes are increasingly or decreasingly retained by the adsorbent in the two assays.

The computer program also can include code that receives instructions from a programmer as input. The progressive and logical pathway for selective desorption of analytes from specified, predetermined locations in the array can be anticipated and programmed in advance.

The computer can transform the data into another format for presentation. Data analysis can include the steps of determining, e.g., signal strength as a function of feature position from the data collected, removing "outliers" (data deviating from a predetermined statistical distribution), and calculating the relative binding affinity of the analytes from the remaining data.

The resulting data can be displayed in a variety of formats. In one format, the strength of a signal is displayed on a graph as a function of molecular mass. In another format, referred to as "gel format," the strength of a signal is displayed along a linear axis intensity of darkness, resulting in an appearance similar to bands on a gel. In another format, signals reaching a certain threshold are presented as vertical lines or bars on a horizontal axis representing molecular mass. Accordingly, each bar represents an analyte detected. Data also can be presented in graphs of signal strength for an analyte grouped according to binding characteristic and/or elution characteristic.

IV. Applications of Retentate Chromatography

Retentate chromatography involves a combinatorial separation method, including detection and characterization of multiple analytes in parallel. These combinatorial methods have many applications. Such applications include, without limitation, developing target analyte detection schemes; developing protein purification strategies; protein purification methods; identifying specific phage from a phage display library that bind to a target analyte, including target epitope identification using complementary phage display libraries; protein identification based on physico-chemical properties of the analyte; gene expression monitoring and differential protein display; toxicology screening; simultaneous detection of multiple diagnostic markers; drug discovery; multimeric protein assembly monitoring and detection of in vitro polynucleotide translation.

A. Methods for Sequentially Extracting Analytes from a Sample

Retentate chromatography involves the analysis of retention of an analyte under a plurality of adsorbent/eluent conditions. One variation of this method is sequential extraction. In sequential extraction a sample is not independently exposed to two different selectivity conditions. Rather, the sample is exposed to a first selectivity condition to extract certain analytes from the sample onto the adsorbent, and leave non-adsorbed analytes in the eluent. Then, the eluent is exposed to a second selectivity condition. This further extracts various analytes from the eluent. Frequently, if the adsorbents in the first and second exposure have different basis for attraction (e.g., normal phase and hydrophobic) the adsorbent will extract a different set of analytes from the eluent. This second eluant is then exposed to a third selectivity condition, and so on. In one method of practicing sequential extraction, the adsorbent is placed at the bottom of a well so that sample can be mixed on top of it. An eluant is added to the adsorbent and after allowing binding between analytes in the sample, the eluant wash is collected. The collected wash is then exposed to a second adsorbent, and analytes are extracted from the sample by binding.

In one embodiment, the goal of sequential extraction is preparative rather than analytical. More specifically, the goal may be to extract all but a desired analyte from the sample. In this case, the sample is usually small, e.g., a few microliters on a spot about a few millimeters in diameter. The adsorbents are selected so as not to adsorb an analyte one wishes not to be depleted from the sample. After several iterations the finally collected wash is depleted of un-desired analytes, leaving the desired ones for subsequent analysis by, for example, desorption spectrometry or traditional chromatographic methods.

In another embodiment, unretained sample is, itself, analyzed for analytes by any analytic technique. Even after a single retention step, this process allows one to examine materials adsorbed to an adsorbent and those analytes that are not adsorbed.

B. Methods for Progressive Resolution of Analytes in a Sample

One object of retentate chromatography is the unambiguous resolution of an analyte from a complex sample mixture. This is especially important for applications in clinical diagnostics, drug discovery and functional genomics: These areas can involve the identification of one or more analytes from a biological sample. This invention provides a method for identifying selectivity conditions with improved resolution for an analyte. The method involves identifying a selectivity condition in which the analyte is retained and, in an iterative process, adding additional binding characteristics or elution characteristics to the selectivity condition which provide improved resolution of the analyte.

A mass spectrum of a complex sample exposed to a selectivity condition generally includes signals from many components of the sample. The complexity of the signals may interfere with unambiguous resolution of the analyte. Methods for progressive resolution of an analyte allow one to identify selectivity conditions with improved resolution of the analyte for unambiguous detection of an analyte in a sample. A selectivity condition exhibits "improved resolution" of an analyte compared with another selectivity condition if the analyte signal is more easily distinguishable from the signals of other components. This can include, for example, decreasing the number of analytes bound to the adsorbent, thereby decreasing the total number of signals, or increasing the selectivity of the selectivity condition for the analyte, thereby enhancing the analyte signal compared with other signals. Of course, when the analyte is exclusively bound to the substrate, it generates the sole analyte signal during detection.

Methods of progressive resolution involve an iterative process in which additional selectivity (binding or elution) characteristics are sequentially added to a constant set of selectivity characteristics known to retain the analyte. In a first step a series of selectivity conditions are tested to identify one that retains the target analyte. In a next step, one or more of the selectivity characteristics of the selectivity condition are selected for the constant set for further analysis.

A new set of selectivity conditions is generated. Each of the conditions in the new set includes the selected characteristics in the constant set, and at least one new condition not in the constant set. For example, if the constant set includes an anionic adsorbent and a low salt eluant, the new condition could involve varying the pH of the eluant. Each of these new variables is tested for the ability to improve the resolution of the analyte, and one modified selectivity condition with improved resolution is identified. In a next step, an added selectivity condition that provides improved resolution is added to the constant set.

The modified constant set is tested again in the same way, by generating a new set of selectivity conditions that include the characteristics of the constant set and a set of new characteristics. Thus, at each step, the selectivity conditions are selected so that resolution of the analyte is improved compared with the selectivity condition at a previous step.

The method is well described by example. A cell sample typically contains hundreds or perhaps thousands of proteins. One may wish to obtain unambiguous resolution of a single target protein analyte in the sample. In a first step, a retention map is developed for the target analyte using a plurality of selectivity conditions. For example, the adsorbents could be an anion exchanger, a cation exchanger, a normal phase adsorbent and a reverse phase adsorbent. The elution conditions tested on each adsorbent could be a variety of pH levels, a variety of ionic strengths, a variety of detergent conditions and a variety of hydrophobicity-based conditions. For example, four different elution conditions could be tested for each condition. Thus, in this example, sixteen different selectivity conditions are tested for their ability to adsorb the target analyte.

From this retention map one selects at least one selectivity condition under which the target analyte is retained. One may select a selectivity condition under which the target bound maximally. However, it may be advantageous to select a condition under which the target is not maximally bound if this selectivity condition is more selective for the target than the other selectivity conditions. Presume, for this example, that analysis of the retention map shows that the target is retained by anion exchange adsorbents at around neutral pH, but also is weakly adsorbed to a hydrophilic adsorbent.

One variable absorbent or eluant from the selectivity condition identified to result in retention of the analyte is then selected for use on all subsequent selectivity conditions. As used herein, it is said to be added to the "set of selectivity condition constants."

In the next iteration, one tests the ability of the target analyte to bind under a second plurality of selectivity conditions. Each selectivity condition at the second set includes the elements of the selectivity condition constant set. However, each selectivity also includes another variable—a different adsorbent or eluant added to the selectivity condition. Thus, within the constraint of employing at least the set of constants, the second set of selectivity conditions also are chosen to be more diverse than the first set. Methods of increasing the diversity include, for example, testing finer gradations of an elution condition or different strengths of an adsorbent. It also can include, for example, the addition of another selectivity characteristic into the selectivity conditions.

Continuing the example, the anion exchange adsorbent may be added to the set of constants. This condition is now tested with a wider variety of variables, e.g. eluants or adsorbents. Eluants to be tested can include a variety of low ph buffers at finer gradations than tested in the first iteration. For example, the first iteration may have tested buffers at pH 3.0, pH 5.0, pH 7.0 and pH 9.0, and showed that the target bound to the anion exchange adsorbent near neutral pHs. During the second iteration, the buffers tested could be at pH 5.0, pH 5.5, pH 6.0, pH 6.5, pH 7.0, pH 7.5 and pH 8.0. In addition, each of these buffers also could be varied to include other elution characteristics, e.g., ionic strength, hydrophobicity, etc.

Analysis of the second retention map resulting at this stage generally will allow one to identify a condition that provided better resolution than the selectivity condition identified in the first round. Again, one of the variables of this selectivity condition is chosen and added to the set of selectivity condition constants for further interrogation in the next iteration.

Continuing the example, suppose the selectivity condition in the second round that resolves the analyte best uses a buffer at pH 6.5. This eluant can now be added to the set of constants, which now includes an anion exchange resin and a pH 6.5 buffer. In the next iteration, the selectivity conditions include this constant set, and another variable. The variable might be, for example, addition of a new component to the eluant, such as different ionic strengths; or another adsorbent can be added into the mixture, such as variety of hydrophobic adsorbents mixed with the anion exchange adsorbent; or one may vary the density of the anion exchange resin. Again, a selectivity condition is identified from this set that shows improved resolution of the analyte.

The process can continue until the analyte is purified to essential homogeneity. In this case, the selectivity condition is specific for the analyte.

As one can see, by increasing the number of variables tested at each step, one can decrease the number of iterations needed to identify a suitable selectivity condition.

C. Methods of Preparative Purification of an Analyte

In another aspect, this invention provides methods of purifying an analyte. The methods take advantage of the power of retentate chromatography to rapidly identify bases of attraction for adsorbing an analyte. A first step involves exposing the analyte to a plurality of selectivity conditions and determining retention under the conditions by retentate chromatography. This generates a recognition profile characteristic of the analyte. The selectivity conditions under which the analyte is retained are used to develop a protocol for preparative purification of the analyte.

For preparative purification of the analyte, the analyte is sequentially adsorbed and eluted from a series of adsorbent/eluant combinations that were identified as binding the analyte. Thus, for example, the recognition map may indicate that the analyte binds to a normal phase adsorbent and to a metal chelator. The analyte is then contacted with a first chromatography column, for example, containing the normal phase adsorbent, which binds the analyte. Unbound material is washed off. Then the analyte is eluted by a sufficiently stringent wash. The eluant is then contacted with a metal chelate column, for example, to bind the analyte. Unbound materials are washed away. Then, the bound material that includes the analyte, is eluted from the metal chelate column. In this way, the analyte is isolated in preparative amounts. A preparative amount of a sample is at least 10 µl, at least 100 µl, at least 1 ml or at least 10 ml.

The information generated during progressive resolution of analytes can be used to design larger scale chromatographic (elution-based) protein purification strategies. The adsorbent bases for attraction, the binding conditions, and the elution conditions (i.e., the selectivity conditions) for a target analyte protein become defined by retentate chromatography. This information can save an enormous amount of time, energy, and precious analyte that would otherwise be wasted during the trial and error process of purification strategy design that is now in place. This section also provides for large scale purification efforts performed with commercially available adsorbents.

D. Methods for Making Probes for Specific Detection of Analytes

This invention provides probes for the specific detection of one or more analytes by desorption spectrometry, as well as methods for generating these probes. Such analyte-resolving probes are useful the specific detection of analytes in diagnostic and analytic methods.

The first step in generating a probe for resolving one or more analytes is to produce a retention map for the analytes under a plurality of different adsorbent/eluant combinations. For example, the resolution of the analytes can be determined for four different adsorbents washed with each of five different eluants. This provides twenty sets of retention data for each of the analytes. Analysis of the resulting retention map will indicate which selectivity condition or conditions best resolves the analytes. Preferably, one selectivity condition can be identified that unambiguously resolves all the analytes. Then, one or more selectivity conditions is selected for use in the analyte-resolving probe so that each of the analytes is resolved on at least adsorbent spot. The probe also could contain an adsorbent that does not bind the analyte or analytes. This adsorbent spot is useful as a control. The probes can include a plurality of adsorbent spots in addressable locations selected for their ability to retain and resolve the analyte or analyte. In this case, adsorbents are selected that bind the analyte under a single eluant condition. This is useful because the entire probe can be washed with a single eluant in the detection process.

The retention map generated for a particular analyte can be used create a customized adsorbent for the analyte. For example, the nature of the adsorbents that retain an analyte indicate a set of bases for attraction of an analyte. A customized adsorbent can be designed by preparing a multiplex adsorbent that includes elements of adsorbents that provide these bases for attraction. Such a custom adsorbent is very selective for the target analyte. One or a few custom adsorbents can suffice to generate a recognition map for the analyte. For example, if it is found that under particular elution conditions an analyte is retained by adsorbents that bind materials that have certain degrees of hydrophobicity, positive charge and aromaticity, one can create a custom adsorbent by design or through the use of combinatorial synthetic strategies having functional groups that attract each of these three characteristics. Detecting binding to this adsorbent identifies the analyte.

Such probes are useful for detecting the analyte or analytes in a sample. The sample is exposed to the selectivity conditions and the probe is interrogated by desorption spectrometry. Because the probe resolves the analytes, their presence can be detected by looking for the characteristic recognition profile. Such probes are particularly useful for identifying a set of diagnostic markers in a patient sample.

In one embodiment, the array is designed to dock specific classes of protein of interest. This includes diagnostic markers as well as analytes defined by function. For example, an array can be prepared that specifically docks cell surface proteins, enzymes of a certain class (e.g., kinases), transcription factors, intracellular receptors, etc. The adsorbents can be specific for the biopolymers, for example, antibodies.

In one embodiment, the adsorbents are genetic packages such as phage displaying protein ligands for a certain class of proteins. In this case, a phage display library can be pre-screened with a certain class of molecules to eliminate phage that bind to that class. Then, phage that have been subtracted from the population are used as adsorbents.

E. Diagnostic Probes and Methods of Diagnosis

Diagnosis of pathological conditions frequently involves the detection in a patient sample of one or more molecular markers of disease. Certain conditions can be diagnosed by the presence of a single diagnostic marker. Diagnosis of other conditions may involve detection of a plurality diagnostic markers. Furthermore, the detection of several markers may increase the confidence of diagnosis. Accordingly, this invention provides probes for desorption spectrometry comprising at least one adsorbent that resolves at least one diagnostic marker of a pathological condition.

The preparation of such probes involves, first, the selection of markers to be detected. The marker can be a marker for any disease state, e.g., cancer, heart disease, autoimmune disease, viral infection, Alzheimer's disease or diabetes. For example, detection of prostate specific antigen (PSA) is highly suggestive of prostate cancer. HIV infection can be diagnosed by detecting antibodies against several HIV proteins, such as one of p17, p24 or p55 and one of p31, p51 or p66 and one of gp41 or gp120/160. Detection of amyloid β42 and tau protein in cerebrospinal fluid is highly indicative of Alzheimer's disease. Also, the markers can be identified by methods of this invention involving detecting differential presence of an analyte in healthy subjects versus subjects with pathological conditions.

In a next step, adsorbents are developed that retain one or more diagnostic markers. Preferably, a single adsorbent is prepared that resolves all the markers. This can be accomplished, for example, by creating a spot containing several antibodies, each of which binds one of the desired markers. Alternatively, the probe can comprise a plurality of adsorbent spots, each spot capable of resolving at least one target analyte under a selectivity condition. In one embodiment, the adsorbent is a multiplex adsorbent comprising ligands that are specific for the markers. For example, the adsorbent can comprise an antibody, a polypeptide ligand or a polynucleotide that specifically binds the target analyte. In one embodiment, the antibody is a single chain antibody identified by screening a combinatorial library. Single chain antibodies that are specific for particular markers can be developed by screening phage display libraries by methods described herein.

In another embodiment, the adsorbent comprises non-organic biomolecular components that either retain the target analyte specifically or that retain the analyte with sufficient specificity for unambiguous resolution by desorption spectrometry. Preparation of adsorbents for detection of specific analytes also are described herein.

Significantly, a single adsorbent spot used in these methods need not be specific for a single analyte and, therefore, need not require biopolymer-mediated specific affinity between target and adsorbent. Prior affinity detection methods have relied mainly on specific binding between a biopolymer and a target. This includes, for example, the specific affinity of an antibody for a protein, a polynucleotide for a complementary polynucleotide or a lectin for a carbohydrate. Such specificity was necessary because these means of detection were indirect: the target was not identified; a label, frequently bound to the adsorbent, was identified. Accordingly, the more specific the adsorbent, the less likelihood that contaminants would bind to the adsorbent and interfere with specific detection. However, desorption spectrometry results in direct detection of an analyte. Accordingly, the presence of contaminants does not interfere with specific detection unless the signal of the contaminant overlaps with the signal of the target.

Methods of diagnosis involve, first, selecting a patient sample to be tested. The sample can be, e.g., tissue, blood, urine, stool or other bodily fluid (lymph, cerebrospinal, interarticular, etc.). Then, the sample is exposed to a substrate containing the diagnostic adsorbents under conditions to allow retention of the diagnostic markers. The adsorbent is washed with an appropriate eluant. Then the markers are detected (e.g., resolved) by desorption spectrometry (e.g., mass spectrometry).

This invention also provides kits for specific detection of diagnostic markers including (1) a substrate for use in desorption spectrometry that comprises at least one adsorbent in at least one addressable location that resolves at least one diagnostic marker under a selectivity condition that comprises the adsorbent and an eluant and (2) the eluant or instructions for preparation of the eluant. Upon exposing the sample to the adsorbent and washing with the eluant, i.e., by executing the selectivity condition, the analyte is sufficiently purified or specifically bound for resolution by desorption spectrometry.

F. Methods for Identifying Proteins

In another aspect, this invention provides a method for aiding in the identification of a protein. The method involves determining match parameters for physico-chemical characteristics of a protein analyte using retentate chromatography and searching a protein database to identify proteins having the match parameters. The derivation of physico-chemical information based on retention characteristics is discussed above. The database typically will provide the amino acid sequence and/or the nucleotide sequence encoding the amino acid sequence of each protein. Structural characteristics, such as molecular mass, hydrophobicity, pI, fragment mass, etc. are easily derivable from this information. An analyte protein will share any particular structural characteristic with only a subset of the proteins in the database. Accordingly, identity candidates are found by sorting the proteins according to structural characteristics shared with the protein analyte. Thus, in view of the inaccuracy, degree of specificity, or level of confidence inherent in identifying one or more physicochemical properties of the reference, one cannot expect that proteins in the database will perfectly match all the characteristics of the reference. Accordingly, the match parameters can be set to identify, for example, the closeness of fit between the protein analyte characteristics and the characteristics of the reference polypeptides in the database.

As our identification of genes in the genome increases, the chance that any protein analyte exists in the database as a reference polypeptide also increases. Accordingly, this method enables one to rapidly resolve a protein of interest in a sample, obtain structural information about the protein, and then use this information to identify the protein.

G. Methods for Assembling Multimeric Molecules

The ability of adsorbents to dock desired molecules is useful in building multimeric molecules and assessing compounds that effect their assembly. A unit of the multimeric molecule is bound to an adsorbent. Then it is exposed to a sample that contains another unit of the multimeric molecule. Expose can be performed under a variety of conditions to test binding parameters. The binding of a subunit to the multimer can be monitored by desorption spectrometry. Then, a subsequent subunit can be tested for binding in the same way. The drug screening methods described herein are useful for testing agents for the ability to interfere with assembly. Accordingly, an analyte at one stage of the process becomes an adsorbent at the next stage.

H. Methods for Performing Enzyme Assays

This invention also provides methods for performing enzyme assays. Enzyme assays generally involve exposing a sample to be tested with an enzyme substrate under conditions under which the enzyme is active. After allowing the enzyme to act on the substrate, a product of the enzymatic reaction is detected. In quantitative assays, the amount of product is determined. This amount usually is compared to a control or a standard curve, thereby yielding an amount of enzyme activity in the sample.

This invention provides methods for detecting an enzyme, including detecting an amount of enzyme activity, in a sample. The method takes advantage of the fact that the activity of an enzyme often produces a product whose mass is different than the original substrate. In the method, a solid phase is prepared that comprises an adsorbent that binds the substrate. An amount of the substrate is bound to the adsorbent. Then the adsorbent is exposed to the sample under conditions and for a time that allows any enzyme to act on the substrate. Then, any bound material is detected by desorption spectrometry. Detection of an analyte having a molecular mass characteristic of the product of enzyme activity provides an indication of the presence of the enzyme. The signal strength will be a function of the amount of enzymatic activity in the sample.

I. Methods for Identifying Analytes that are Differentially Expressed Between Biological Materials In another aspect this invention provides methods for identifying organic biomolecules, particularly proteins, that are differentially expressed between two or more samples. "Differential expression" refers to differences in the quantity or quality of an analyte between two samples. Such differences could result at any stage of protein expression from transcription through post-translational modification. The methods take advantage of the extraordinary resolving power and sensitivity of retentate chromatography. First, recognition profiles using the same set of selectivity conditions are prepared for analytes from the two biological samples. The greater the number of selectivity conditions used, the greater the resolution of analytes in the sample and, therefore, the greater the number of analytes that can be compared. Then, the recognition maps are compared to identify analytes that are differentially retained by the two sets of adsorbents. Differential retention includes quantitative retention. This indicates, e.g., up- or down-regulation of expression. Differential retention also includes qualitative differences in the analyte. For example, differences in post-translational modification of a protein can result in differences in recognition maps detectable as differences in binding characteristics (for example, if the protein is glycosylated, it will bind differently to lectin adsorbents) or differences in mass (for example, as a result of differences in post-translational cleavage). The analysis can be carried out by a programmable, digital computer.

The method is particularly useful to detect genes that are differentially expressed between two cell types. The two cell types could be normal versus pathologic cells, e.g., cancer cells or cells at different levels or cells at different stages of development or differentiation, or in different parts of the cell cycle. However, the method also is useful in examining two cells of the same type exposed to different conditions. For example, the method is useful in toxicology screening and testing agents for the ability to modulate gene expression in a cell. In such a method, one biological sample is exposed to the test agent, and other cell is not. Then, retentate maps of the samples are compared. This method may indicate that a protein or other biomolecule is increased or decreased in expression, or is changed some way based on different retention characteristics or different mass.

Using information about the physico-chemical properties of differentially expressed proteins obtained from the retention maps, identity candidates for these proteins can be determined using methods described herein.

This method is useful for identifying diagnostic markers of disease. Proteins that are differentially expressed in a patient sample or a diseased cultured cell compared to normal samples or cells may be diagnostic markers. In general, it is best to compare samples from a statistically significant patient population with normal samples. In this way, information can be pooled to identify diagnostic markers common to all or a significant number of individuals exhibiting the pathology.

1. Increasing Sensitivity by Catabolic Signal Amplification

The sensitivity of detecting differential presence (e.g, resulting from differential expression) of large proteins in a complex mixture can be increased significantly by fragmenting the large protein into smaller pieces and detecting the smaller pieces. Increased sensitivity is due to several factors. First, when all the proteins in a sample are fragmented by, for example, enzymatic digestion, large proteins are likely to produce more fragments than small proteins. Second, the overall sensitivity of desorption spectrometry is greater at lower molecular masses than higher molecular masses. Third, fragmenting a protein increases the number of signals from that target, thereby increasing the likelihood of detecting that target. Fourth, fragmenting a protein increases the likelihood of capturing and, therefore, detecting, at least one fragment of the protein. Fifth, if a protein is differentially present in two samples, then by increasing the number of signals from that protein, the difference in amount is more likely to be detected.

Also, the method is counter-intuitive. Generally, one seeks to decrease the complexity of an analyte mixture before analysis. Fragmentation increases the complexity.

Accordingly, in one embodiment of this invention the sensitivity of detecting an analyte is increased by converting the analyte into lower molecular mass fragments before detection. Fragmentation can be achieved by any means known in the art. For example, protein analytes can be fragmented using endoproteases. Carbohydrate analytes can be fragmented using glycosidases. Nucleic acids can be fragmented using endonucleases. The sample can be subject to fragmentation before or after docking with the adsorbent.

J. Methods for Identifying Ligands for a Receptor

Functional pathways in biological systems frequently involve the interaction between a receptor and a ligand. For example, the binding between transcriptional activation frequently involves the prior binding of a ligand with a transcription factor. Many pathological conditions involve abnormal interaction between a receptor and its ligand. Interruption of the binding between a receptor and a ligand is a frequent target of drug discovery. However, the identity of a ligand for a receptor frequently is unknown; the receptor is an "orphan" receptor.

This invention provides a method using retentate chromatography to identify ligands for receptors. The method involves docking a receptor to an adsorbent. Then, a sample that is suspected of containing a ligand for the receptor is exposed to the docked receptor under an elution condition appropriate for binding between the receptor and the ligand. Then, ligands that have bound to the receptor are detected by desorption spectrometry. The power of this method derives, in part, from the sensitivity to desorption spectrometry to detect small quantities of material docked to an adsorbent.

Docking the receptor to the adsorbent requires identifying an adsorbent that retains, and preferably, specifically binds, the receptor. Methods for identifying adsorbents that specifically bind a protein are described herein. In one method, the adsorbent comprises an antibody specific for the receptor. In another embodiment, the receptor is produced as recombinant fusion protein that includes a moiety for specific binding. For example, the receptor can be fused with the Fc portion of an antibody. Such portions bind to protein A which can be incorporated into an adsorbent.

The sample tested for the presence of a ligand is at the discretion of the practitioner. For example, if the receptor is a nuclear receptor, the sample can be nuclear extract. If the receptor is a cytoplasmic receptor, the sample can be cytoplasmic extract. If the receptor is a cell surface receptor, the sample can be fluid from the surface to which the cell is exposed, for example, serum for an epithelial cell surface receptor.

The sample generally will be incubated with the receptor under physiological conditions for a time sufficient to allow binding, for example 37° C. for several hours. Then, unbound material is washed away. This method can quickly identify ligands that conventional techniques require months to identify.

Retentate chromatography allows parallel processing of samples on several adsorbent spots. Accordingly, this method can involve testing a plurality of different samples for the presence of a ligand, as well as the testing of a single sample under a plurality of incubation and elution conditions.

By determining the mass of the identified ligand and various physico-chemical properties, the ligand can be positively identified using information from genome databases.

In another embodiment of this method a set of probes is prepared which has been exposed to and has docked proteins from a cell. This probe is useful, itself, as a secondary probe to identify molecules from the cell that bind to the docked molecules. After preparing a retentate map from the probe, the probe is secondarily exposed to the test material, generally under less stringent conditions than those used to prepare the secondary probe, and the addressable locations analysed. Molecules that are newly docked to the probe are those bound to the already-docked molecules.

K. Methods for Drug Discovery

Identifying molecules that intervene in the binding between a receptor and its ligand is an important step in developing drugs. This invention provides methods of screening compounds for their ability to modulate the binding between an adsorbent and an analyte (e.g., a receptor adsorbent and a ligand analyte) by exposing an adsorbent and analyte to a test compound, and detecting binding between the adsorbent and the analyte by desorption spectrometry.

Rapid screening of combinatorial libraries for drug candidates requires the ability to expose target interactions to thousands of drugs and identify agents that interfere with or promote the interaction. Retentate chromatography enables one to dock one member of a ligand/receptor pair to a substrate and to use it as a secondary adsorbent. Then, after exposing the member to its partner and to the agent, one can determine by desorption spectrometry whether and to what extent the partner has bound. Advantages of retentate chromatography in screening methods include the ability to specifically dock the receptor to a substrate through an adsorbent, the ability to rapidly deploy the receptor on many adsorbent spots for parallel processing, and the speed of throughput that is possible by reading results through desorption spectrometry.

1. Screening Assay

The method involves providing an adsorbent; contacting the adsorbent with the target analyte in the presence and absence of the agent under one or more selectivity conditions and determining whether the amount of binding with and without the agent. The amount of binding is determined by retentate chromatography (e.g., by preparing a recognition profile). The experiment can be carried out with a control in which no agent is added, or a control in which a different amount or type of agent is added and the zero amount is determined by extrapolation. A statistically significant difference in the amount of binding ($p<0.05$) indicates that the test agent modulates binding.

This method is particularly useful to screen analytes (e.g., proteins) as drug target candidates. After development of the protein retention map or recognition profile from serum or some other target cell type, the agent is exposed to the array of retained analyte at their addressable locations. After binding is allowed, unbound agent is eluted or washed away. Those analytes that retained bound agent under the selectivity conditions specified are identified directly by desorption mass spectrometry, because the agent itself appears as a new component in the retention map (i.e, the agent is desorbed and detected directly). This method is particularly useful to screen drug candidates, both agonists and antagonists, for their ability to bind analytes or modulate one or more biological processes.

2. Receptor and Ligand

The adsorbent and the target analyte need not engage in specific binding. However, in particularly useful methods the adsorbent and the target analyte are a ligand/receptor pair.

In one embodiment, the ligand/receptor pair are a hormone and a cell surface receptor or an intracellular receptor. The adsorbent can be an entire cell or cell membrane in the case of a membrane-bound receptor. A protein receptor or other drug target candidate may be used as an adsorbent to screen combinatorial drug libraries. Hundreds or thousands of drug candidates can be applied to a single receptor type or addressable location. After removal of unbound and weakly bound drug candidates (i.e., agents) the bound agents are detected and identified by desorption spectrometry.

In another embodiment, the adsorbent is an enzyme that binds and modifies the target substrate. The agents are screened for their ability to modulate enzymatic transformation of the analyte. For example, enzymatic activity can be detected because the recognition profile of an analyte may differ from that of the product of enzyme activity. Differential retention indicates that the agent alters binding.

The receptor/receptor can be retained on the substrate in a variety of ways. In one method, the receptor/ligand is directly retained by a non-specific adsorbent. In another method, the adsorbent is specific for the receptor/ligand. For example, the adsorbent can contain an antibody specific for the receptor/ligand. The receptor/ligand can be a fusion protein in which the fusion moiety specifically binds the adsorbent, for example, in the manner that an Fc fragment binds protein A. In one method, a genetic package, such as a phage from a phage display library, that has on its surface a polypeptide that specifically binds the receptor/ligand, is bound to the substrate. The ligand is captured by the polypeptide. Also, the adsorbent can be an analyte already docked to the substrate, i.e., it can be a secondary adsorbent, a tertiary adsorbent, etc.

This invention provides a particularly useful method to evaluate both the direct and indirect consequences of drug (or other agent) binding to a target. The detection of one or more analytes in a retentate map generated from the proteins of a target cell type may be altered due to the action of the agent (e.g., drug candidate) on 1) the target binding protein itself, 2) some other analyte (not the drug binding protein), or 3) on gene expression (up or down regulation). It is the high resolving and information generating power of retentate chromatography to detect these changes, i.e., drug induced differences in the generic retentate map or recognition profile observed with and without drug, that makes this method one of the most powerful tools available for proteomics, functional genomics, drug discovery, therapeutic drug monitoring, and clinical diagnostics.

3. Test Agents

A test agent that is to be screened for its ability to modulate prothymosin expression is administered to the test animal or to the cultured cells in vitro. The choice of the agent to be tested is left to the discretion of the practitioner. However, because of their variety and ease of administration as pharmaceuticals, small molecules are preferred as test agents.

a. Chemistry

The agent to be tested can be selected from a number of sources. For example, combinatorial libraries of molecules are available for screening. Using such libraries, thousands of molecules can be screened for regulatory activity. In one preferred embodiment, high throughput screening methods involve providing a library containing a large number of potential therapeutic compounds (candidate compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.,* 37: 487493, Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries, peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

L. Methods for Generating Agents that Specifically Bind an Analyte

This invention provides methods for generating agents, e.g., single chain antibodies, that specifically bind to a target analyte. These agents are useful, e.g., as specific diagnostic agents for docking targets in the study of ligand/receptor interactions. The method is particularly useful for generating agents against targets that may only be isolated in such small quantities that it is not possible or practical to generate antibodies by immunizing an animal. The method involves the steps of providing a substrate having a target attached thereto; providing a display library of genetic packages that display agents to be screened; exposing the library to the target to specifically retain genetic packages through interaction with the target and detecting retained genetic packages by desorption spectrometry.

These steps can be conducted in parallel for a large number of adsorbent-analyte candidates within complex populations without transfer losses and ambiguities associated with separate selection and detection procedures, including off-line amplification and labeling strategies associated with indirect detection means.

1. Providing the Substrate

The first step of the method involves providing a substrate that comprises an adsorbent that will serve as a target for a polypeptide agent of a display library to be screened. In one embodiment, the substrate is provided with the target adsorbent already attached. In another embodiment, the substrate is provided by providing a substrate that has an adsorbent that binds a target analyte, exposing the adsorbent to the analyte under elution conditions to allow retention of the analyte, and using the target adsorbent as the target for the display library. In one embodiment, the target is differentially expressed between two cell types that are being compared. For example, the targets may be derived from differentially expressed mRNA or may be differentially expressed polypeptides. Methods of identifying such differentially expressed proteins by retentate chromatography methods are described above.

Once a differentially expressed protein analyte is identified, one can develop a selectivity condition that unambiguously resolves the analyte. More preferably, retention of the analyte is specific or exclusive. The methods for progressive resolution of analytes described above make it possible to identify selectivity conditions that specifically bind a target analyte from a complex sample. In one embodiment, the bound target can be modified, e.g., by exposure to an enzyme.

Alternatively, the method can begin at the mRNA or EST stage. In this method, differentially expressed mRNAs or ESTs are identified by routine methods. Then, these molecules are transcribed and translated in vitro and in situ on an adsorbent for docking. For example, a substrate for desorption spectrometry having a plurality of adsorbent spots is prepared. The substrate is overlaid with a cylindrical tube, thereby creating a well with the adsorbent at the base of the well. In the well one places reagents for in vitro transcription and translation of the differentially expressed mRNA (usually in the form of cDNA). (For methods see, e.g., Sambrook et al., *Molecular Cloning—A Laboratory Manual,* Cold Spring Harbor Laboratory, Cold Spring Harbor, N.Y., (1989) and *Current Protocols in Molecular Biology,* F. M. Ausubel et al., eds., (Current Protocols, a joint venture between Greene Publishing Associates, Inc. and John Wiley & Sons, Inc.)) Translation of the mRNA or EST produces a polypeptide that is adsorbed. The cylindrical tube is removed and the adsorbent spots are washed with an eluant, so as to identify a selectivity condition that retains the polypeptide analyte.

2. Providing the Display Library

The second step involves providing a display library. The display library is comprised of genetic packages that display on their surfaces any sort of combinatorial library of peptides ("polypeptide agents"). However, single chain antibodies are attractive because they can be used in subsequent immunoassays.

Many kinds of display libraries and their uses are known in the art. A basic concept of display methods is the establishment of a physical association between a polypeptide ligand to be screened and a recoverable polynucleotide that encodes the polypeptide. This physical association is provided by a multimeric molecular complex, in this case the genetic package, e.g., the phage particle, which displays a polypeptide as part of a capsid enclosing the phage genome which encodes the polypeptide. The establishment of a physical association between polypeptides and their genetic material allows simultaneous mass screening of very large numbers of genetic packages bearing different polypeptides. Genetic packages displaying a polypeptide with affinity to a target bind to the target and these packages are enriched by affinity screening to the target. The identity of polypeptides displayed from these packages can be determined from their respective genomes. Using these methods a polypeptide identified as having a binding affinity for a desired target can then be synthesized in bulk by conventional means.

The genetic packages most frequently used for display libraries are bacteriophage, particularly filamentous phage, and especially phage M13, Fd and F1. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). See, also Cwirla et al., *Proc. Natl. Acad. Sci.* USA 87, 6378-6382 (1990); Devlin et al., *Science* 249, 404-406 (1990), Scott & Smith, *Science* 249, 386-388 (1990); Ladner et al., U.S. Pat. No. 5,223,409 and Ladner et al. U.S. Pat. No. 5,571,698. Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. Display of antibody fragments on the surface of viruses which infect bacteria (bacteriophage or phage) makes it possible to produce human sFvs with a wide range of affinities and kinetic characteristics.

In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wild-type copies of coat protein expressed from the helper phage. See, e.g., Garrard, WO 92/09690.

Eukaryotic viruses can be used to display polypeptides in an analogous manner. For example, display of human heregulin fused to gp70 of Moloney murine leukemia virus has been reported by Han et al., *Proc. Natl. Acad. Sci. USA* 92, 9747-9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan et al., *J. Mol. Biol.* 196, 1-10 (1987).

Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer-surface proteins are discussed by Ladner et al., U.S. Pat. No. 5,571,698, and Georgiou et al., *Nature Biotechnology* 15, 29-34 (1997) and references cited therein. For example, the lamB protein of *E. coli* is suitable.

3. Screening the Display Library

The third step involves screening the display library to identify a ligand that specifically binds the target. The substrate bearing the target is exposed to the display library that displays polypeptide agents under elution conditions appropriate for specific binding between the polypeptide and a target molecule. Genetic packages that have agents that recognize the target bind to the target already attached to the substrate. Removing unbound particles and retention of bound particles results from exposure to the elution condition.

A population of genetic packages, in this case M13 phage, representing approximately $10^{11}$ plaque forming units (pfu) per mL are introduced to a substrate with an addressable array of bound target adsorbents (e.g., protein). Upon contact, a selectivity condition optimized for the target adsorbent (i.e., selectivity threshold modifier or eluent) is chosen, such that only a small subset of total phage genotypes are selectively retained, preferably fewer than 5-10. Note that unbound phage (i.e., phage not bound to the target adsorbent) and phage loosely bound to the target adsorbent are eliminated by exposure to eluents that disrupt all but the most selective analyte-target adsorbent interaction(s). Those phage displaying polypeptides with the highest affinity for the target adsorbent are selectively retained.

4. Detecting Bound Genetic Packages Containing Agents that Specifically Bind the Target In the fourth step, the binding of genetic packages to the target is detected by desorption spectrometry. For example, the M13 phage has thousands of copies of a single coat protein. Upon striking the phage with a laser in desorption spectrometry, the coat proteins become dislodged and are detectable. In this way, one can determine whether the library contained a phage having an agent that bound to the target. In order to have genetic packages for subsequent analysis, the screening step can be performed in parallel at different locations on a probe, or the substrate can have a physical dimension sufficiently large so that the laser does not dislodge all the genetic packages bound to the surface. This method is particularly powerful, because even a few phage bound to the analyte can be detected.

In the case of M13, the preferred detection method is to monitor, by desorption spectrometry, the appearance of the gene VIII coat protein as a "marker" protein signal. In this manner, we have detected "positive" target adsorbents with as few as 5 phage particles (pfu) bound (phage particle number estimated by calculation from known dilutions). Other phage markers, in order of preference, include gene V, gene X, and gene III (including their fusion products).

After detection of those adsorbent locations with the highest affinity adsorbents, that is, those locations within the array with the fewest phage retained after exposure to high selectivity conditions (i.e., stringent eluents), the bound package can now be used as a jump-off point for other uses.

5. Isolating the Genetic Package

In one embodiment, the method further involves isolating the genetic package for further analysis. This analysis can involve reproducing the genetic package and isolating the polynucleotide from it. The isolated phage are reproduced by the usual methods. For example, the retained phage can be exposed to a biological amplification vehicle, for example, E. coli, plus nutritive media to grow the genetic packages for subsequent analysis. Single clones can be further tested for ability to bind to analyte retained on substrate.

6. Sequencing the Nucleotide Sequence Encoding the Polypeptide Agent

Sequencing the nucleotide sequence encoding the polypeptide agent of a bound genetic package provides information for producing the polypeptide agent. Sequencing can involve isolating the genetic package from the adsorbent, reproducing it, isolating the polynucleotide, and sequencing the nucleotide sequence by any available means. In another method, the genetic packages can be reproduced in situ by contacting the substrate with appropriate materials, such as cells subject to infection by the genetic package. In another embodiment, sequencing is performed in situ. The method can involve lysing the genetic packages and amplifying the nucleotide sequence by any known means, e.g., PCR. Several different genetic packages may have bound to different epitopes available on the surface. In this case, one may alter the elution conditions so that only one kind of phage binds to an epitope.

7. Producing the Polypeptide Agent

One valuable next step involves producing the polypeptide agent. The isolated agent can be used, e.g., as an adsorbent for specific detection of the target in diagnostics or for the study of ligand/receptor interactions.

In one method, producing the polypeptide involves first sequencing the nucleotide sequence that encodes the polypeptide. The amino acid sequence can be derived from the nucleotide sequence. Sequencing can be accomplished by the method as described above. The sequence can be the basis for recombinant or chemical synthesis of the polypeptide agent.

In another method, the polypeptide can be produced by reproducing the genetic package. This is particularly effective when the genetic package contains many copies of the polypeptide agent. The genetic package can be reproduced in situ or after isolation.

A method of producing the polypeptide recombinantly can proceed as follows. The nucleotide sequence encoding the polypeptide is either sequenced or isolated by any means such as those discussed. Then, the nucleotide sequence is included in an expression vector. The expression vector contains an expression control sequence operatively linked to the nucleotide sequence encoding the polypeptide. The expression vector can then be used to express the polypeptide agent recombinantly by means well known in the art.

It is understood that the target can contain more than one epitope. Accordingly, the method can produce more than one polypeptide agent specific for the target.

Target-specific agents can then be used as adsorbents for probes used in clinical diagnostics or drug discovery. That is, because such probes contain on their surface agents that specifically bind the target, they can be used to isolate the target from complex mixtures, such as biological samples, and to detect the target by desorption spectrometry. Furthermore, because the interaction between the agent and the target can be biospecific, it is likely to involve a greater affinity between the two than an adsorbent developed by the progressive resolution method, described above.

8. Isolating Peptide Epitopes of a Target

In one version this method allows one to isolate peptide epitopes of a target analyte. The method employs an "anti-idiotypic"-like approach. In summary, the epitopes of a target analyte are screened with, e.g., a phage display library. The isolated phage contain, e.g., single chain antibodies that recognize the epitopes of the analyte. These phage are used, in turn, to screen a second display library. The phage from the second library that bind to the single chain antibodies of the first contain displayed polypeptides that mimic the structure of the epitope recognized by the single chain antibodies.

In one embodiment of this method, a nucleotide sequence encoding a polypeptide agent that binds the target analyte is used to produce M13 phage in which the agent is displayed as a fusion with gene VIII. Thus, this phage has a coat with hundreds of copies of the target peptide on its surface. This phage is then docked to the adsorbent. Docking can be accomplished through, e.g., a ligand that binds gene III, or gene III can be modified to include a receptor for a ligand on the substrate. The phage is then exposed to a second display library. Genetic packages from the library that bind to the docked phage are detected and isolated as described. Preferably, the second display library contains a mass label of some sort so that their gene VIII protein can be distinguished from gene VIII of the phage docked to the substrate. Thus, the identification of a substance as an "analyte target" or as an adsorbent can depend upon whether the bound substance is used, subsequently, to bind another substance. As one can see, the ability to bind a substance to an already docked substance can continue, as can methods of identifying conditions that selectively remove the terminally bonded substance.

EXAMPLES

The following examples are offered by way of illustration, not by way of limitation.

In the following examples, the following products and terms are employed. Chicken egg white lysozyme (1 µl diluted to 10 picomole/µl water), is available from Sigma Chemical Company, St. Louis, Mo. "Human serum" refers to a composition of 1 µl of human serum diluted 1 to 5 in 20 mM sodium phosphate buffer, 0.5 M NaCl, pH 7.0.

As used herein, "mg" means milligram(s); "ml" means milliliter(s); "µl" means microliter(s); "cm" means centimeter(s); "nm" means nanometer(s); "M" means molar; "mM" means millimolar; "min" means minute(s); "%" or "percent" is percent by weight unless otherwise specified; "NaCl" means sodium chloride; "TFA" means trifluoroacetic acid.

I. Protocols for Retentate Chromatography

The following protocols are examples of procedures for performing retentate chromatography.

A. Protocol for Retentate Mapping (using Chromatographic Series Array)

1. Sample Treatment

Dilute the biological sample (e.g., serum, urine, cell extract or cell culture medium) in 0.01% Triton X100 in HEPES or 20 mM Na phosphate, pH 7.2. Centrifuge to clarify sample if necessary.

2. Sample Application

Add sample (1-5 µl) to a spot of Anionic, Normal phase or TED-Cu(II) adsorbent array. For a hydrophobic adsorbent array prewet each spot with 0.5 µl acetonitrile containing 0.5% TFA. Add sample to the spot before the acetonitrile is dry.

Allow sample to concentrate (almost to dryness) on the spot.

3. Washing a. Anionic Adsorbent Array

Wash spot 1 with 20 mM HEPES or Na phosphate, pH 7.2. Add the first 2 µl of wash solution to the spot before the sample is completely dry. Let the wash solution sit on the spot for at least 15 sec. Pipet out and in 10 times. Remove the first wash completely, repeat with the second wash of 2 µl of the solution.

Wash spot 2 with 0.2 M NaCl in 20 mM Na phosphate, pH 7.2 as above.

Wash spot 3 with 1 M NaCl in 20 mM Na phosphate, pH 7.2 as above.

Wash spot 4 with 20 mM Tris HCl, pH 8.5 as above.

Wash spot 5 with 0.1 M Na acetate, pH 4.5 as above.

Wash spot 6 with 0.05% Triton X100 in 20 mM HEPES or Na phosphate, pH 7.2 as above.

Wash spot 7 with 3 M urea in 20 mM HEPES or Na phosphate, pH 7.2 as above.

Wash spot 8 with 10% acetonitrile in water as above.

Wash the whole array with water thoroughly.

Air dry the chip.

Add 0.3 µl Energy Absorbing Molecule (saturated solution prepared in 50% acetonitrile, 0.5% trifluoroacetic acid).

Air dry the chip.

Analyze the retained protein on each spot with laser desorption/ionization time-of-flight mass spectrometer.

b. Normal Phase Adsorbent Array

Wash spot 1 with 5 mM HEPES, pH 7. Add the first 2 µl of wash solution to the spot before the sample is completely dry. Let the wash solution sit on the spot for at least 15 sec. Pipet out and in 10 times. Remove the first wash completely, repeat with the second wash of 2 µl of the solution.

Wash spot 2 with 20 mM Na phosphate, 0.15 M NaCl, pH 7.2 as above.

Wash spot 3 with 20 mM Na phosphate, 0.5 M NaCl, pH 7.2 as above.

Wash spot 4 with 0.1 M Na acetate, pH 4.0 as above.

Wash spot 5 with 0.05% Triton X100 in 20 mM Na phosphate, 0.15 M NaCl, pH 7.2 as above.

Wash spot 6 with 3 M urea in 20 mM Na phosphate, 0.15 M NaCl, pH 7.2 as above.

Wash spot 7 with 1% TFA as above.

Wash spot 8 with 30% isopropanol:acetonitrile (1:2) in water as above.

Wash the whole array with water thoroughly.

Air dry the chip.

Add 0.3 µl Energy Absorbing Molecule (saturated solution prepared in 50% acetonitrile, 0.5% trifluoroacetic acid).

Air dry the chip.

Analyze the retained protein on each spot with laser desorption/ionization time-of-flight mass spectrometer.

c. TED-Cu(II) Adsorbent Array

Wash spot 1 with 20 mM Na phosphate, 0.5 M NaCl, pH 7.2. Add the first 2/1 of wash solution to the spot before the sample is completely dry. Let the wash solution sit on the spot for at least 15 sec. Pipet out and in 10 times. Remove the first wash completely, repeat with the second wash of 2 µl of the solution.

Wash spot 2 with 20 mM imidazole in 20 mM Na phosphate, 0.5 M NaCl, pH 7.2 as above.

Wash spot 3 with 100 mM imidazole in 20 mM Na phosphate, 0.5 M NaCl, pH 7.2 as above.

Wash spot 4 with 0.1 M Na acetate, 0.5 M NaCl, pH 4.0 as above.

Wash spot 5 with 0.05% Triton X100 in 20 mM Na phosphate, 0.15 M NaCl, pH 7.2 as above.

Wash spot 6 with 3 M urea in 20 mM Na phosphate, 0.15 M NaCl, pH 7.2 as above.

Wash spot 7 with 1% TFA as above.

Wash spot 8 with 10% acetonitrile in water as above.

Wash the whole array with water thoroughly.

Air dry the chip.

Add 0.3 M Energy Absorbing Molecule (saturated solution prepared in 50% acetonitrile, 0.5% trifluoroacetic acid).

Air dry the chip.

Analyze the retained protein on each spot with laser desorption/ionization time-of-flight mass spectrometer.

d. Hydrophobic Adsorbent Array

Wash spot 1 with 5% acetonitrile in 0.1% TFA. Add the first 2 µl of wash solution to the spot before the sample is completely dry. Let the wash solution sit on the spot for at least 15 sec. Pipet out and in 10 times. Remove the first wash completely, repeat with the second wash of 2 µl of the solution.

Wash spot 2 with 50% acetonitrile in 0.1% TFA as above.

Wash spot 3 with 0.05% Triton X100 in 20 mM Na phosphate, 0.15 M NaCl, pH 7.2 as above.

Wash spot 4 with 3M urea in 20 mM Na phosphate, 0.15 M NaCl, pH 7.2 as above.

Wash the whole array with water thoroughly.

Air dry the chip.

Add 0.3 µl Energy Absorbing Molecule (saturated solution prepared in 50% acetonitrile, 0.5% trifluoroacetic acid).

Air dry the chip.

Analyze the retained protein on each spot with laser desorption/ionization time-of-flight mass spectrometer.

B. Protocol for Antibody-Antigen Assay; Receptor-Ligand Assay (using Pre-Activated Adsorbent Array)

1. Immobilization of Antibody on Pre-activated Adsorbent Array

Place a pre-activated adsorbent array on a flat clean surface. Spot the antibody or receptor or control solution onto each spot of a pre-activated adsorbent array prewetted with 0.5 µl of isopropanol (add 1 µl antibody/spot before the isopropanol is dry).

Incubate (4° C. or room temperature, 2-18 h) in a humid chamber.

Use pipet to remove remaining solution from the spots.

Block residual active sites on the spots by adding 1 ml of 1 M ethanolamine, pH 7.4 in PBS over the entire chip and incubate in a humid chamber (room temperature 30 min).

Wash the chip twice with 1% Triton X-100 in PBS. Submerge the chip in about 9 ml of wash solution in a 15 ml conical plastic tube and rock on benchtop agitator for at least 15 minutes.

Wash with 0.5 M NaCl in 0.1 M sodium acetate, pH 4.0 as above.

Wash with 0.5 M NaCl in 0.1 M Tris HCl, pH 8.0 as above.

Rinse with PBS as above. Then cover the chip with PBS and store at 4° C. until ready to use.

2. Binding of Antigen or Ligand

Gently shake or blot off PBS on the chip.

Add 1-5 µl of sample to each spot. For samples with very low antigen or ligand concentration, put the adsorbent array into a bioprocessor. Wash the spots on the chip and Bioprocessor wells with 200 µl PBS two times. Add up to 300 µl of sample to each well.

Seal with adhesive tape.

Incubate with shaking (4° C. or room temperature, 1-18 h).

3. Washing

Remove sample from the spots, wash each spot with 2 µl of 0.1% Triton X100 in PBS, pH 7.2, two times. Add the first 2 µl of wash solution to the spot. Let the wash solution sit on the spot for at least 15 sec. Pipet out and in 10 times. Remove the first wash completely, repeat with the second wash of 2 µl of the solution. This is followed by a wash with 0.5 M NaCl in 0.1 M HEPES, pH 7.4.

Wash the whole array with water thoroughly.

4. Analysis of Retained Proteins

Air dry the chip.

Add 0.3 µl Energy Absorbing Molecule. (saturated solution of Sinapinic Acid or EAMI or CHCA prepared in 50% acetonitrile, 0.5% trifluoroacetic acid).

Air dry the chip.

Analyze the retained protein on each spot with laser desorption/ionization time-of-flight mass spectrometer.

II. Recognition Profile of Lysozyme

We generated a recognition profile for lysozyme using high-information resolution retentate chromatography. The profile includes resolution of lysozyme with six adsorbents, each under a variety of different selectivity threshold modifiers. The result is 40 different spectrographs that differently characterize the physico-chemical properties of lysozyme.

A. Lysozyme Recognition Profile Using a Hydrophilic Adsorbent Array

Chicken egg white lysozyme is added to various spots of a chromatographic series adsorbent array of a silicon oxide adsorbent on a stainless steel substrate. After incubation in a moist chamber at room temperature for 15 min., each different spot of adsorbent is washed with one of the following eluants (selectivity threshold modifiers):

(1) 20 mM sodium phosphate buffer, pH 7.0,
(2) 0.2 M NaCl in 20 mM sodium phosphate buffer, pH 7.0,
(3) 0.4 M NaCl in 20 mM sodium phosphate buffer, pH 7.0,
(4) 25 mM sodium acetate buffer, 0.125 M NaCl, pH 4.5,
(5) 1% TFA,
(6) 10% acetonitrile in water,
(7) 20% acetonitrile in water,
(8) 0.05% Tween20 in 20 mM sodium phosphate buffer, 0.15 M NaCl, pH 7.0, and
(9) 3M urea in 20 mM sodium phosphate buffer, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer, using a nitrogen laser (355 nm) and a 60 cm flight tube. The data is analyzed by computer and exported to GRAMS/32c (available from Galactic Industries Corporation) for data overlay presentation.

Figure 5A:
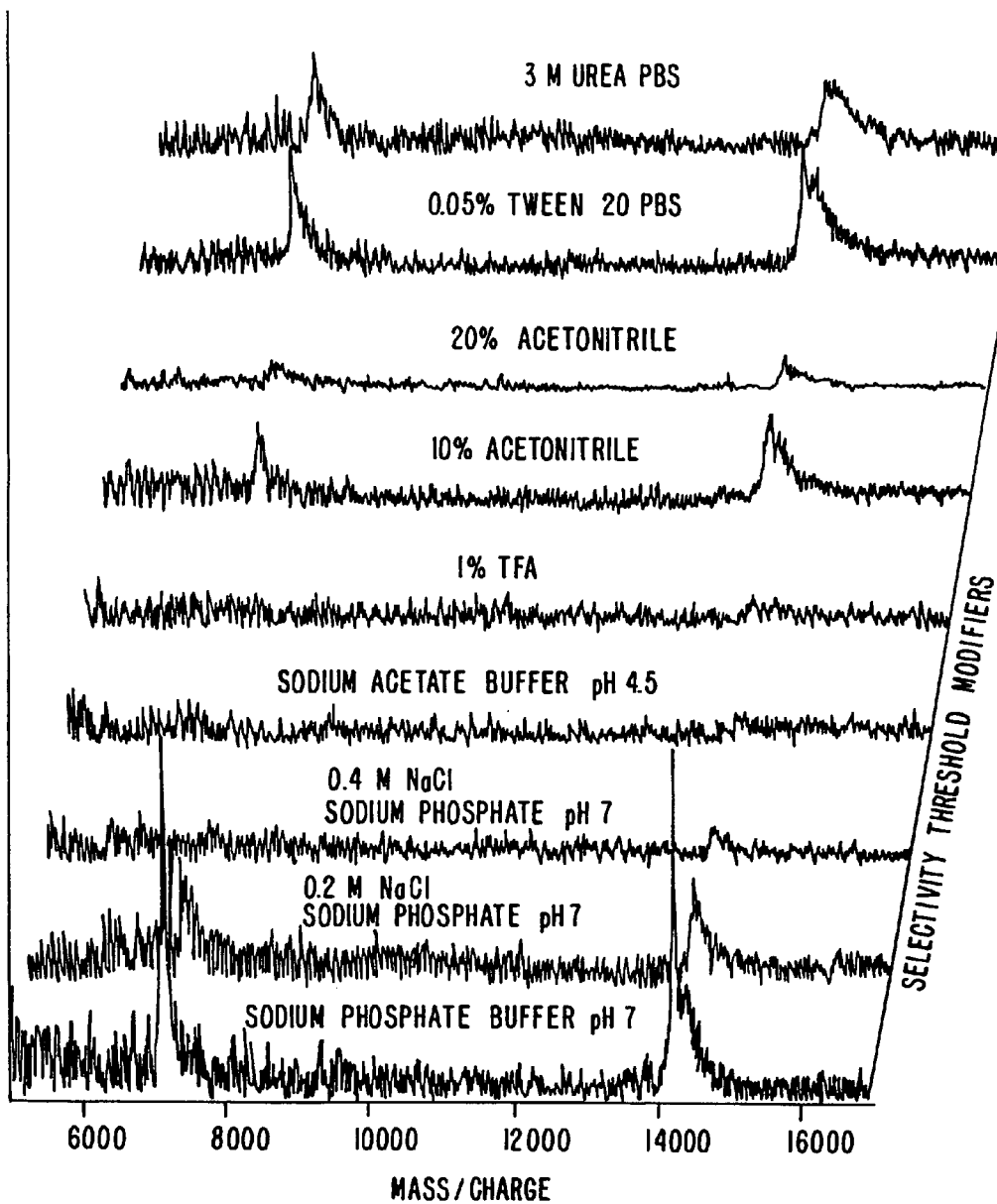
FIGS. 5A-5F show retention maps for lysozyme under selectivity conditions including six different adsorbents and several different eluants.

FIG. 5A shows the composite mass spectrum of a lysozyme recognition profile on a normal phase chromatographic series adsorbent array. The bottom profile shows the lysozyme signal intensity retained on the silicon oxide adsorbent after washing with pH 7 buffer alone. Inclusion of sodium chloride (0.2-0.4 M) in the selectivity threshold modifier decreases the retention of lysozyme. This indicates that the interaction of lysozyme (a basic protein) with a silicon oxide (negatively charged at pH 7) adsorbent involves an ion exchange mechanism. Lowering the pH of the selectivity threshold modifier, for example to pH 4.5 in the sodium acetate buffer, or <2 in 1% TFA, almost completely eliminates the negative charge on the silicon oxide adsorbent, and lysozyme is not retained any longer. Including polarity modulating agents, (e.g., organic solvents (e.g., acetonitrile), or detergent (e.g., Tween20), or urea in the selectivity threshold modifier also reduces the interaction of lysozyme with the silicon oxide adsorbent. This indicates that the other interaction mechanism involves a hydrophilic interaction.

B. Lysozyme Recognition Profile Using a Hydrophobic Adsorbent Array Chicken egg white lysozyme is added to various spots of a chromatographic series adsorbent array of polypropylene ($C_3$ hydrophobic) adsorbent coated on silicon oxide-coated stainless steel substrate. After incubation in a moist chamber at room temperature for 15 min., each different spot of adsorbent is washed with one of the following eluants (selectivity threshold modifiers):

(1) 0.1% TFA,
(2) 10% acetonitrile in 0.1% TFA,
(3) 20% acetonitrile in 0.1% TFA,
(4) 50% acetonitrile in 0.1% TFA,
(5) 0.05% Tween20 in 20 mM sodium phosphate buffer, 0.15 M NaCl, pH 7.0, and
(6) 3M urea in 20 mM sodium phosphate buffer, 0.15 M NaCl, pH 7.0.

Each wash includes pipetting 1 µl of wash solution in and out of the spot of adsorbent three times. This process is repeated with a fresh aliquot of wash solution. Afterwards, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 5B:
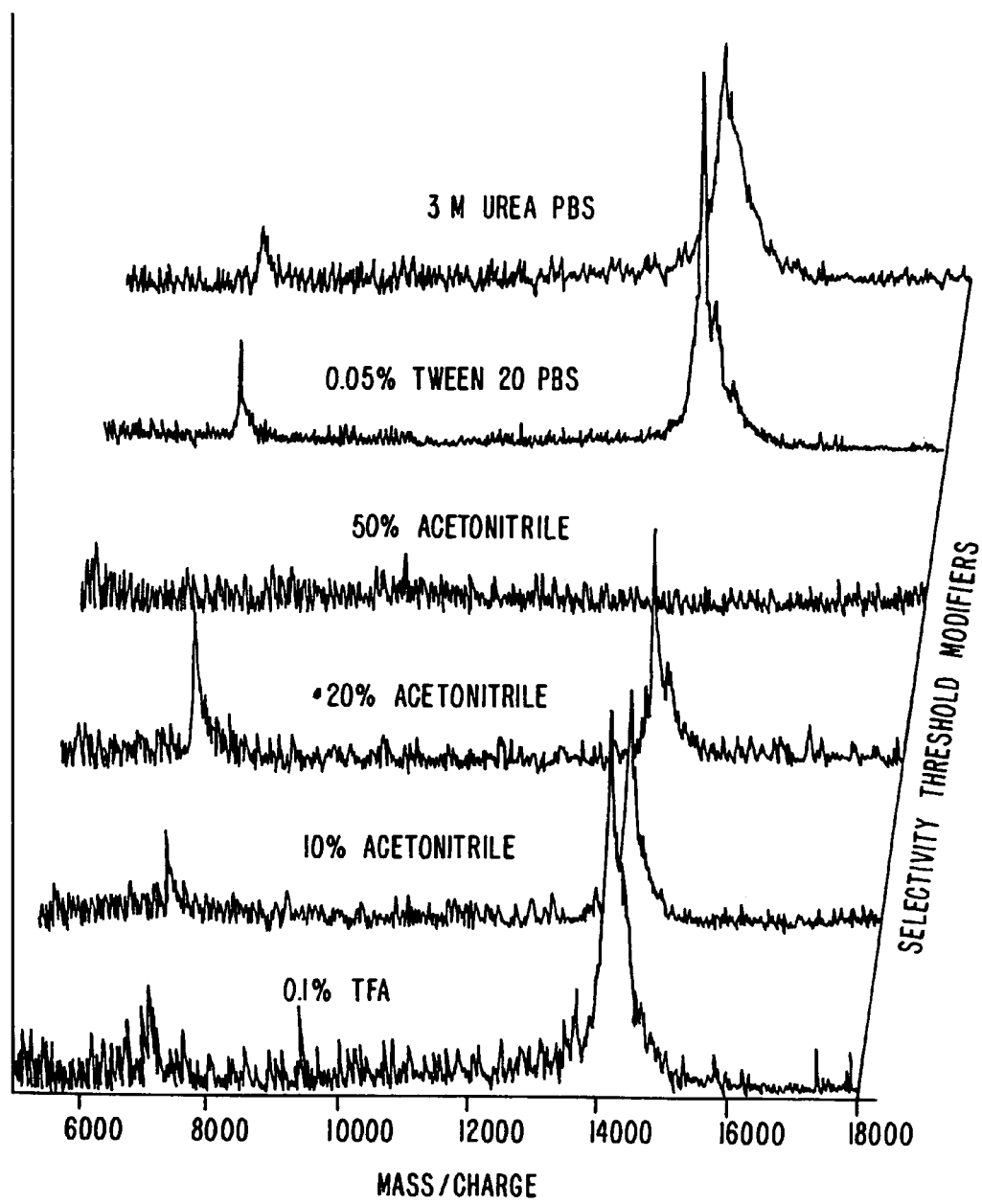

FIG. 5B shows the composite mass spectrum of lysozyme recognition profile on a hydrophobic $C_3$ chromatographic series adsorbent array. The bottom profile shows the lysozyme signal intensity retained on the hydrophobic $C_3$ adsorbent after washing with 0.1% TFA alone. Including a polarity modulating agent, (e.g., acetonitrile) in the selectivity threshold modifier decreases the retention of lysozyme on the hydrophobic $C_3$ adsorbent. The acetonitrile concentration range for elution of lysozyme from the hydrophobic $C_3$ adsorbent is between 20-50%. Including detergent (Tween20), or urea, in the selectivity threshold modifier does not significantly reduce the retention of lysozyme on the hydrophobic $C_3$ adsorbent.

C. Lysozyme Recognition Profile Using a Phenyl Hydrophobic Adsorbent Array

Chicken egg white lysozyme is added to various spots of an adsorbent array of polystyrene (phenyl hydrophobic)

adsorbent coated on silicon oxide-coated stainless steel substrate. After incubation in a moist chamber at room temperature for 15 min., one spot of adsorbent is washed with one of the following eluants (selectivity threshold modifiers):
(1) 0.1% TFA,
(2) 10% acetonitrile in 0.1% TFA,
(3) 20% acetonitrile in 0.1% TFA,
(4) 50% acetonitrile in 0.1% TFA,
(5) 0.05% Tween20 in 20 mM sodium phosphate buffer, 0.15 M NaCl, pH 7.0, and
(6) 3M urea in 20 mM sodium phosphate buffer, 0.15 M NaCl, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 5C:
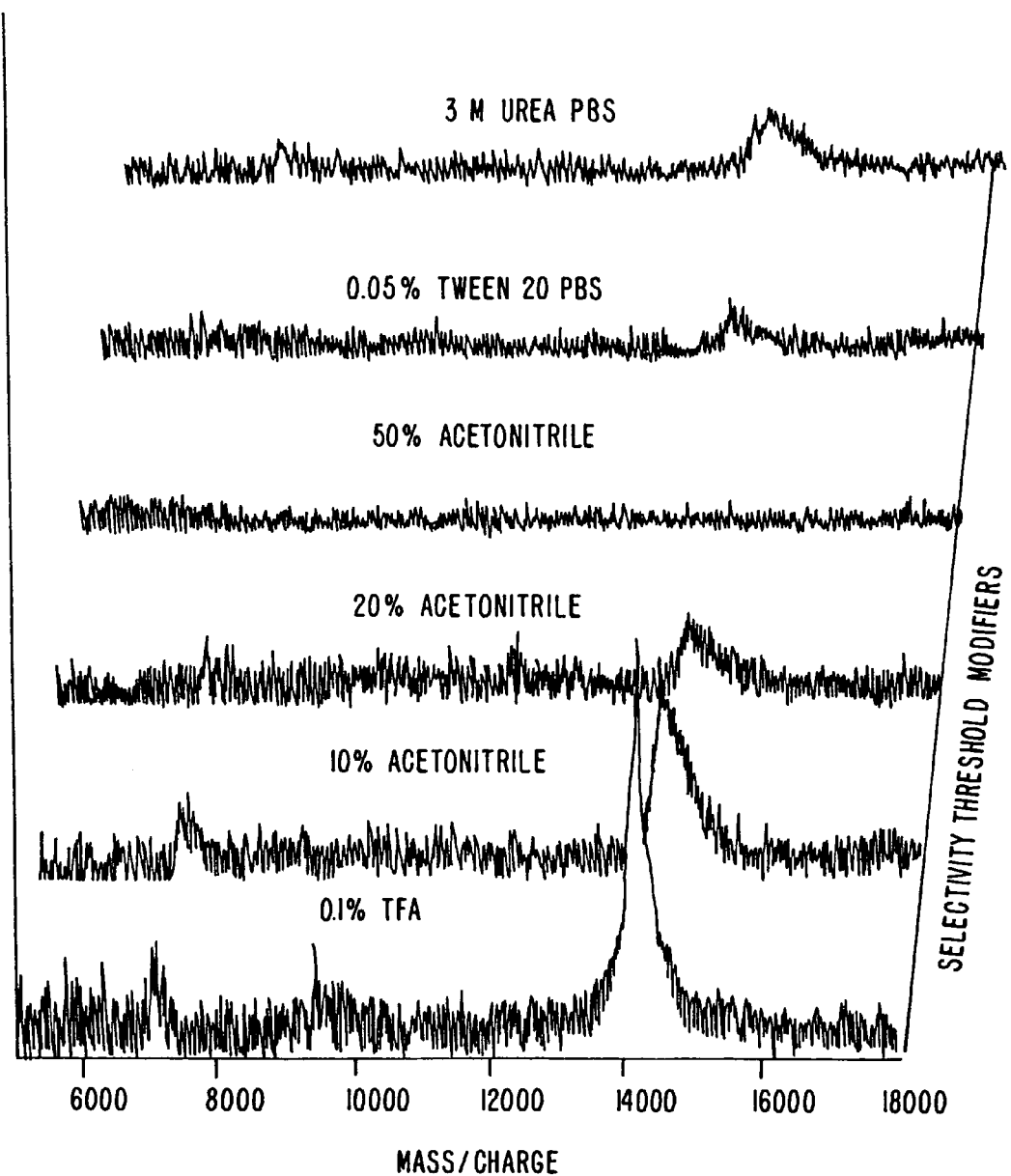

FIG. 5C shows the composite mass spectrum of the lysozyme recognition profile on the hydrophobic phenyl chromatographic series adsorbent array. The bottom profile shows the lysozyme signal intensity retained on the hydrophobic phenyl adsorbent after washing with 0.1% TFA alone. Including a polarity modulating agent, (e.g., acetonitrile) in the selectivity threshold modifier decreases the retention of lysozyme. The acetonitrile concentration range for elution of lysozyme from the hydrophobic $C_3$ adsorbent is between 20-50%, however, when the lysozyme peak intensities retained on the $C_3$ and phenyl surface are compared under the same 20% acetonitrile wash condition, the interaction of lysozyme with the phenyl adsorbent is less strong. Including detergent (e.g., Tween20), or urea, in the selectivity threshold modifier also significantly reduces the retention of lysozyme on the hydrophobic phenyl adsorbent.

D. Lysozyme Recognition Profile Using an Anionic Adsorbent Array

Chicken egg white lysozyme is added to various spots of an adsorbent array of anionic group ($SO_3^-$) adsorbent (i.e., a cationic exchange adsorbent) coated on silicon oxide-coated stainless steel substrate. After incubation in a moist chamber at room temperature for 15 min., each different spot of adsorbent is washed with one of the following eluants (selectivity threshold modifiers):
(1) 20 mM sodium phosphate buffer, pH 7.0,
(2) 0.1 M NaCl in 20 mM sodium phosphate buffer, pH 7.0,
(3) 0.2 M NaCl in 20 mM sodium phosphate buffer, pH 7.0,
(4) 0.4 M NaCl in 20 mM sodium phosphate buffer, pH 7.0,
(5) 25 mM sodium acetate buffer, 0.125 M NaCl, pH 4.5,
(6) 0.05% Tween20 in 20 mM sodium phosphate buffer, 0.15 M NaCl, pH 7.0, and
(7) 3M urea in 20 mM sodium phosphate buffer, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 5D:
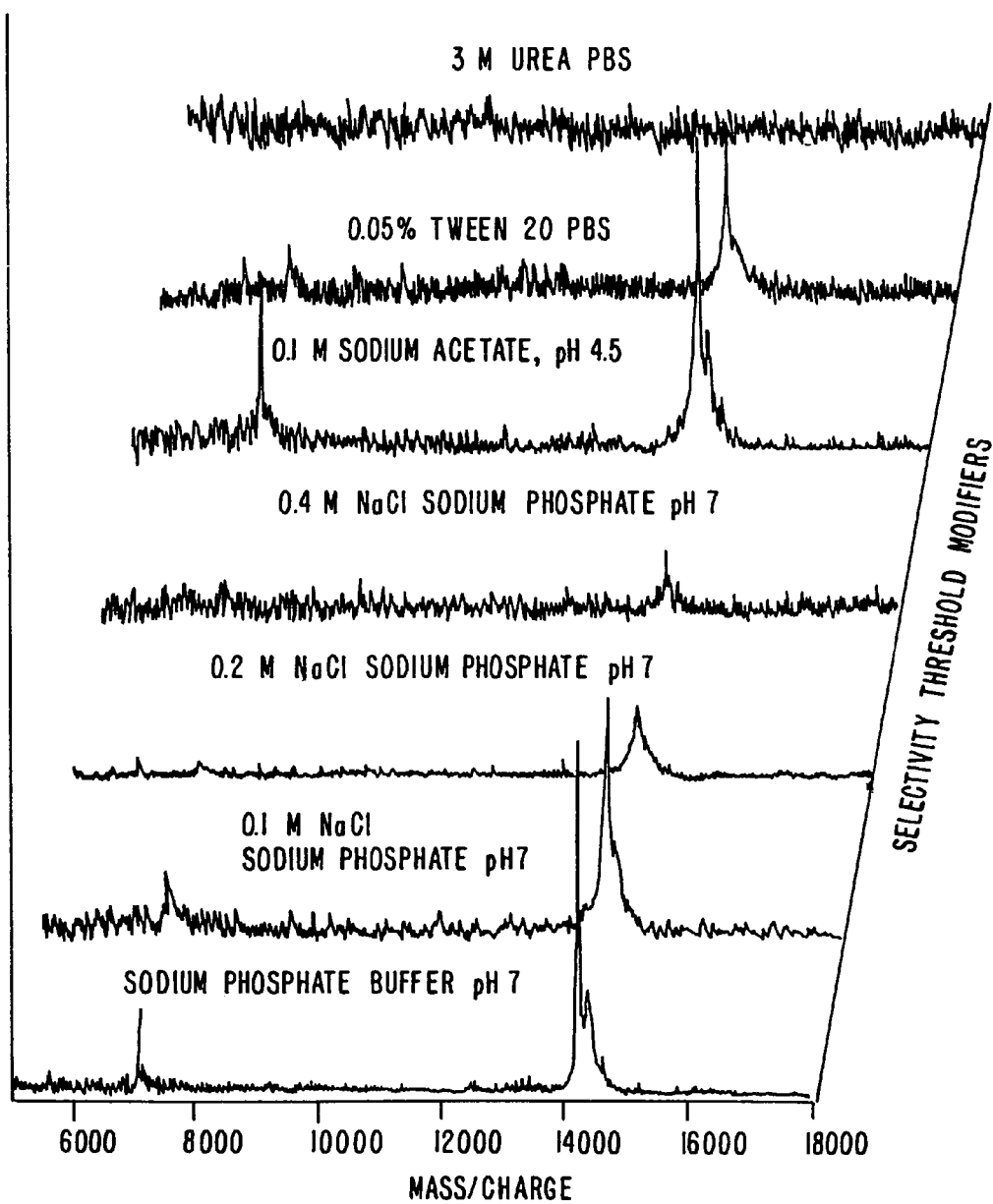

FIG. 5D shows the composite mass spectrum of the lysozyme recognition profile on a cation exchange chromatographic series array. The bottom profile shows the lysozyme signal intensity retained on the anionic adsorbent after washing with pH 7 buffer alone. Including increasing concentrations of sodium chloride (0.1-0.4 M) in the selectivity threshold modifier decreases the retention of lysozyme. This indicates that the interaction of lysozyme (a basic protein) with the anionic adsorbent involves an ion exchange mechanism. A 0.4 M NaCl concentration is required to elute the lysozyme. Lowering the pH of the selectivity threshold modifier to pH 4.5 in the sodium acetate buffer, does not affect the retention of lysozyme on a strong anionic adsorbent. Including a polarity modulating agent (e.g., a detergent such as Tween20, or urea) in the selectivity threshold modifier reduces the interaction of lysozyme with an anionic adsorbent. This indicates that the interaction of a hydrophobic lysozyme protein with the anionic adsorbent is modulated by the polarity of the eluant.

E. Lysozyme Recognition Profile Using an Cationic Adsorbent Array

Chicken egg white lysozyme is added to various spots of an adsorbent array of cationic (quaternary amine) adsorbent coated on silicon oxide-coated stainless steel substrate. After incubation in a moist chamber at room temperature for 15 min., each different spot of adsorbent is washed with one of the following eluants (selectivity threshold modifiers):
(1) 20 mM sodium phosphate buffer, pH 7.0,
(2) 0.1 M NaCl in 20 mM sodium phosphate buffer, pH 7.0,
(3) 0.2 M NaCl in 20 mM sodium phosphate buffer, pH 7.0,
(4) 0.4 M NaCl in 20 mM sodium phosphate buffer, pH 7.0,
(5) 25 mM sodium acetate buffer, 0.125 M NaCl, pH 4.5,
(6) 0.05% Tween20 in 20 mM sodium phosphate buffer, 0.15 M NaCl, pH 7.0, or
(7) 3M urea in 20 mM sodium phosphate buffer, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 5E:
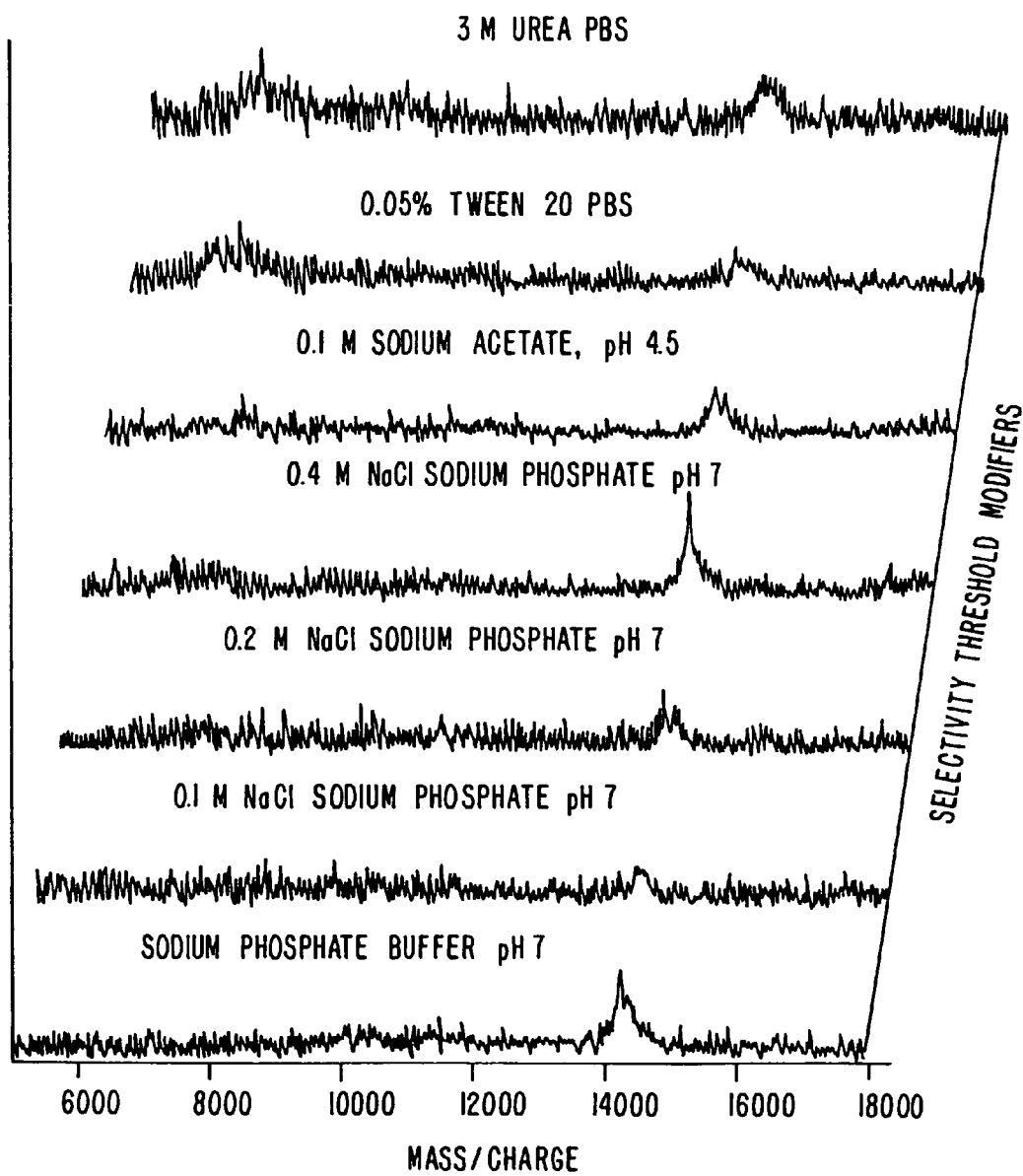

FIG. 5E shows the composite mass spectrum of the lysozyme recognition profile on the cationic (anion exchange) adsorbent chromatographic series adsorbent array. The retention of the basic lysozyme protein on the cationic adsorbent is very weak. The effect of modulating the selectivity threshold modifiers on lysozyme retention is minimal.

F. Lysozyme Recognition Profile Using an Immobilized Metal Ion Adsorbent Array

Chicken egg white lysozyme is added to various spots of an adsorbent array of immobilized metal (iminodiacetate-Cu) adsorbent coated on silicon oxide-coated stainless steel substrate. After incubation in a moist chamber at room temperature for 15 min., each different spot of adsorbent is washed with one of the following eluants (selectivity threshold modifiers):
(1) 20 mM sodium phosphate buffer, 0.5 M NaCl, pH 7.0,
(2) 5 mM imidazole in 20 mM sodium phosphate buffer, 0.5 M NaCl, pH 7.0,
(3) 0.1 M sodium acetate buffer, 0.5 M NaCl, pH 4.5, (4) 0.05% Tween20 in 20 mM sodium phosphate buffer, 0.15 M NaCl, pH 7.0, or (5) 3M urea in 20 mM sodium phosphate buffer, 0.5 M NaCl, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 5F:
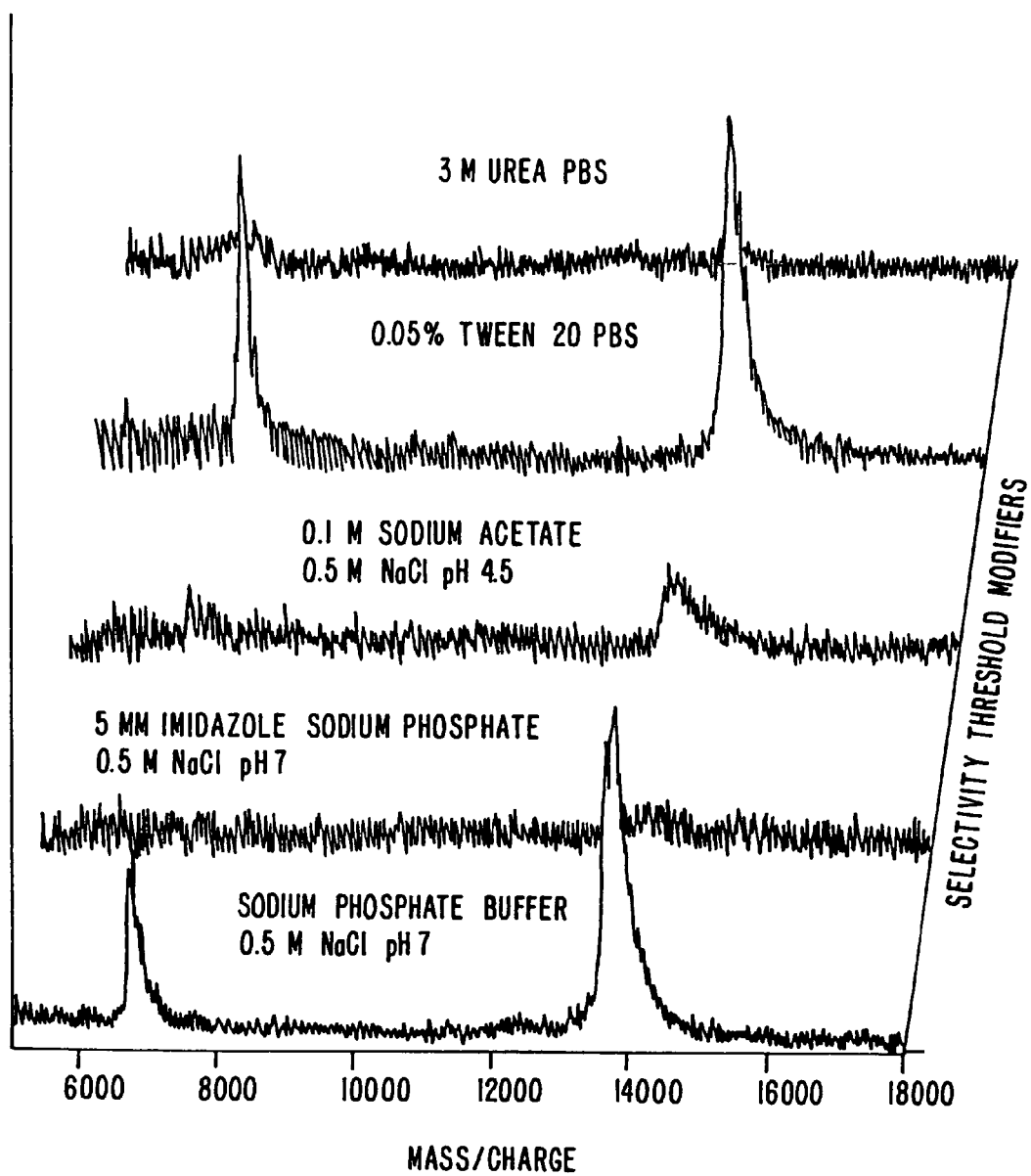

FIG. 5F shows the composite mass spectrum of the lysozyme recognition profile on the immobilized metal chromatographic series adsorbent array. The bottom profile shows the lysozyme signal intensity retained on the immobilized copper ion adsorbent after washing with pH 7 buffer alone. Including a histidine-binding competitive affinity ligand (e.g., imidazole) in the selectivity threshold modifier eliminates the retention of lysozyme. This indicates that the interaction of lysozyme (which has a single histidine residue in the sequence) with an immobilized copper ion adsorbent involves a coordinate covalent binding mechanism. Lowering the pH of the selectivity threshold modifier to pH 4.5 in the sodium acetate buffer, also decreases the retention of lysozyme on the immobilized copper adsorbent. It is believed that this is a result of the protonation of the histidine residue on lysozyme, which inhibits the coordinate covalent interaction. Including detergent (i.e., Tween20) does not affect the interaction. Including urea completely eliminates the retention of lysozyme on the immobilized copper adsorbent.

III. Resolution of Analytes in Human Serum

We resolved analytes in human serum using a variety of adsorbents and eluants. These results show that analytes are differentially retained by different adsorbents, and that retention chromatography is able to provide information at both low and high molecular masses.

A. Human Serum Protein Recognition Profile Using an Immobilized Metal Ion Adsorbent Array Human serum is added to various spots of an adsorbent array of immobilized metal ion (tris(carboxymethyl)ethylenediamine-Cu) adsorbent coated on silicon oxide-coated stainless steel substrate. After incubation in a moist chamber at room temperature for 15 min., each different spot of adsorbent is washed with one of the following eluants (selectivity threshold modifiers):

(1) 20 mM sodium phosphate buffer, 0.5 M NaCl, pH 7.0, (2) 5 mM imidazole in 20 mM sodium phosphate buffer, 0.5 M NaCl, pH 7.0, (3) 0.1 M sodium acetate buffer, 0.5 M NaCl, pH 4.5, (4) 0.05% Tween20 in 20 mM sodium phosphate buffer, 0.15 M NaCl, pH 7.0, and (5) 3M urea in 20 mM sodium phosphate buffer, 0.5 M NaCl, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 6A:
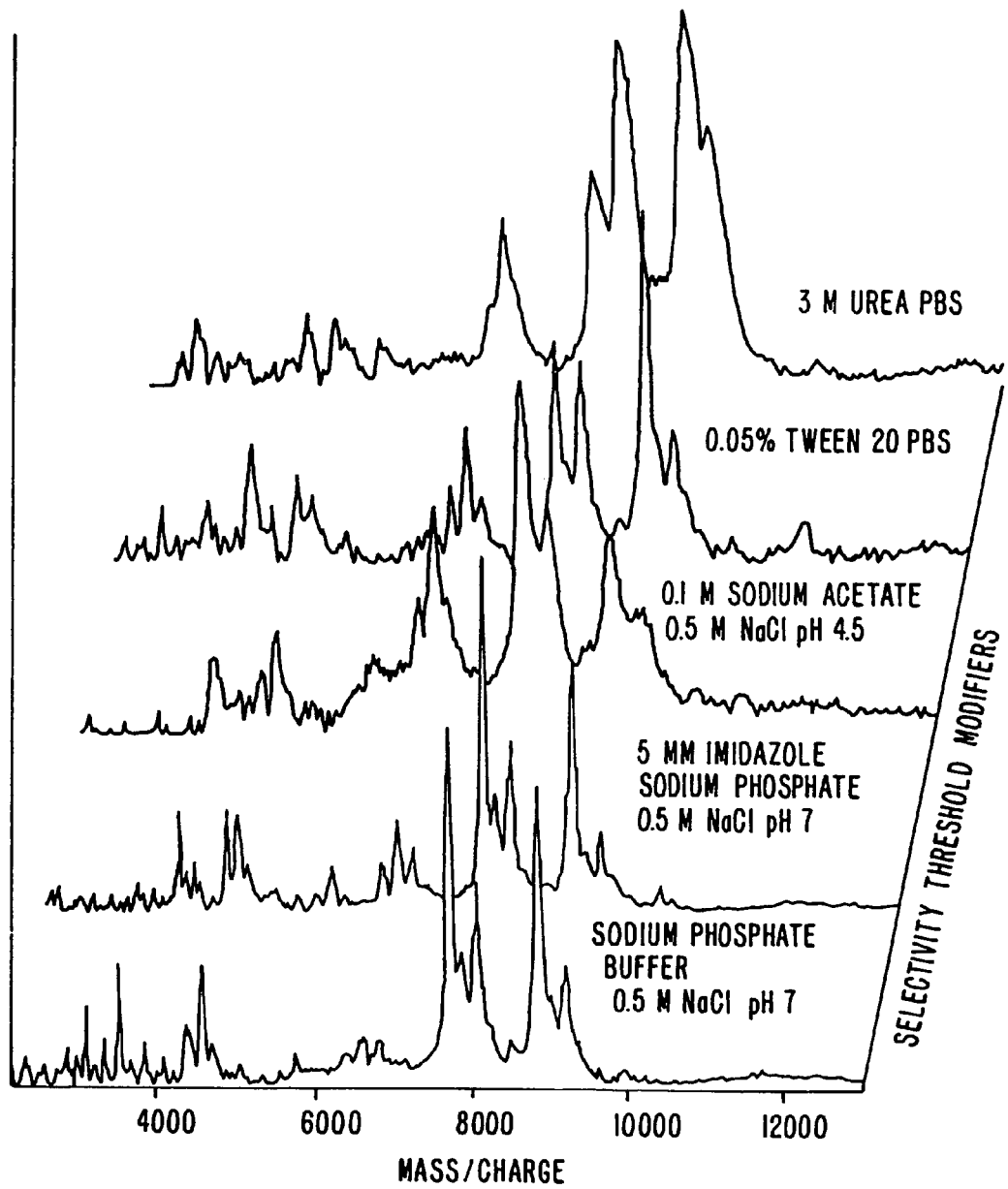
FIGS. 6A-6B show the resolution at low and high molecular mass of analytes in human serum by an immobilized metal adsorbent.
Figure 6B:
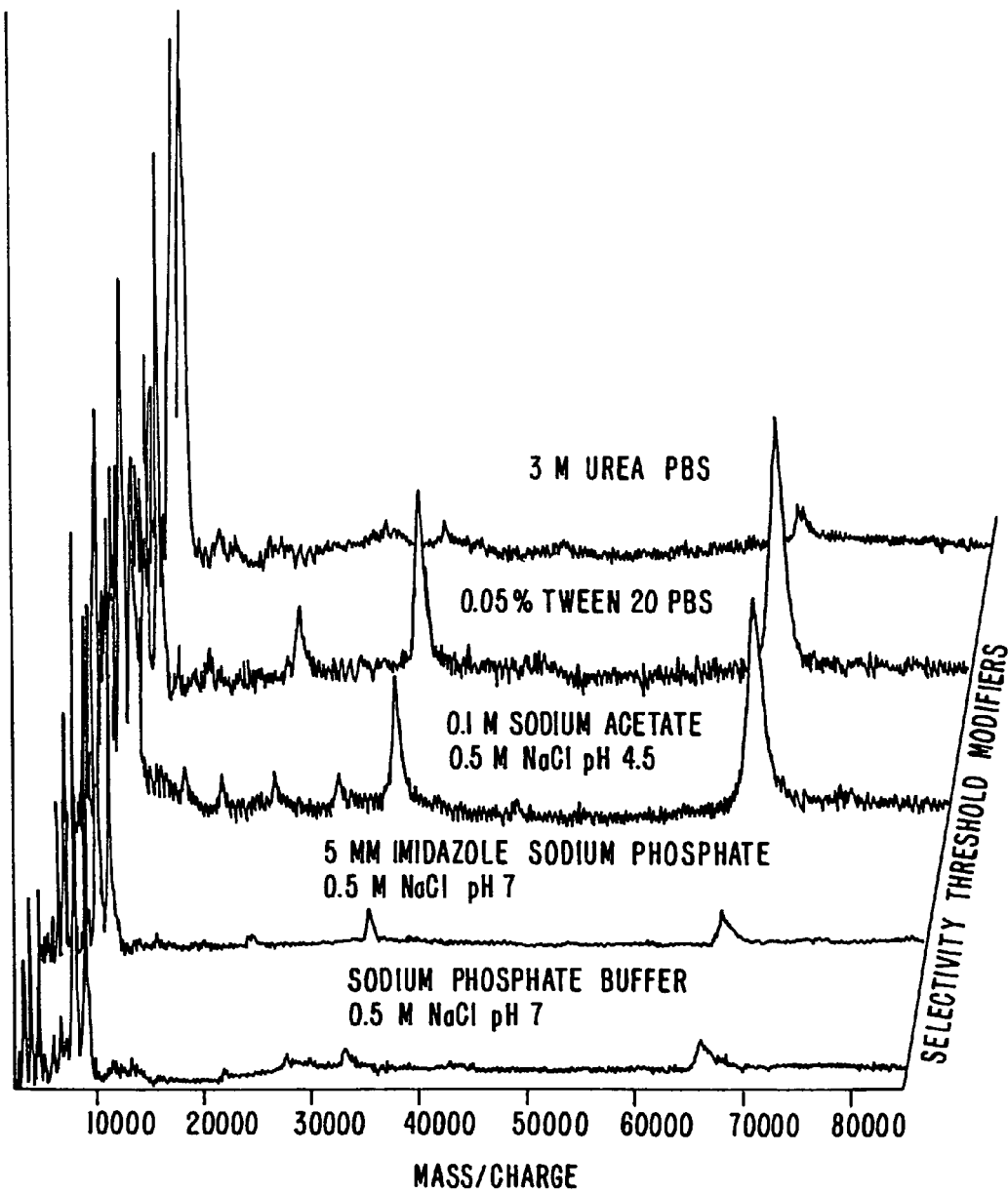

FIGS. 6A and 6B show the composite mass spectrum at low and high molecular mass of the serum protein recognition profile on the immobilized metal chromatographic series adsorbent array. The bottom profile shows the serum proteins retained on the immobilized copper adsorbent after washing with pH 7 buffer alone. Including a histidine-binding competitive affinity ligand (e.g., imidazole), or detergent (e.g., Tween20), or urea in the selectivity threshold modifier, or lowering the pH of the selectivity threshold modifier to 4.5, differentially enhances or decreases the retention of different components of the complex protein mixture on the same adsorbent.

B. Human Serum Protein Recognition Profile Using a Plurality of Different Adsorbents Human serum is added to various spots of an adsorbent array of the following different adsorbents:

(1) $C_3$ hydrophobic, (2) phenyl hydrophobic, (3) anion exchange, (4) cation exchange, and (5) immobilized metal (tris(carboxymethyl)ethylenediamine-Cu).

Each adsorbent is coated on a silicon oxide-coated stainless steel substrate. After incubation in a moist chamber at room temperature for 15 min., each spot of adsorbent is washed with 0.05% Tween20 in 20 mM sodium phosphate buffer, 0.15 M NaCl, pH 7.0 as the selectivity threshold modifier.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with the mass spectrometer using a nitrogen laser (355 nm) and a 60 cm flight tube. The data is analyzed by computer and exported to GRAMS/32c for data overlay presentation.

Figure 7A:
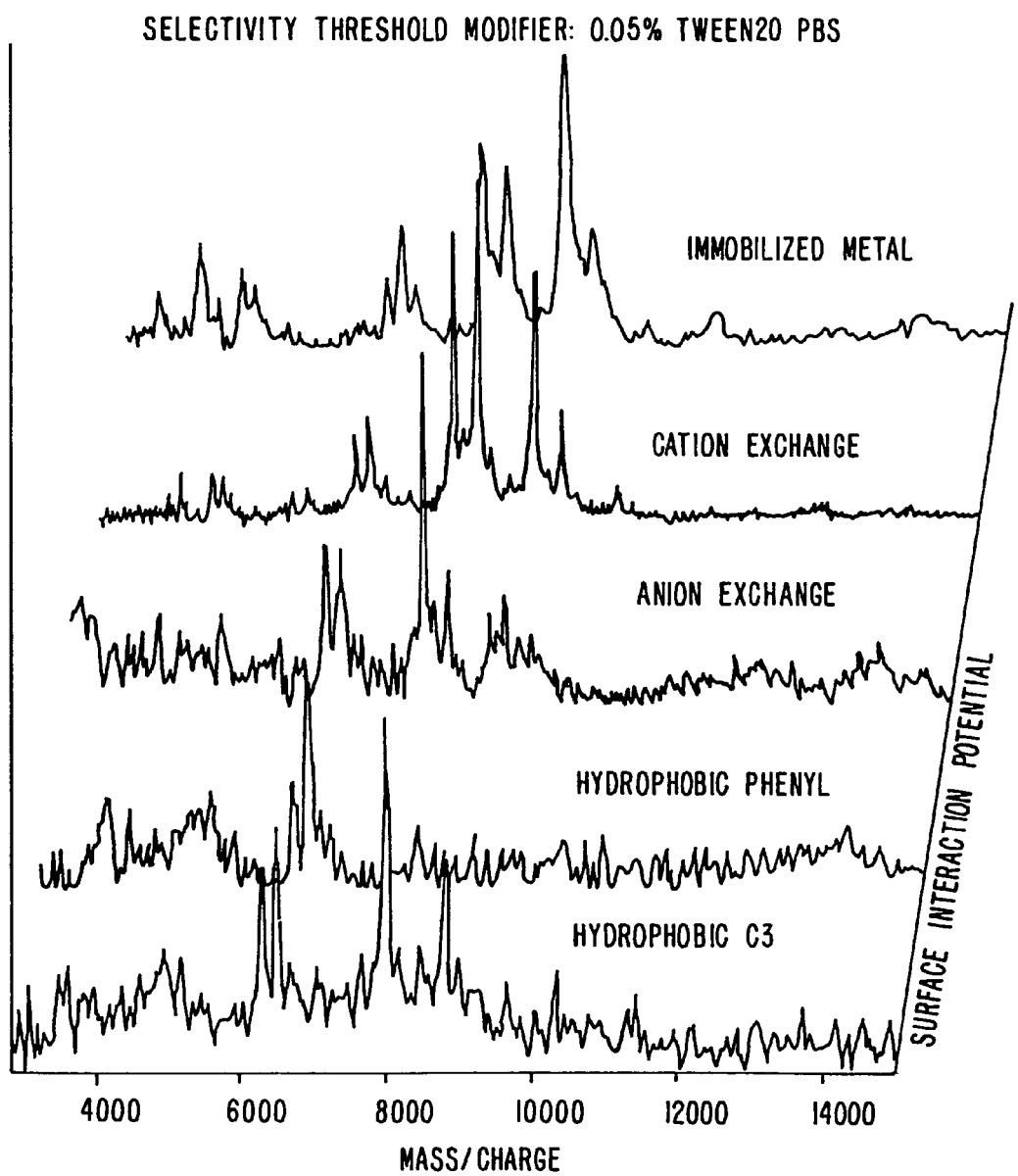
FIGS. 7A-7B show the resolution at low and high molecular mass of analytes in human serum by a variety of adsorbents using the same eluant.
Figure 7B:
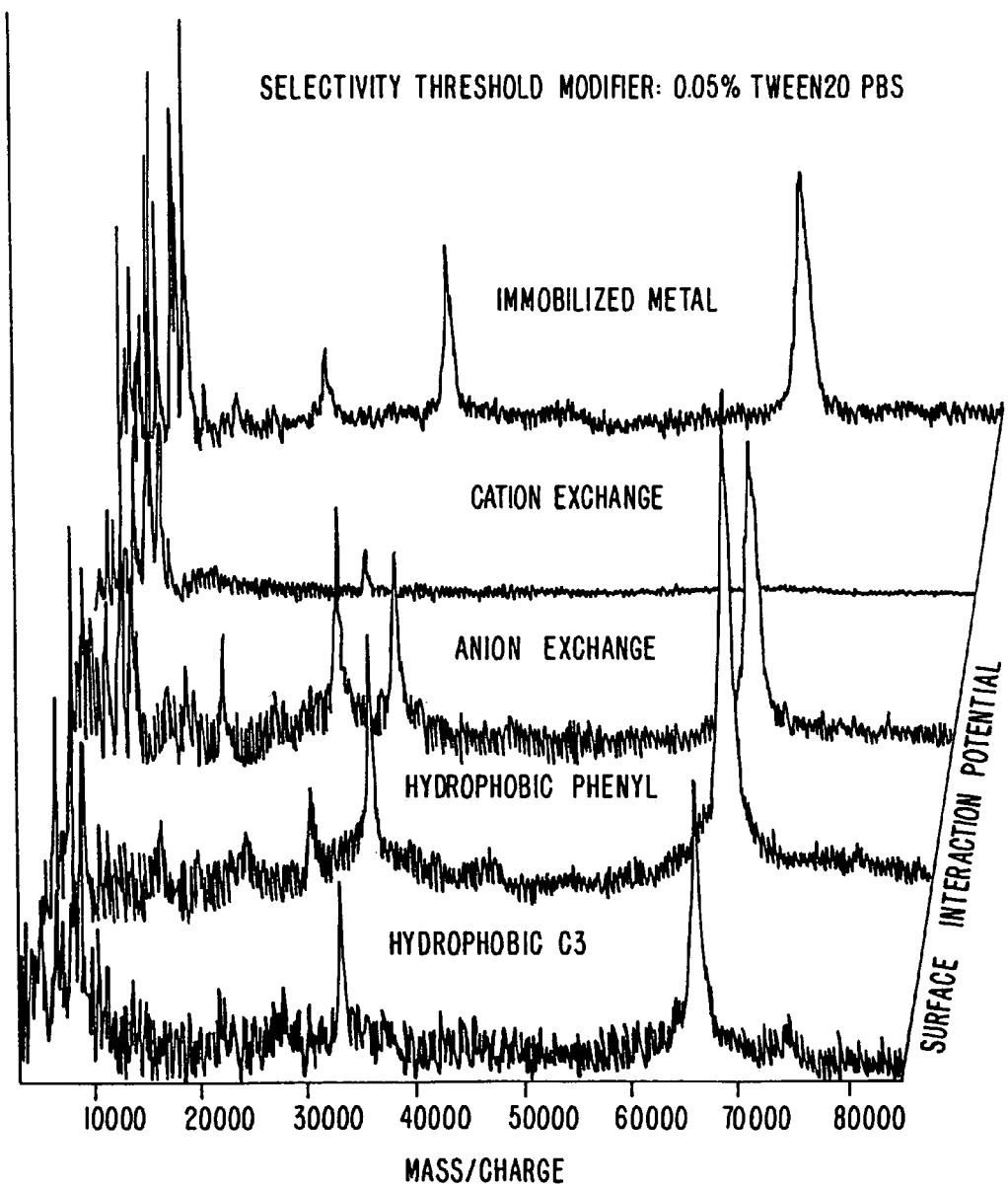

FIGS. 7A and 7B show the composite mass spectrum of the serum protein recognition profile on various adsorbents of a chromatographic series adsorbent array. The use of a single selectivity threshold modifier on a plurality of different adsorbents (having different binding characteristics) differentially enhances or decreases the retention of different components of the complex protein mixture on the different adsorbents.

IV. Resolution of Analytes in Preterm Infant Urine

We resolved analytes in preterm infant urine using a variety of adsorbents and eluants. These results show that because adsorbents retain analytes differentially, the use of various adsorbents provides great resolving ability. They also show the ability to identify adsorbents that preferentially retain specific analytes, which is useful for developing purification schemes.

A. Resolution of Analytes in Preterm Infant Urine Using A Variety of Adsorbents and the Same Eluant (Water)

Preterm infant urine (2 µl) is added to various spots of a carbonized PEEK polymer substrate coated with the following different adsorbents:

(1) $C_8$ hydrophobic (Octyl Sepharose, available from Sigma), (2) phenyl hydrophobic (Phenyl Sepharose, available from Sigma),
(3) anion exchange (Q Sepharose, available from Sigma),
(4) cation exchange (S Sepharose, available from Sigma),
(5) immobilized metal (IDA-Cu, Chelating Sepharose, available from Pharmacia), and
(6) immobilized metal (tris(carboxymethyl)ethylenediamine-Cu Sepharose).

After incubation in a moist chamber at room temperature for 15 min., each spot of adsorbent is washed with water as the selectivity threshold modifier. Each wash includes pipetting 1 µl of wash solution in and out of the spot of adsorbent three times. This is repeated with a fresh aliquot of wash solution. An aliquot of 0.3 µl of sinapinic acid (5 mg/ml 50% acetonitrile:0.5% TFA) is added and allowed to air dry. The array is analyzed with the a laser desorption/ionization time-of-flight mass spectrometer from Hewlett Packard (Model 2030) that uses a nitrogen laser (355 nm) and a 150 cm flight tube. The data is analyzed by HP MALDI TOF software and exported to GRAMS/32c for data overlay presentation.

Figure 8A:
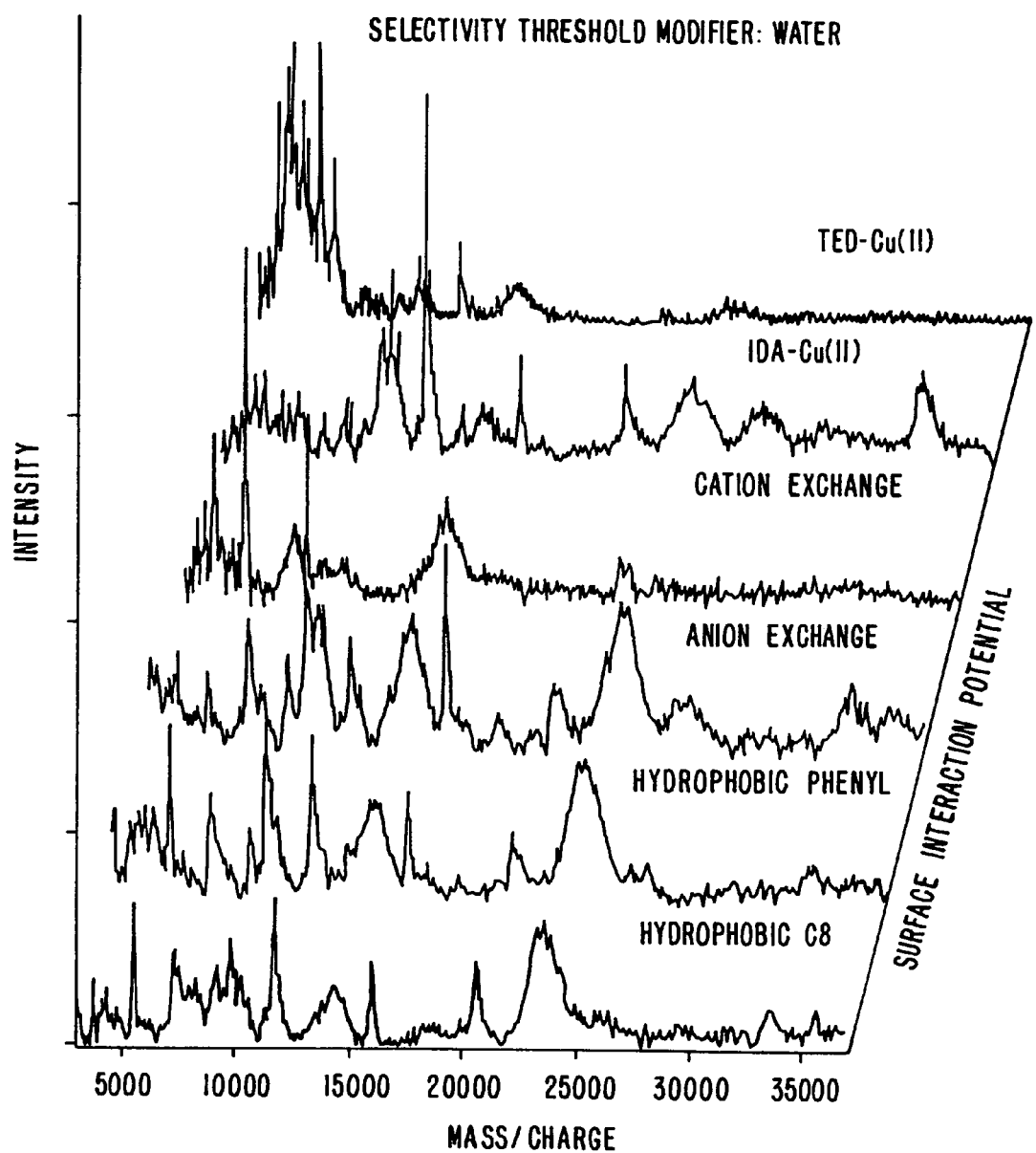
FIGS. 8A-8B show the resolution at low and high molecular mass of analytes in preterm infant urine by a variety of adsorbents using water as the eluant.
Figure 8B:
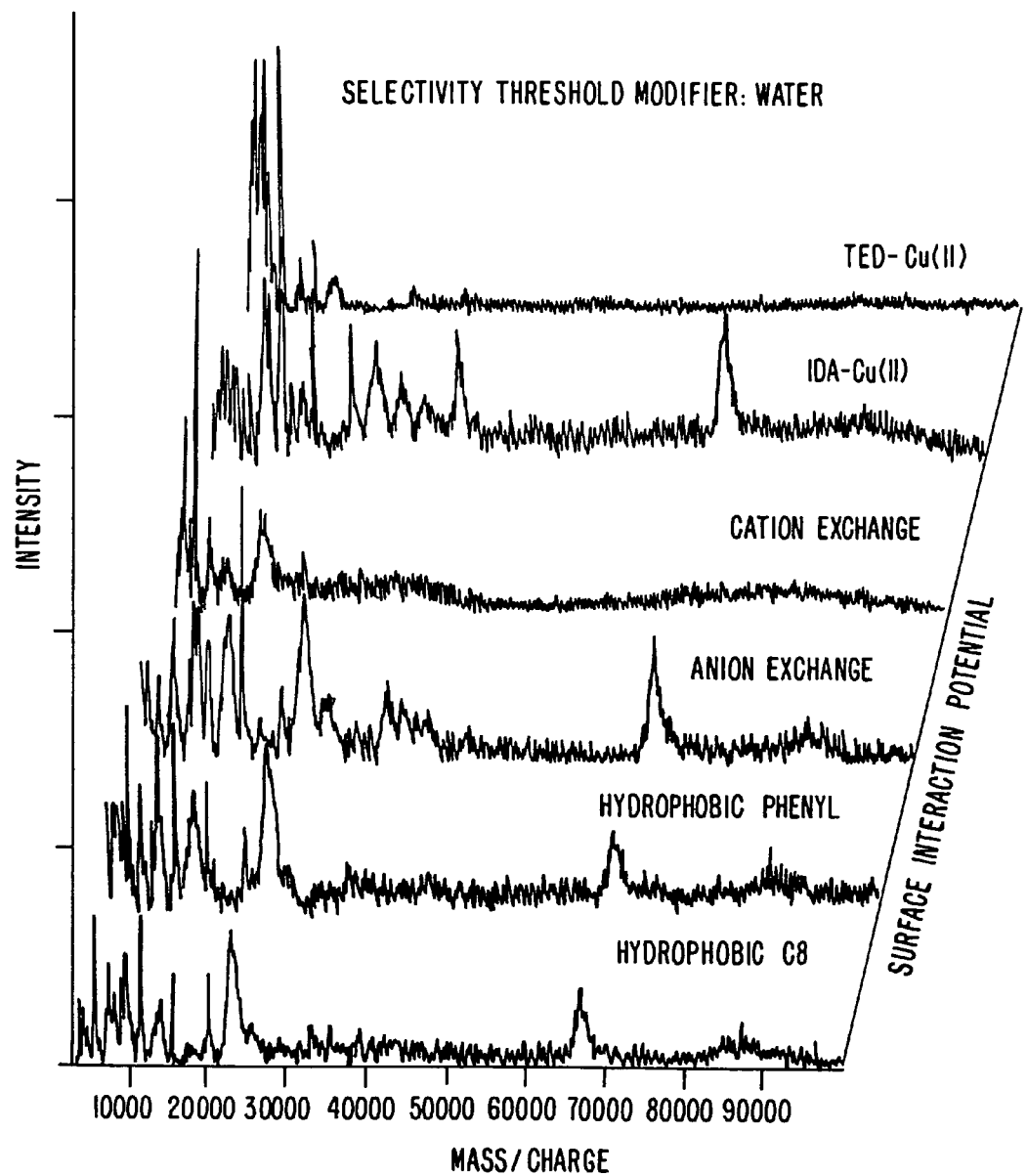

FIGS. 8A and 8B show the composite mass spectrum at low and high molecular mass of the preterm infant urine protein recognition profile on the various adsorbents of a chromatographic series. The use of a single selectivity threshold modifier (i.e., water) on the various adsorbents (each having a different binding characteristic) differentially enhances or decreases the retention of different components of the complex protein mixture like on the different adsorbents.

B. Resolution of Analytes in Preterm Infant Urine Using a Hydrophobic Phenyl Adsorbent Indirectly Coupled to the Substrate and Three Different Eluants Preterm infant urine (2 µl) is added to various spots of a carbonized PEEK polymer substrate coated with phenyl hydrophobic adsorbent (Phenyl Sepharose, available from Sigma). After incubation in a moist chamber at room temperature for 15 min., each spot of adsorbent is washed with one of the following eluants (selectivity threshold modifiers):
(1) water,
(2) 2M urea in 20 mM sodium phosphate buffer, 0.15 M NaCl, pH 7.0, and
(3) 0.1% Tween20 in 20 mM sodium phosphate buffer, 0.15 M NaCl, pH 7.0.

Each wash includes pipetting 1 µl of wash solution in and out of the spot of adsorbent three times. This process is repeated with a fresh aliquot of wash solution. Thereafter, the spot of adsorbent is washed with 1 µl of water two times. An aliquot of 0.3 µl of sinapinic acid (5 mg/ml 50% acetonitrile:0.5% TFA) is added and allowed to air dry. The array is analyzed with a laser desorption/ionization time-of-flight mass spectrometer from Hewlett Packard (Model 2030) that uses a nitrogen laser (355 nm) and a 150 cm flight tube. The data is analyzed by HP MALDI TOF software and exported to GRAMS/32c for data overlay presentation.

Figure 9:
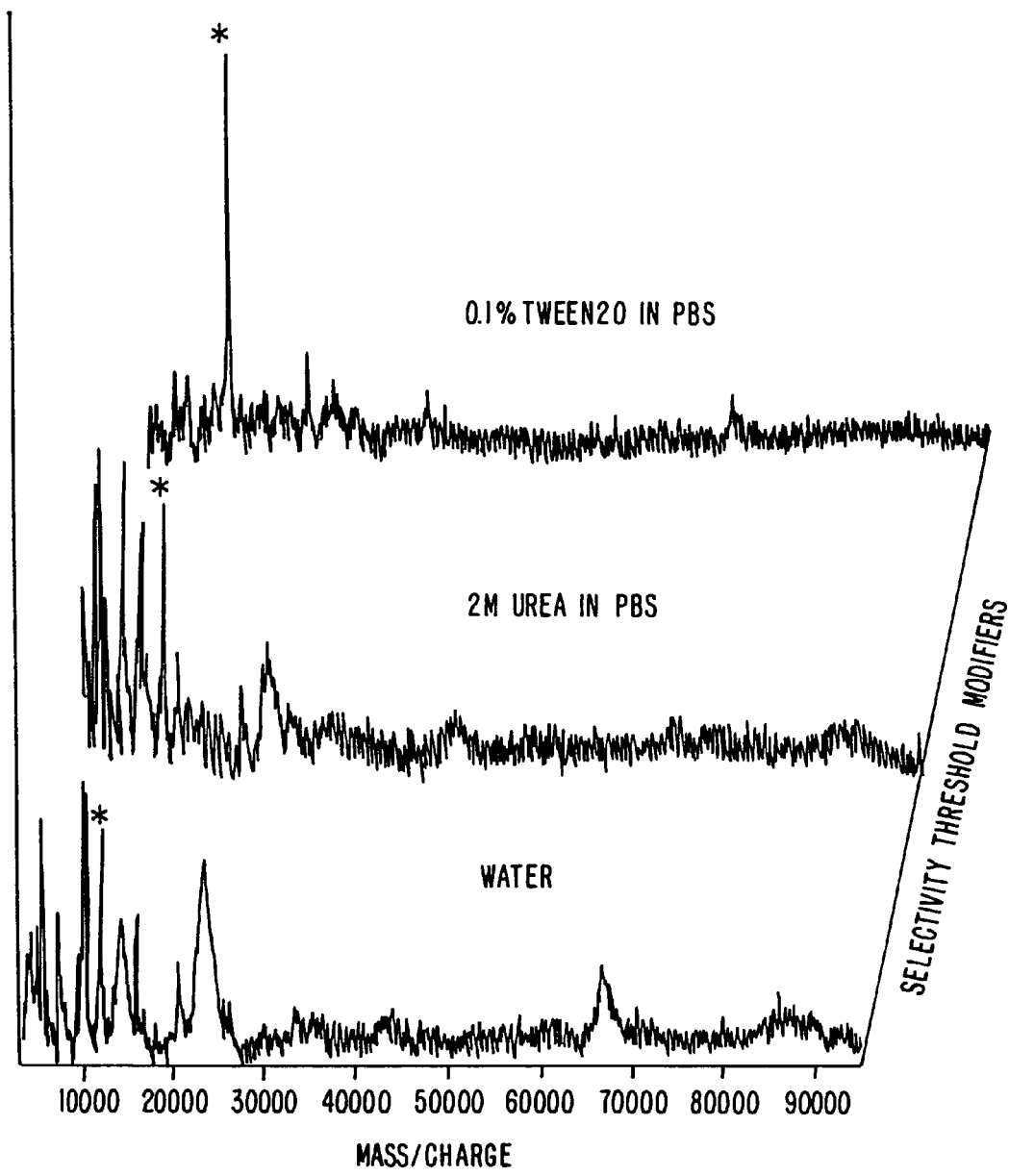
FIG. 9 shows resolution of analytes in preterm infant urine using a hydrophobic phenyl adsorbent and three different eluants, resulting in the discovery of selective retention of one of the analytes (*) by the Tween wash condition.

FIG. 9 shows the composite mass spectrum of the preterm infant urine protein recognition profile on the hydrophobic phenyl adsorbent of a chromatographic series. The application of various eluants having different elution characteristics on a single adsorbent differentially enhances or decreases the retention of different components of the complex protein mixture. One of the components (marked by *) is selectively retained on the hydrophobic phenyl adsorbent when 01% Tween20 in PBS is used as the eluant.

V. Identification of Proteins in Culture Medium from Two Different Cell Lives

This example illustrates the identification of proteins that are differentially expressed in cells with adsorbent array: Chromatographic series.

Two different breast cancer cell lines are cultured for the same period of time in a constant composition culture medium. After concentration with a filtration unit, an aliquot of 1 µl of each culture medium is added to various spots of a an adsorbent array (Ciphergen Biosystems, Inc., Palo Alto, Calif.) of immobilized metal (tris(carboxymethyl)ethylenediamine-Cu) adsorbent coated on silicon oxide-coated stainless steel as substrate. After incubation at room temperature in a moist chamber for 15 min., a spot of adsorbent is washed with either one of the following eluants (selectivity threshold modifiers):
(1) 20 mM sodium phosphate buffer, 0.5 M NaCl, pH 7.0,
(2) 20 mM imidazole in 20 mM sodium phosphate buffer, 05 M NaCl, pH 7.0,
(3) 0.1 M sodium acetate buffer, 0.5 M NaCl, pH 4.5,
(4) 0.1% Tween20 in 20 mM sodium phosphate buffer, 0.15 M NaCl, pH 7.0,
(5) 3M urea in 10 mM sodium phosphate buffer, 0.5 M NaCl, pH 7.0, or
(6) 1% TFA.

Each wash includes pipetting 1 µl of wash solution in and out of the spot of adsorbent three times. This is repeated, with a fresh aliquot of wash solution. Afterwards, the spot of adsorbent is washed with 1 µl of water two times. An aliquot of 0.3 µl of sinapinic acid (5 mg/ml 50% acetonitrile:0.5% trifluoroacetic acid) is added and allowed to air dry. The array is analyzed with a laser desorption/ionization time-of-flight mass spectrometer that uses a nitrogen laser (355 nm) and a 60 cm flight tube. The data is analyzed by computer and exported to GRAMS/32c (Galactic Industries Corporation) for data overlay presentation.

Figure 10A:
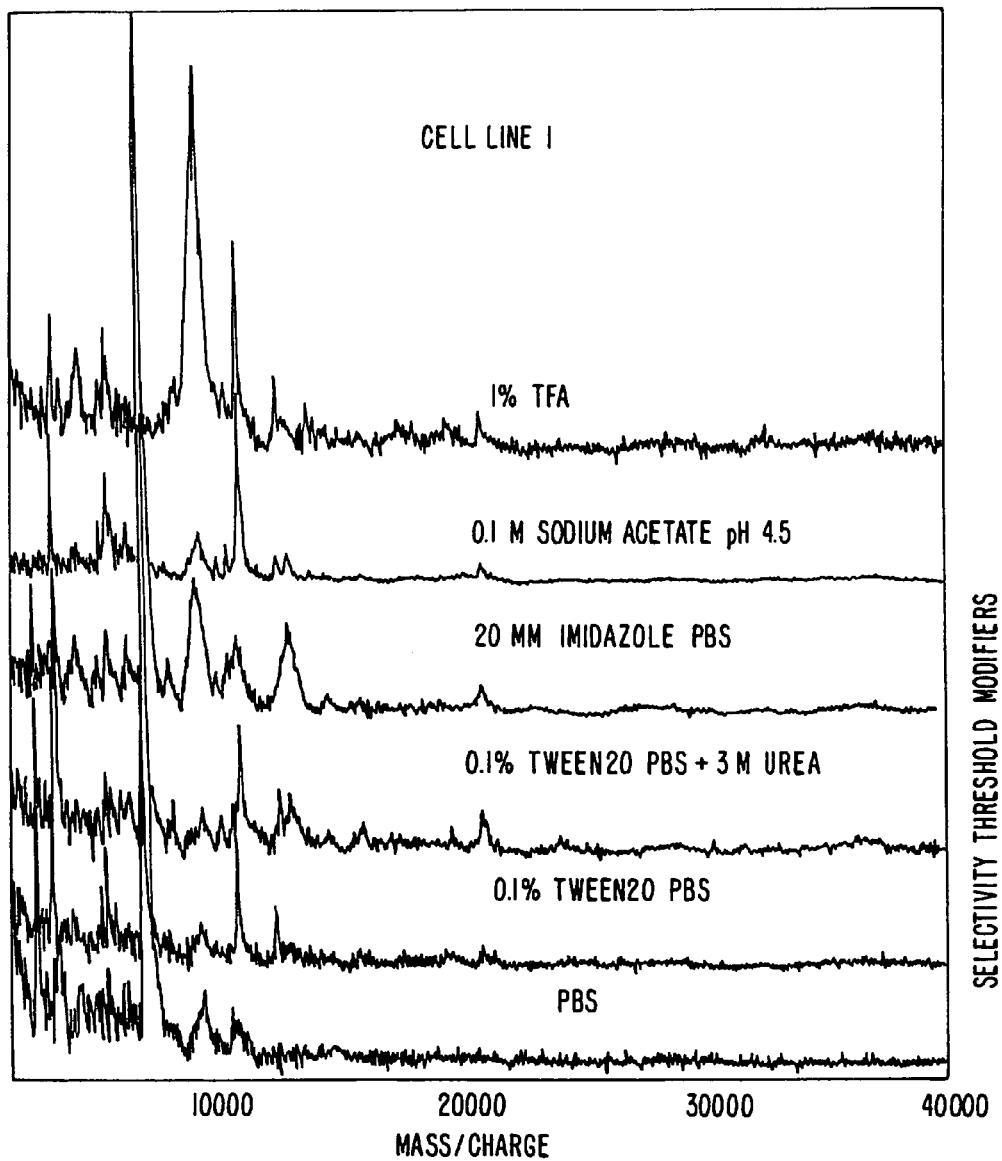
FIG. 10A-10D show the resolution of analytes in cell culture medium of two different breast cancer cell lines.

FIG. 10A shows the composite mass spectrum of cell secreted protein recognition profile of cell line 1 on an immobilized metal (Cu) chromatographic series adsorbent array. The application of various eluants of different selectivity thresholds on a single adsorbent differentially enhances or decreases the retention of different components of a complex protein mixture like cell culture medium.

Figure 10B:
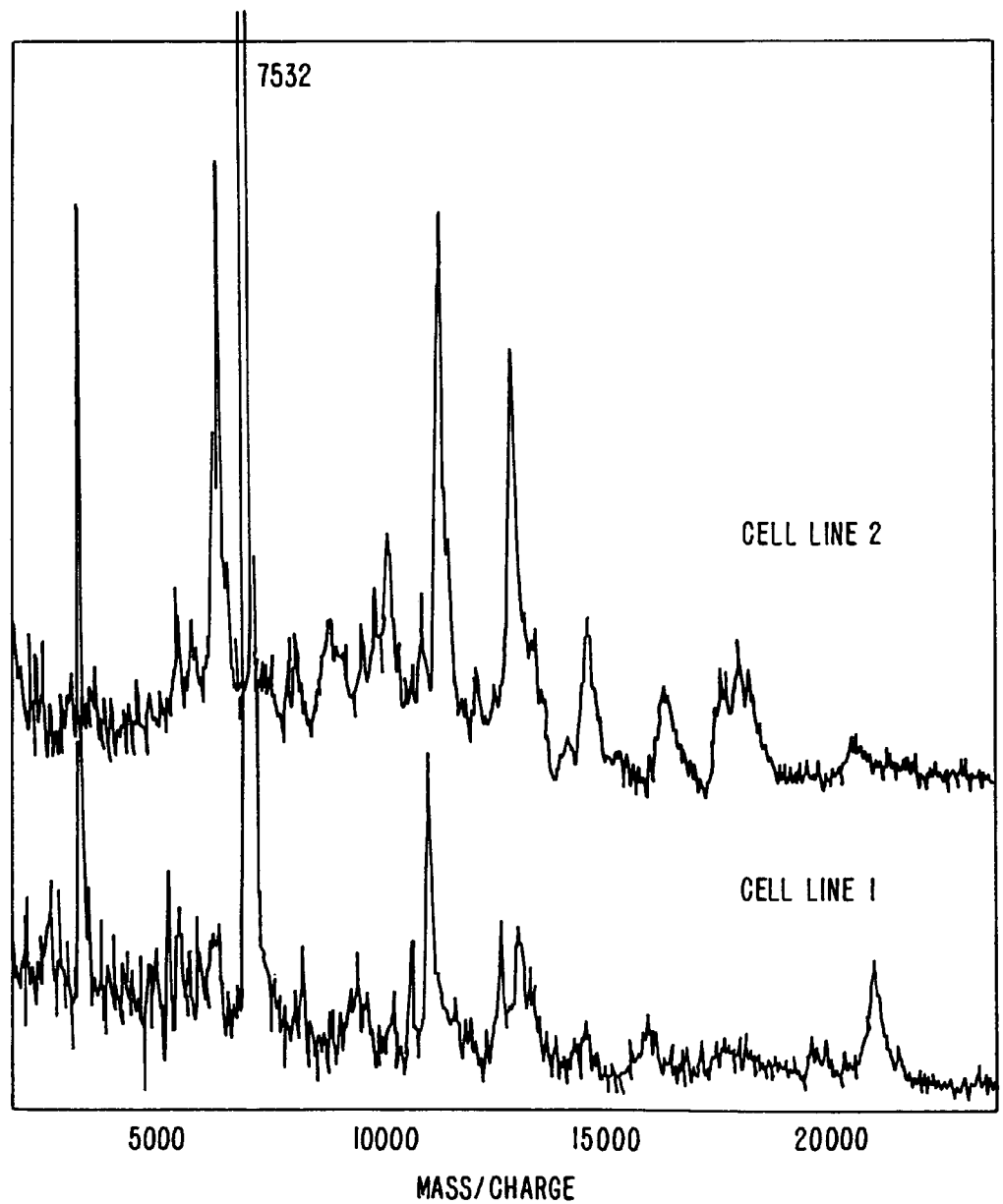

FIG. 10B shows the composite mass spectrum of cell secreted protein recognition profiles of both cell lines on an immobilized metal (Cu) chromatographic series adsorbent array. The same eluant, 0.1% Tween20+3 M urea in 10 mM sodium phosphate buffer, 0.5 M NaCl, pH 7.0, is used to wash away unretained materials. The peak marked 7532 Da is the major retained peak in cell line 1 secreted protein that is not expressed in cell line 2.

Figure 10C:
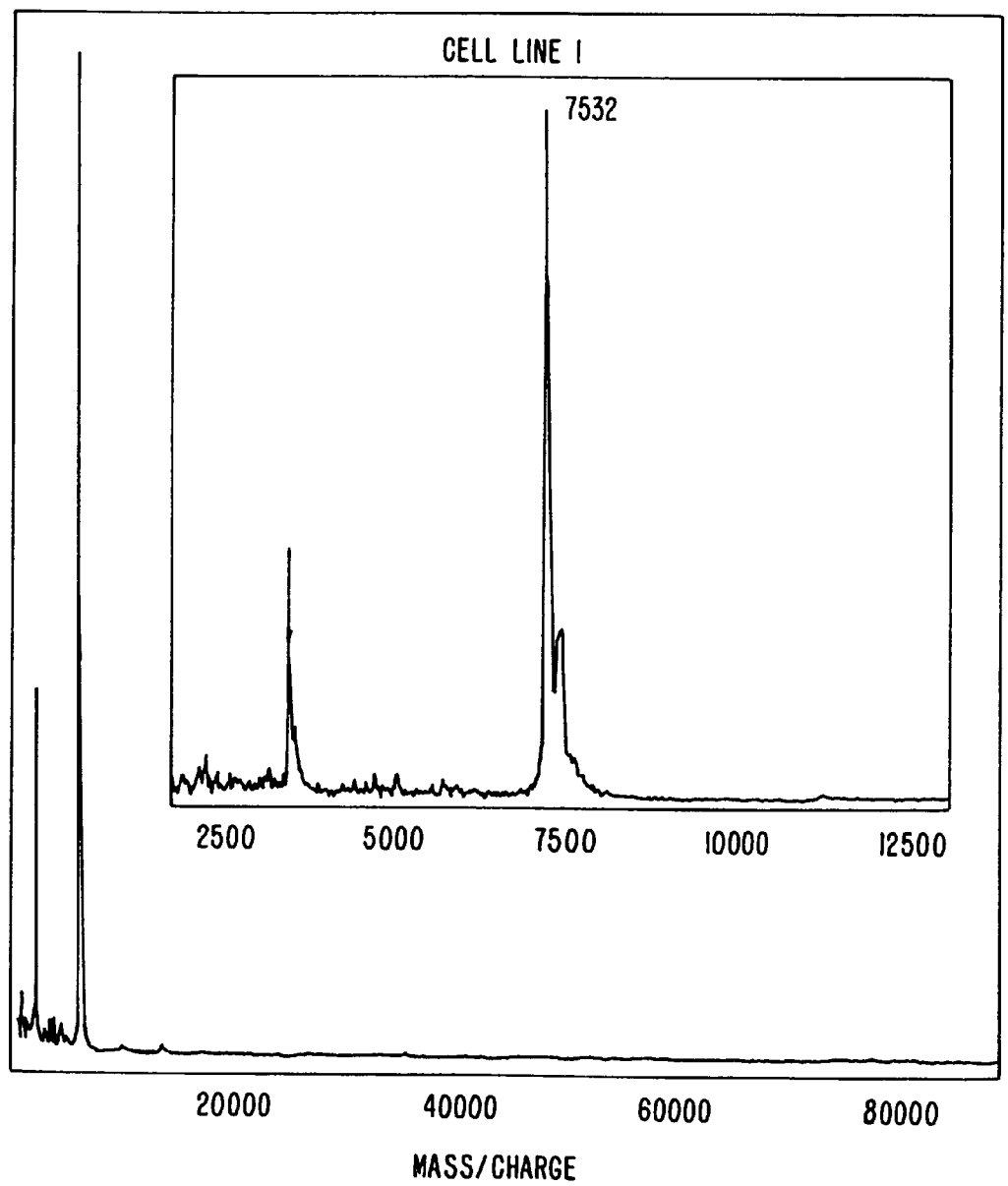

FIG. 10C shows the composite mass spectrum of cell secreted protein recognition profiles of cell line 1 on an immobilized metal (Ni) chromatographic series adsorbent array. Using the same eluant, 0.1% Tween20+3 M urea in 10 mM sodium phosphate buffer, 0.5 M NaCl, pH 7.0, but employing an adsorbent of different surface interaction potential (i.e., immobilized Ni metal vs immobilized Cu metal), the 7532 Da peak is the only retained protein among all the cell line 1 secreted proteins. The inset shows the same mass spectrum on an expanded scale. The smaller peak at 3766 Da is the doubly charged species of the same protein.

Figure 10D:
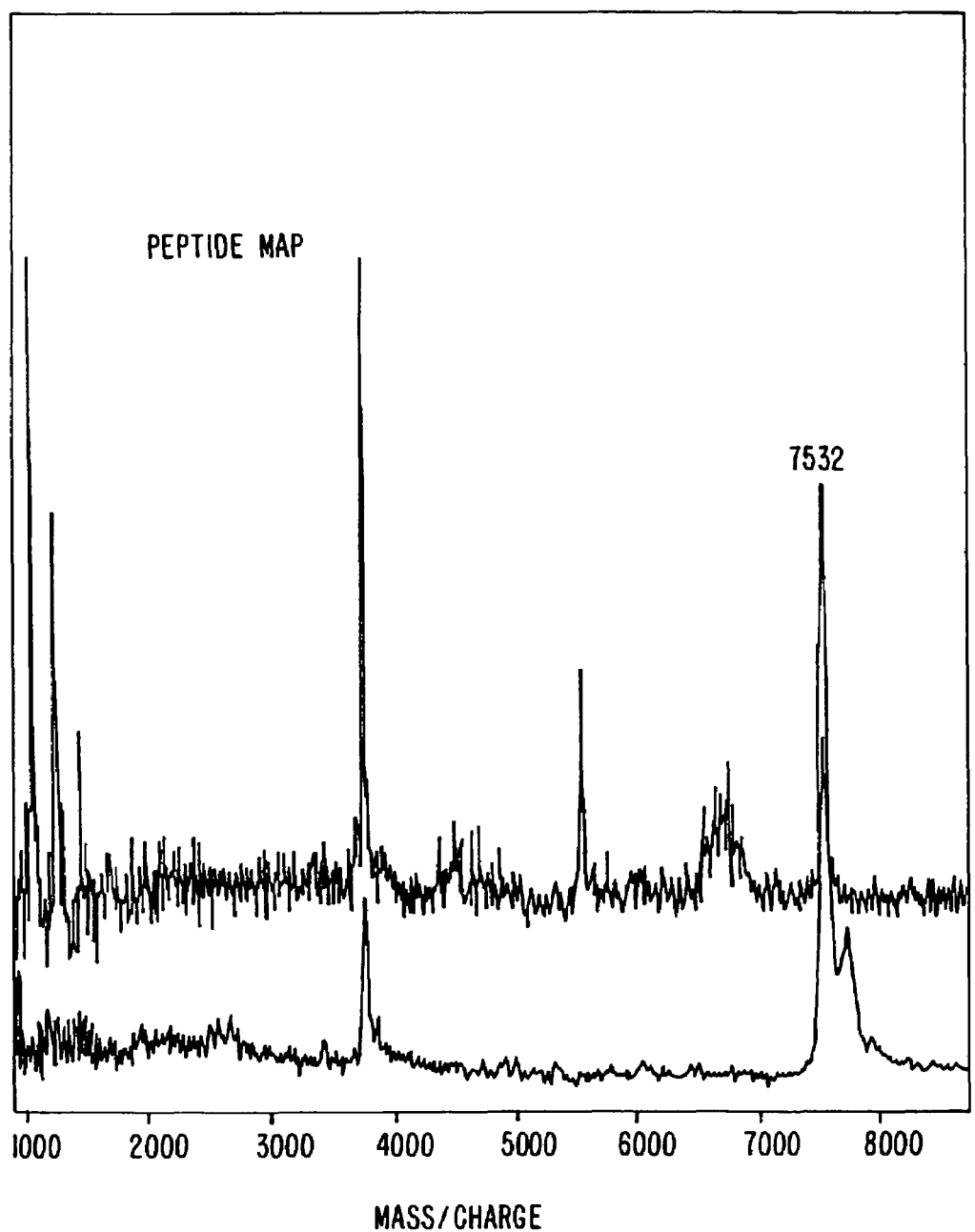

FIG. 10D shows the composite mass spectrum of cell secreted protein recognition profiles of cell line 1 on an immobilized metal (Ni) chromatographic series adsorbent array before (lower profile) and after (top profile) in situ trypsin digestion. The peptide map generated for a pure protein is a fingerprint of that protein and can be used for identification.

VI. Comparison of Retentate Chromatography with 2D Gel Electrophoresis

One advantage of retentate chromatography is the ability to rapidly resolve analytes in a variety of dimensions, resulting in high information content about a variety of physico-chemical characteristics. In contrast, 2D gel electrophoresis provides resolution in two dimensions only.

Figure 11:
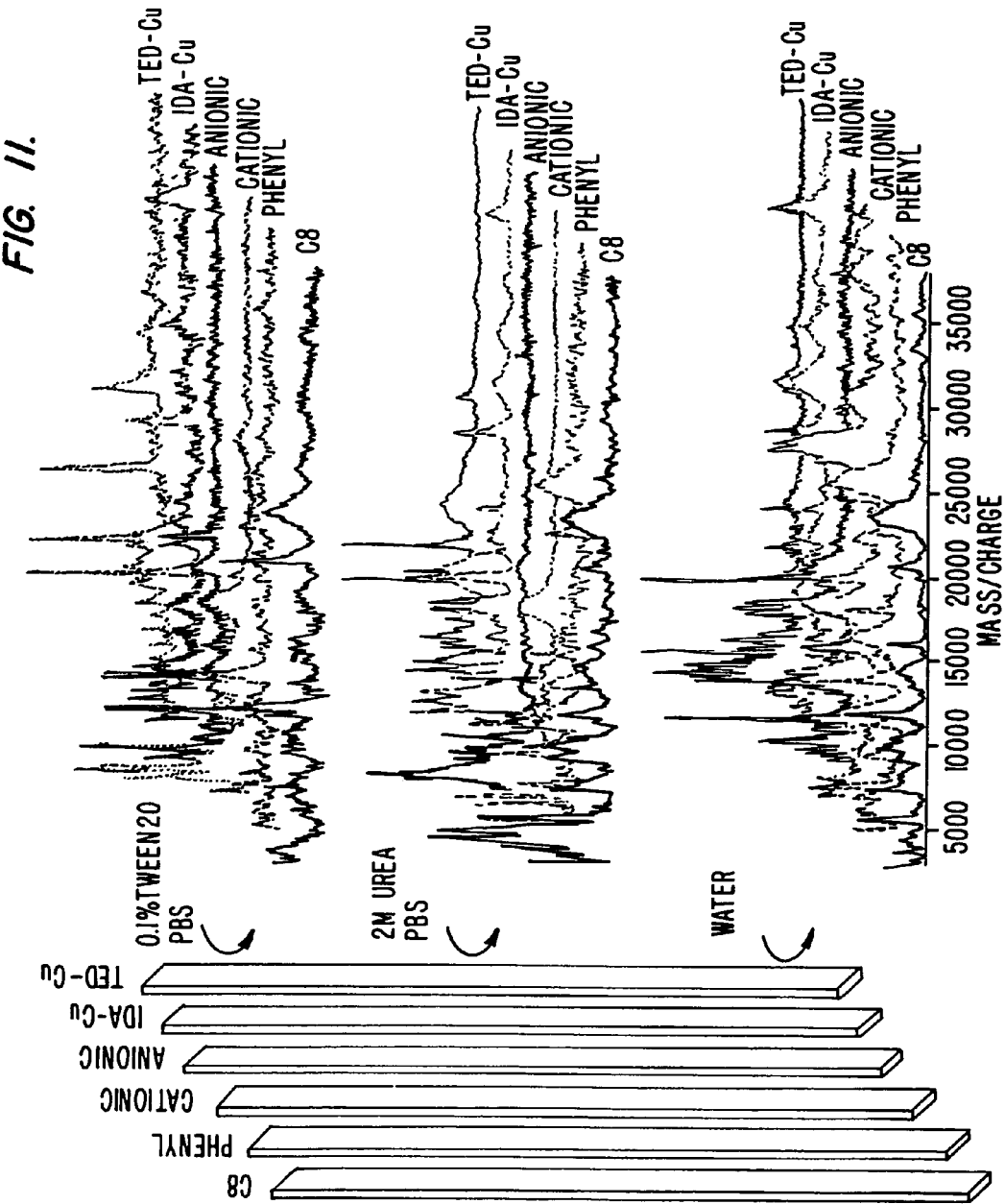
FIG. 11 shows a composite retention map of preterm infant urine exposed to selectivity conditions defined by six different adsorbents and three different eluants.

FIG. 11 shows a preterm infant urine protein recognition profile on phenyl hydrophobic adsorbent of a chromatographic series. The application of various eluants and adsorbents yields multi-dimensional information. The use of different selectivity conditions differentially enhances or decreases the retention of various components of a complex protein mixture (such as preterm infant urine), resulting in detailed resolution of analytes.

Figure 12:
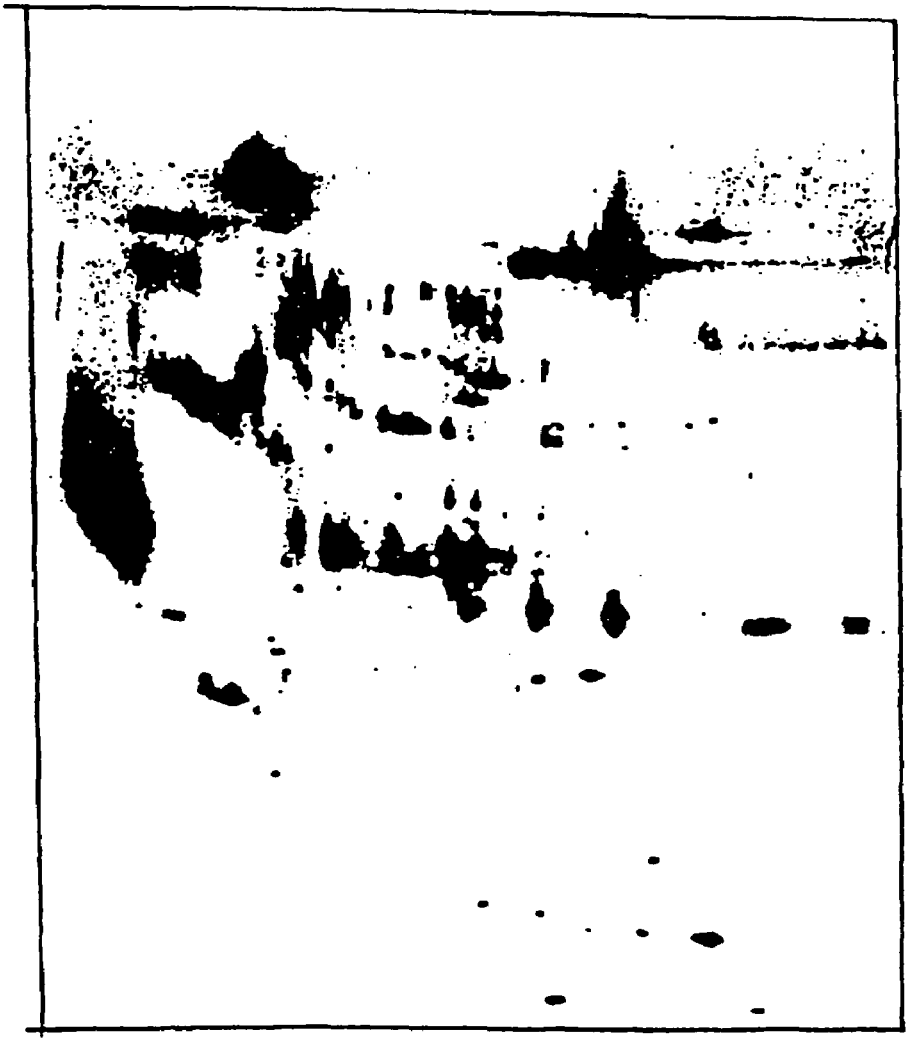
FIG. 12 shows a two-dimensional polyacrylamide gel (pI and apparent molecular mass) of preterm infant urine.
Figure 13:
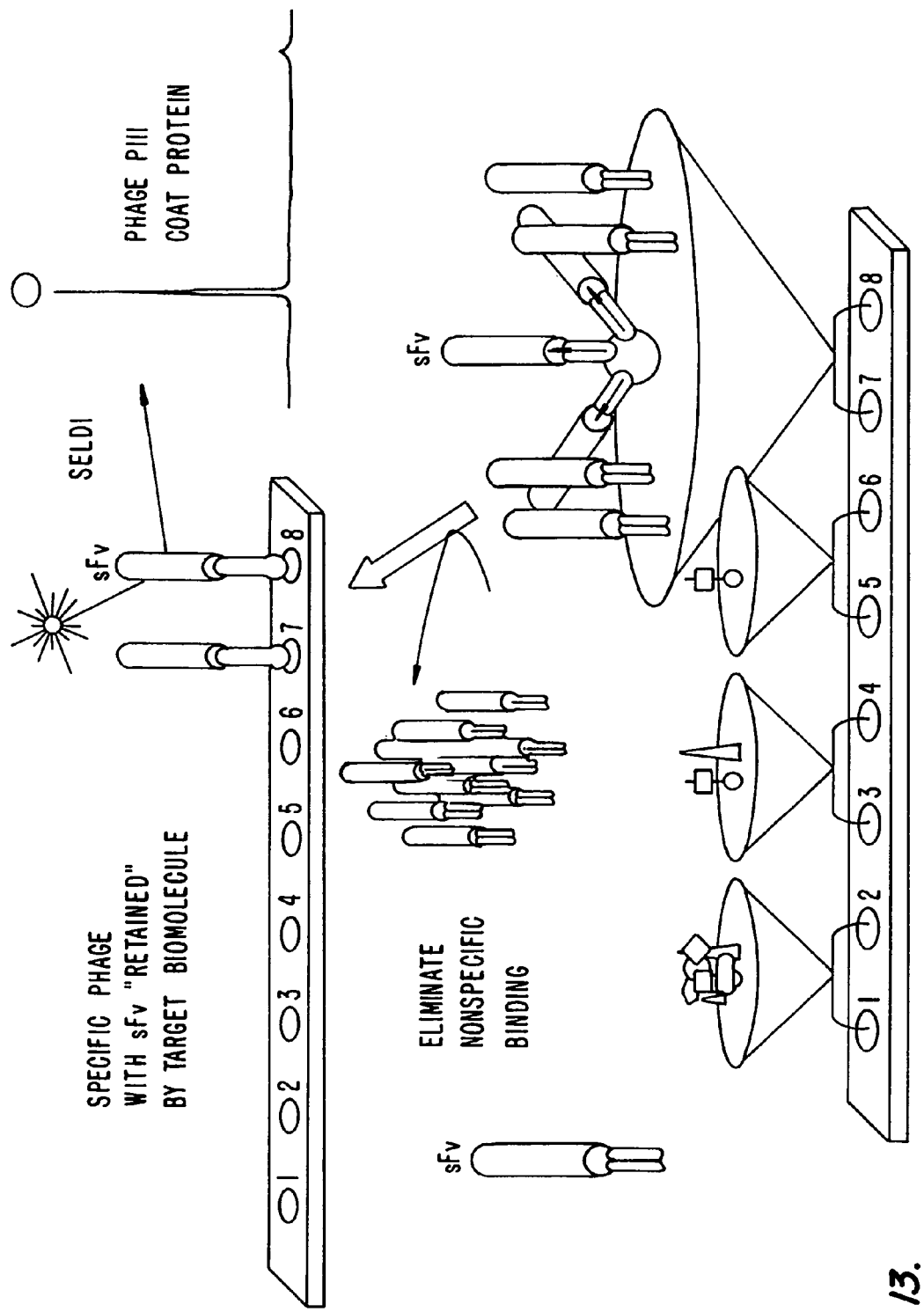
FIG. 13 shows a method of panning with phage display libraries for a phage having a surface protein that specifically binds to a target analyte. The substrate depicted at the top shows that even a few specifically bound phage can be detected by desorption spectrometry through the detection of the many coat proteins that phage contains. At the bottom, a substrate with several adsorbent spots is developed so that the target analyte is specifically bound. Phage are exposed to the spots. Bound phage are detected by desorption spectrometry. Phage bound to another spot can be isolated and grown.
Figure 14:
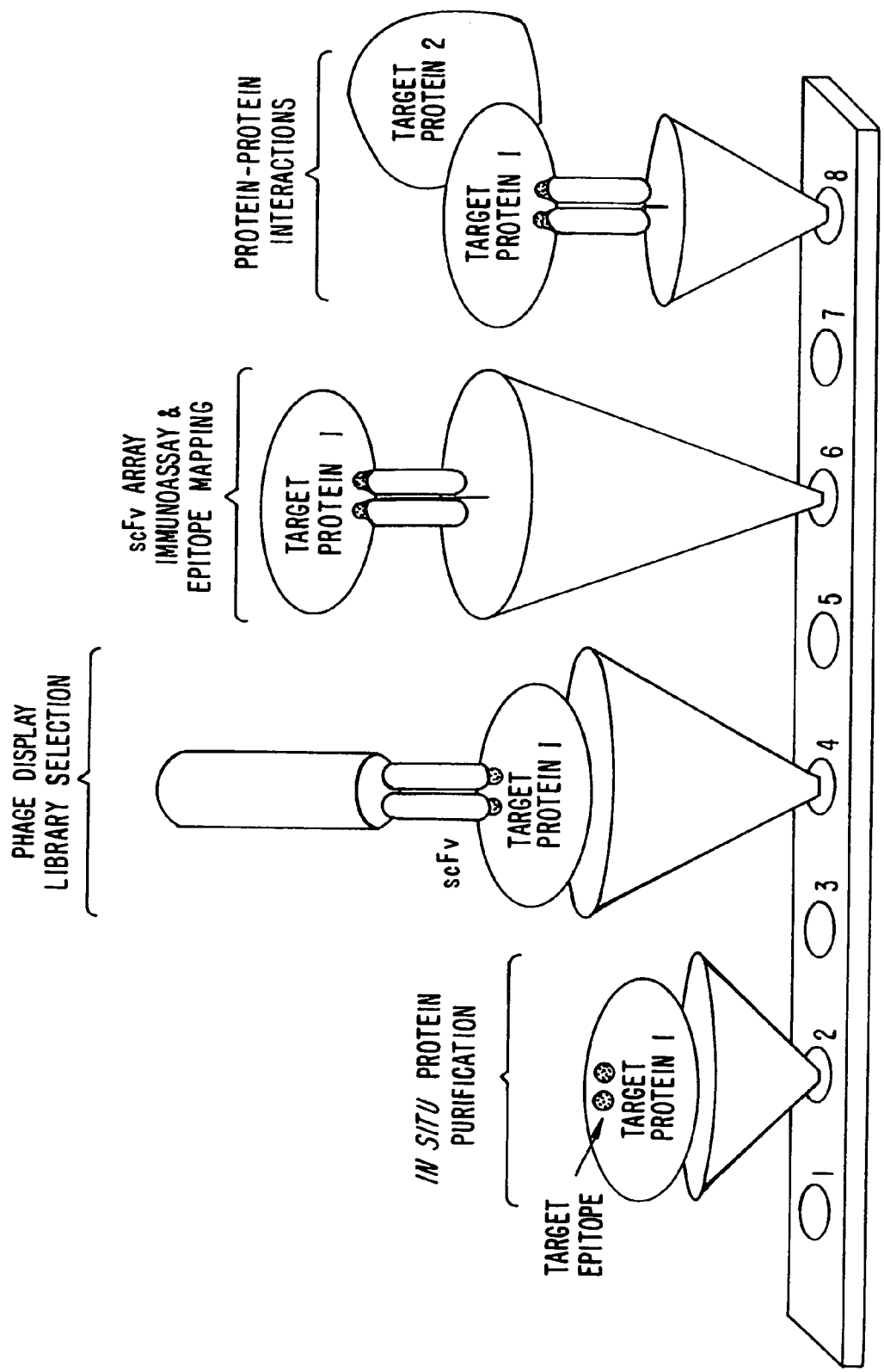
FIG. 14 shows how a ligand agent, in this case a single chain antibody, identified by a panning method can be used as an adsorbent to dock a target protein for use in protein-protein interaction studies. A target is purified in situ (spot 2) and used to pan a phage display library (spot 4). A single chain antibody is isolated and attached to a substrate (spot 6) as an adsorbent. The target is then adsorbed to the single chain antibody. The target is now docked for the study of protein-protein interactions (spot 8).
Figure 15:
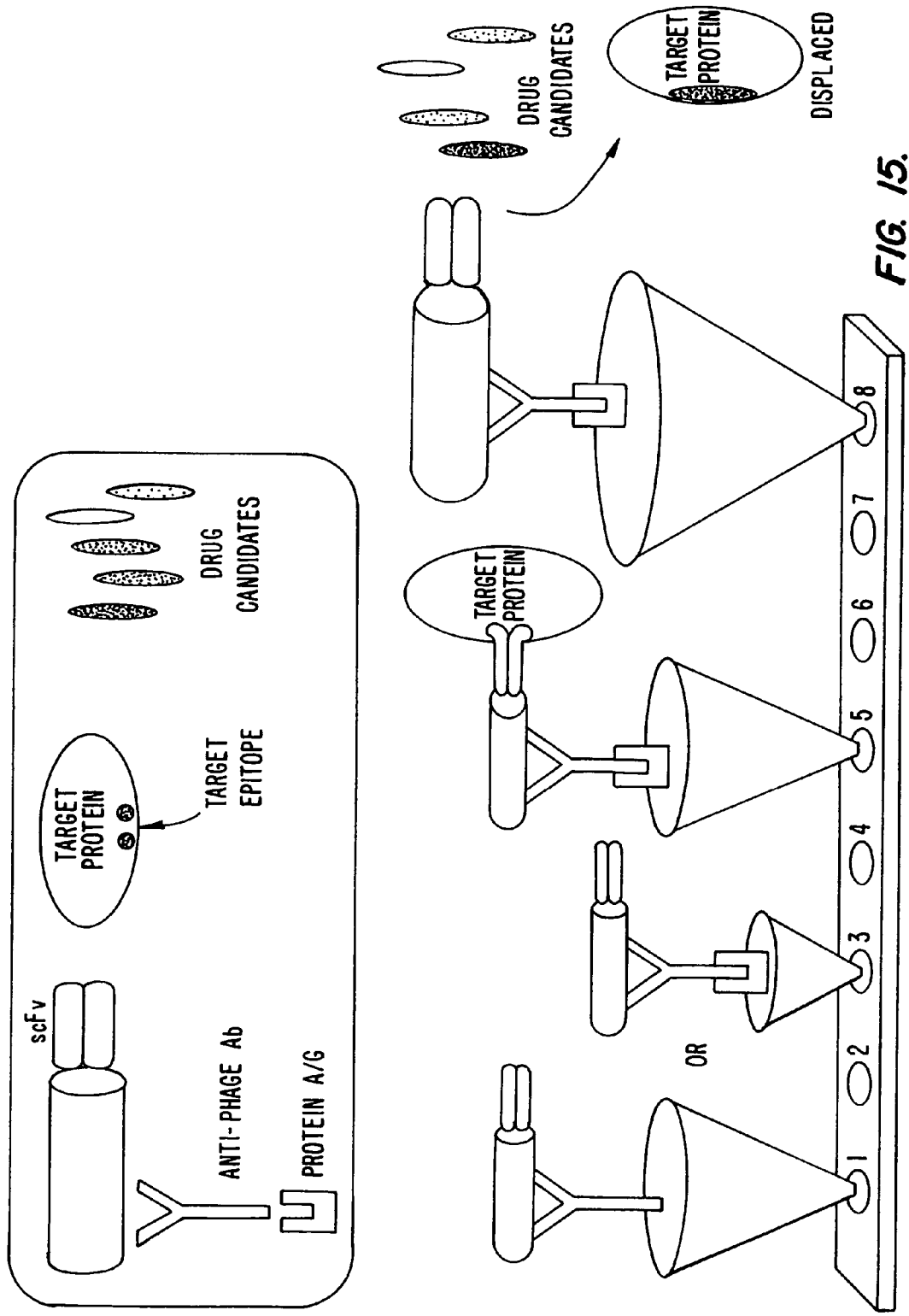
FIG. 15 shows a method for screening drug candidates for the ability to interfere with protein binding to a ligand, in this case a single-chain antibody. A single chain antibody specific for a target protein is docked to a spot on a substrate through, for example, an anti-phage antibody which, itself, can be docked through protein A or protein G. The single chain antibody is exposed to the target protein and to drug candidates. The ability of the drug to bind to the analyte protein and to interfere with ligand binding to analyte is monitored by desorption spectrometry.
Figure 16:
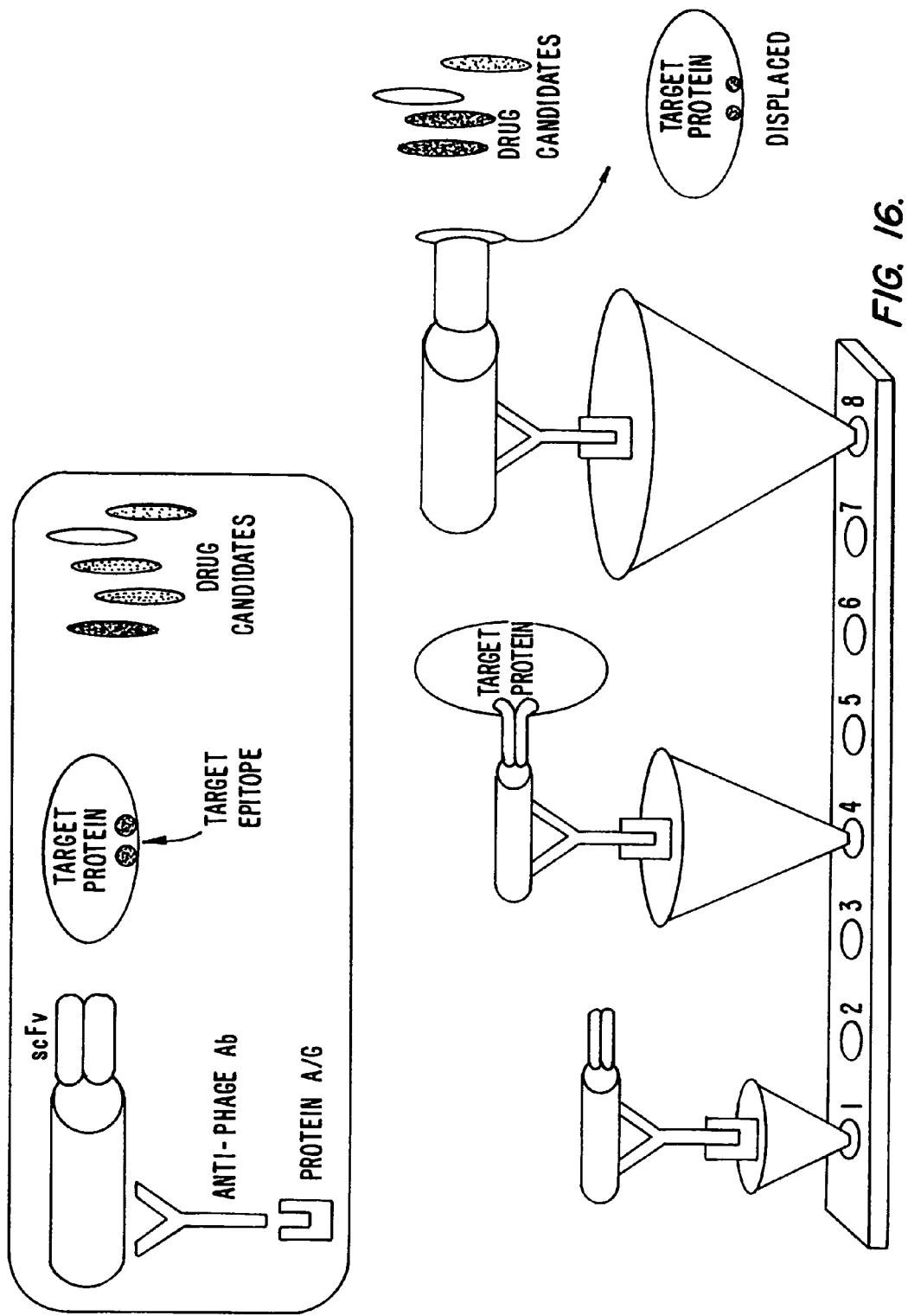
FIG. 16 shows a method for screening drug candidates for the ability to interfere with protein binding to a ligand. The method is similar to that depicted in the previous figure, except one monitors the ability of the drug to interfere with analyte binding by binding, itself, to the ligand by desorption spectrometry.
Figure 17:
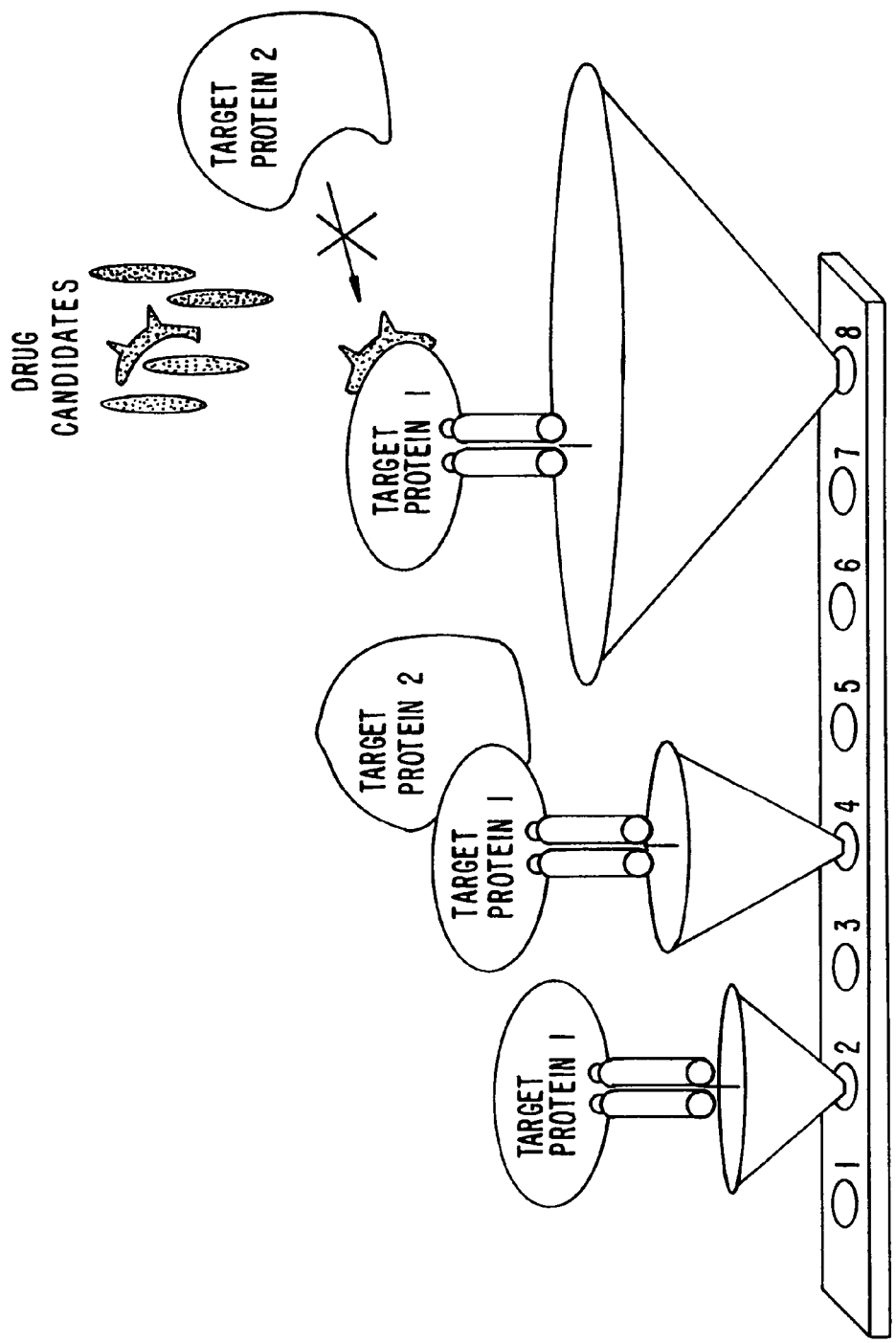
FIG. 17 shows a method for screening drug candidates for the ability to interfere with target protein (Target protein 1) binding to a secondary ligand (Target Protein II). As in the previous two figures, the target is docked to the substrate becoming, itself, an adsorbent for the ligand. In this case, the analyte is docked through a single chain antibody. The target is then exposed to the ligand and to the drug candidates. The ability of the drug to interfere with binding between the analyte and the ligand (by, e.g., binding to the target analyte) is monitored by desorption spectrometry.
Figure 18:
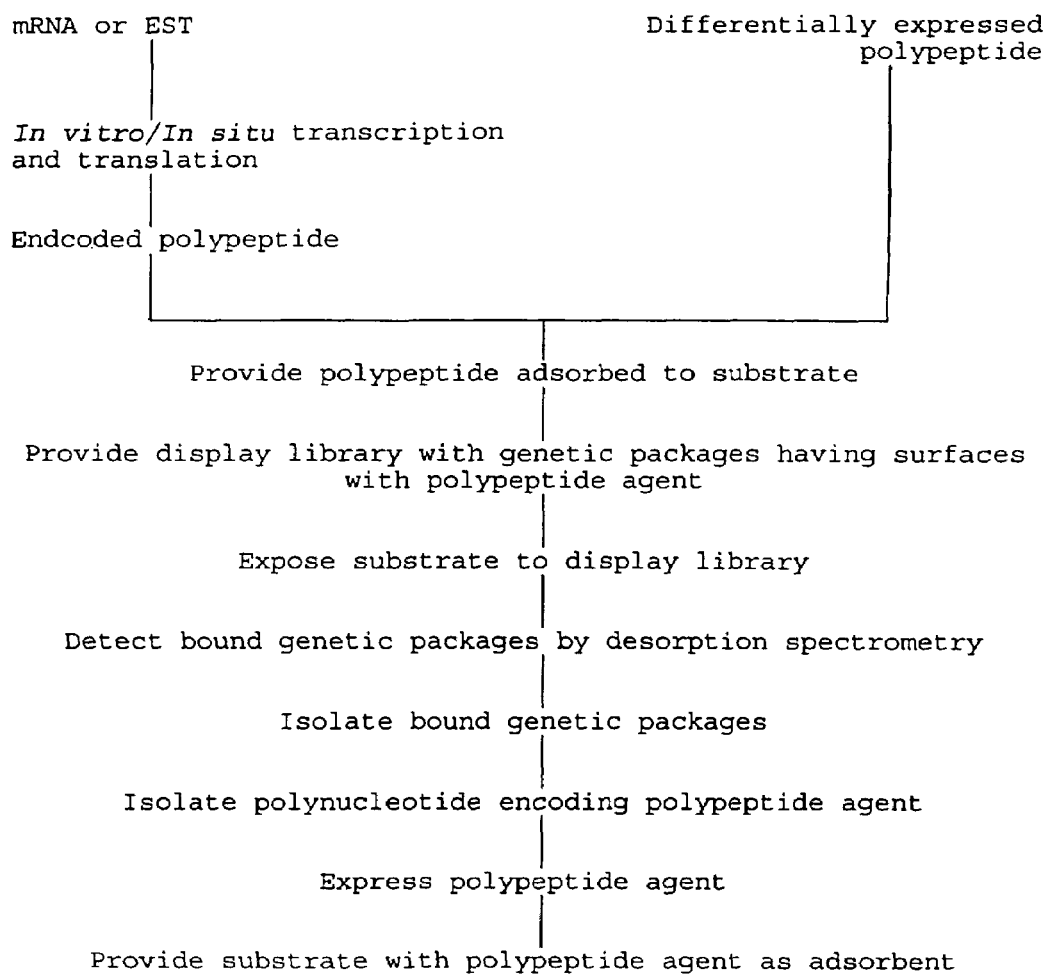
FIG. 18 depicts a flow chart beginning with the identification of differentially expressed mRNA or polypeptides and ending with the creation of a diagnostic platform for specifically binding the polypeptide for detection by desorption spectrometry.
Figure 19:
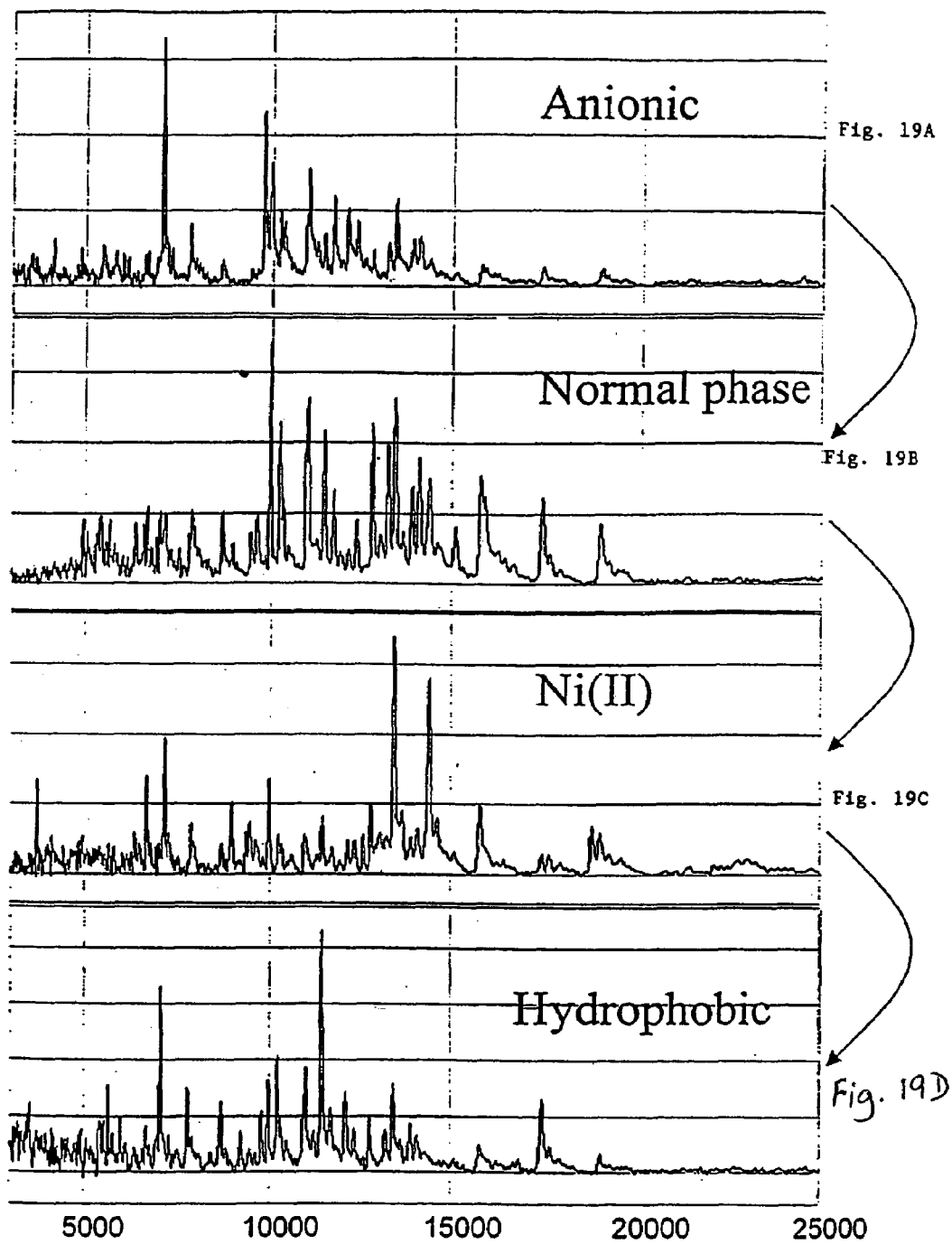
FIGS. 19A-19D show a retention map of *Hemophilus* lysate on an adsorbent array.

In contrast, FIG. 12 shows a two-dimensional separation of proteins in preterm infant urine according to pI and molecular mass. The gel provides information about two dimensions, only, as compared to the six dimensions used as adsorbents in retentate chromatography. Spots are not as well resolved as by mass spectrometry and resolution at very high and very low molecular masses is limited.

VII. Sequential Extraction of Analytes from a Sample

Analytes can be sequentially extracted from a sample by serially exposing the sample to a selectivity condition followed by collection of the un-retained sample.

A *Hemophilus* knockout mutant lysate was prepared in 10% glycerol 50 mM EDTA. After centrifugation, the supernate was diluted 1:3 in 0.01% Triton X100 in 25 mM HEPES, pH 7.4. An aliquot of 2 μl of the diluted sample was added to a spot of an adsorbent array anionic site. After incubation at room temperature for 30 min, the remaining sample on the anionic site was transferred to a spot of adsorbent array normal phase site. The spot of anionic site was washed with 2 μl of 0.01% Triton X100 25 mM HEPES two times. Each wash was accomplished by pipetting the wash solution in and out of the spot ten times. The washes were combined with the sample initially added on the normal phase spot.

After incubation at room temperature for 30 min, the remaining sample on the normal phase site was transferred to a spot of adsorbent array Ni(II) site. The spot of normal phase site was washed with 2 μl of phosphate buffered saline two times. Each wash was accomplished by pipetting the wash solution in and out of the spot ten times. The washes were combined with the sample initially added on the Ni(II) spot.

After the sample was concentrated to near dryness on the Ni(II) spot, the unbound analytes were recovered by washing with 21 μl of 100 mM imidazole in phosphate buffered saline two times. Each wash was accomplished by pipetting the wash solution in and out of the spot ten times. The washes were transferred to a spot of adsorbent array aliphatic hydrophobic site.

The sample was allowed to concentrate to near dryness on the hydrophobic site, unbound analytes were removed by washing with 2 μl of 5% acetonitrile in 0.1% trifluoroacetic acid two times. Each wash was accomplished by pipeting the wash solution in and out of the spot ten times.

Each spot of anionic, normal phase, Ni(II), and hydrophobic site was washed with 21 μl of water to remove remaining buffer. An aliquot of 0.3 μl of sinapinic acid solution in 50% acetonitrile 0.5% trifluoroacetic acid was added to each spot. The retained analytes on each site was analyzed with laser desorption/ionization time-of-flight mass spectrometer.

FIGS. 19A-19D show the retention map of *Hemophilus* lysate on adsorbent array. Multiple peaks in the mass range 3000 to 25000 Da were observed on the adsorbents. Note that each adsorbent shows different retention for each of the analytes in the sample.

VIII. Progressive Resolution of an Analyte

By adding new binding or elution characteristics to a selectivity condition that resolves an analyte, one can develop a selectivity condition that provides improved resolution of the analyte. In this example, a sample was bound to a Cu(II) adsorbent and exposed to a first eluant and two second eluants. The second eluants differed from the first by the addition of another elution condition. Each added condition improved resolution of the analyte.

*Hemophilus* wild type stationary phase lysate prepared in 10% glycerol was diluted 1:1 in 20 mM sodium phosphate, 0.5 M sodium chloride, pH 7.0. After centrifugation, an aliquot of 150 μl of the supernate was incubated with each spot of adsorbent array Cu(II) site in a bioprocessor. After mixing in the cold for 30 min, the sample was removed. Each spot was washed with a different lysate. A first spot was washed with 150 μl of 20 mM sodium phosphate, 0.5 M sodium chloride, pH 7.0. A second spot was washed with 150 μl of 0.05% Triton X100 in addition to 20 mM sodium phosphate, 0.15 M NaCl, pH 7.0. A third spot was washed with 150 μl of 100 mM imidazole in addition to 20 mM sodium phosphate, 0.15 M NaCl, pH 7.0. Each wash was accomplished by incubating the wash solution with the spot for 5 min with mixing. The wash was repeated two times. Each spot was washed with water to remove detergent and buffer.

The adsorbent array was removed from the bioprocessor. An aliquot of 0.3 μl of sinapinic acid solution in 50% acetonitrile 0.5% trifluoroacetic acid was added to each spot. The retained analytes on each spot was analyzed with laser desorption/ionization time-of-flight mass spectrometer.

FIGS. 20A-20C show the retention map of *Hemophilus* lysate on adsorbent array Cu(II) site after washing under the three elution conditions described above. Multiple peaks in the mass range 2000 to 18000 Da were observed. The protein marked with a "*" was only a minor component in the retention map of FIG. 20A. When the selectivity condition was modified by the addition of a detergent, Triton X100 (FIG. 20B), to the same buffer, the same protein "*" was retained better than the other analytes and resolved better. When the selectivity condition was modified by the addition of an affinity displacer, imidazole, to the same buffer (FIG. 20C.), the protein "*" was highly resolved from the other analytes in the retentate map.

This strategy of progressive identification of selectivity conditions with improved resolution for an analyte can be adopted to develop a method for the preparative purification of this protein from the total *Hemophilus* lysate.

IX. Differential Expression of an Analyte: Marker Protein Discovery.

A. Human Serum

An aliquot of 0.5 μl of normal or diseased human sera was diluted with an equal volume of 20 mM sodium phosphate, 0.5 M NaCl, pH 7.0. Each was applied to a different spot on an adsorbent array Cu(II) site. After incubation at 4° C. for 1 h, each spot was washed with 2 μl of 20 mM sodium phosphate, 0.5 M NaCl, pH 7.0, two times. Each wash was accomplished by pipeting the wash solution in and out of the spot ten times. Each spot was finally washed with 2 µl of water to remove remaining buffer. An aliquot of 0.3 µl of sinapinic acid solution in 50% acetonitrile 0.5% trifluoroacetic acid was added to each spot. The retained analytes on each spot was analyzed with laser desorption/ionization time-of-flight mass spectrometer.

Figures 21A, 21B, 21C, 21D:
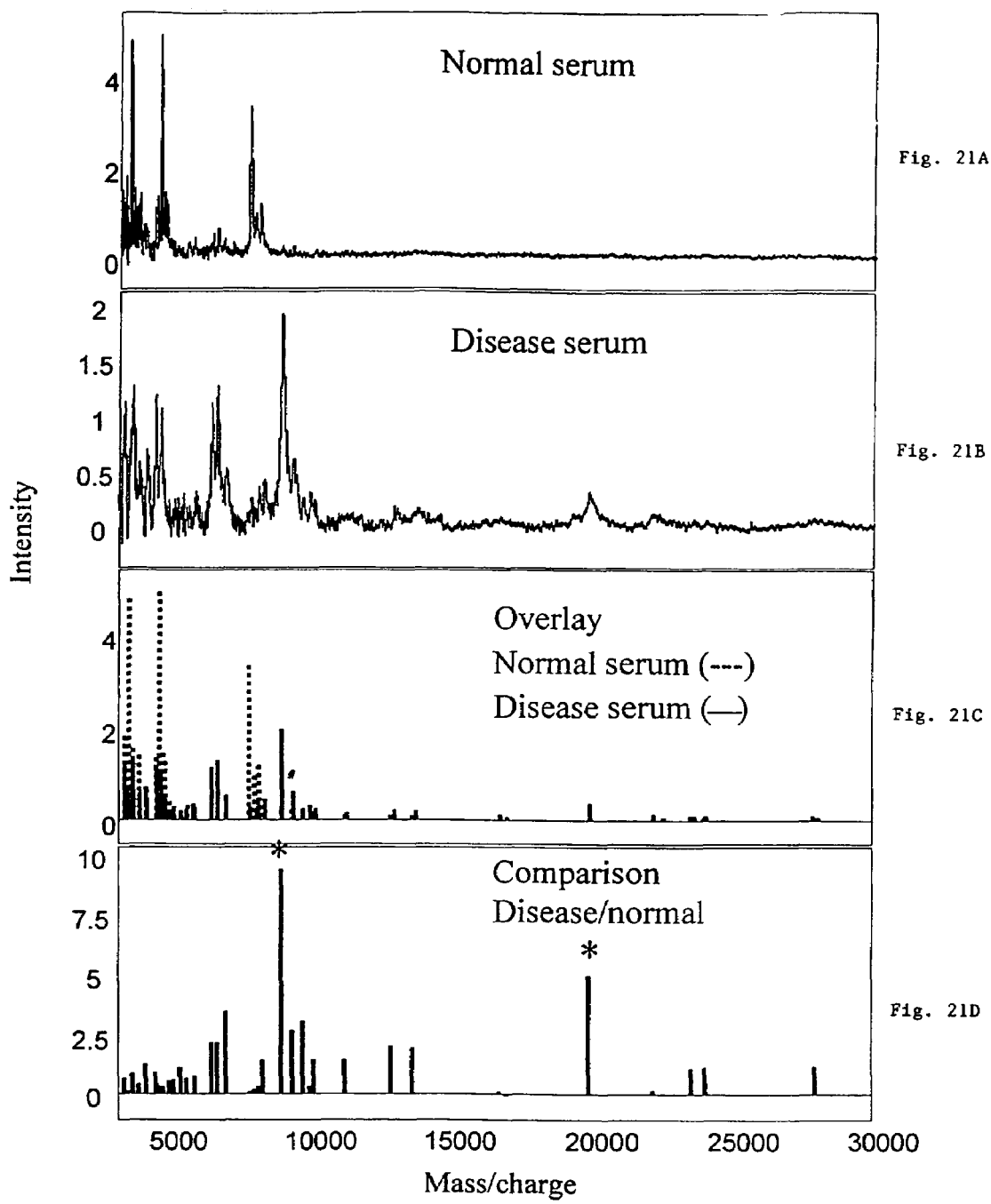
FIGS. 21A-21D show the results of a comparison between components in normal human serum and diseased serum.
Figures 22, 22A, 22B, 22C, 22D:
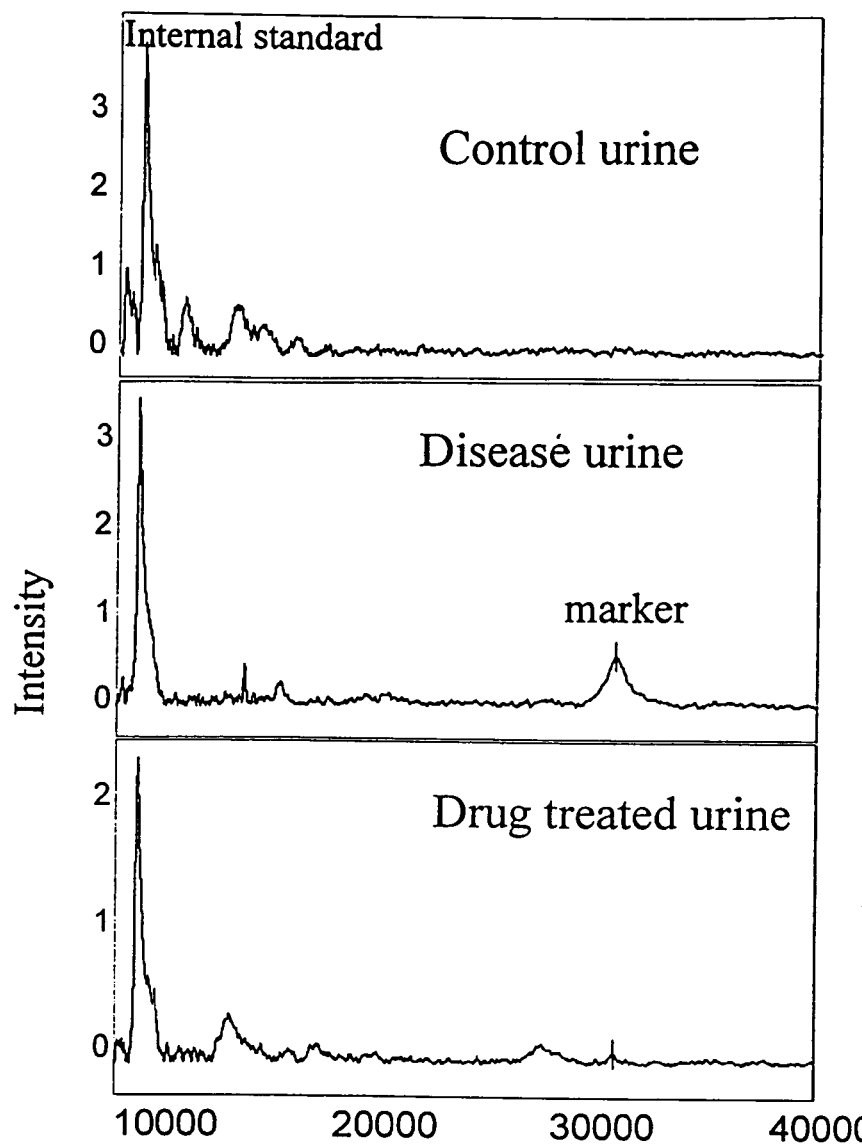
FIGS. 22A-22D show a comparison of retentate maps for control, diseased and drug-treated mouse urine on a Cu(II) adsorbent, and quantitation of amount of a marker in diseased and drug-treated urine.

Proteins marked with a "*" in FIG. 21D are present in significantly greater amounts in diseased serum than in normal serum. The results illustrate a method for discovery of disease markers that can be used in clinical diagnostics.

B. Mouse Urine

An aliquot of 11 µl of normal, diseased or drug treated mouse urine was applied to a different spot of an adsorbent array Cu(II) site. After incubation at room temperature for 10 min, each spot was washed with 2 µl of 100 mM imidazole in 20 mM sodium phosphate, 0.15 M NaCl, pH 7.0, two times. Each wash was accomplished by pipeting the wash solution in and out of the spot ten times. Each spot was finally washed with 2 µl of water to remove remaining buffer. An aliquot of 0.3 µl of sinapinic acid solution in 50% acetonitrile 0.5% trifluoroacetic acid was added to each spot. The retained analytes on each spot was analyzed with laser desorption/ionization time-of-flight mass spectrometer.

The retentate maps of normal (control), diseased and drug treated mouse urine are shown in the FIG. 1. One analyte was found to be present in much higher quantity in the disease mouse urine (middle panel), the same analyte was not found in normal mouse urine (upper panel), and found in drug treated mouse urine in much reduced quantity (lower panel). This analyte can be used as a potential disease marker. To illustrate the feasibility of a quantitative diagnostic assay, the area under the peak of the retained marker protein are calculated and shown in the table. A clear quantitative difference is observed between the disease and drug treated mouse urines. To compensate for experimental variability, an internal standard analyte was used. The normalized disease marker peak area (i.e., peak area of marker divided by peak area of internal standard) for each urine sample is presented in the bottom panel. There is at least a ten fold reduction of the disease urine marker after drug treatment.

C. Human Urine

Urines from normal human and cancer patients were diluted 1:2 in 0.01% Triton X100 in phosphate buffered saline. An aliquot of 1.5 µl of normal or disease human urine was applied to a different spot of an adsorbent array aliphatic hydrophobic site prewetted with 0.5 µl of isopropanol/acetonitrile (1:2) 0.1% trifluoroacetic acid. After incubation at 4 C for 30 min, each spot was washed with 2 µl of 50% ethylene glycol in 10 mM Tris HCl, 0.05 M NaCl, pH 7.5, two times. Each wash was accomplished by pipeting the wash solution in and out of the spot ten times. Each spot was finally washed with 2 µl of water to remove remaining ethylene glycol and buffer. An aliquot of 0.3 µl of sinapinic acid solution in 50% acetonitrile 0.5% trifluoroacetic acid was added to each spot. The retained analytes on each spot was analyzed with laser desorption/ionization time-of-flight mass spectrometer.

Figure 23:
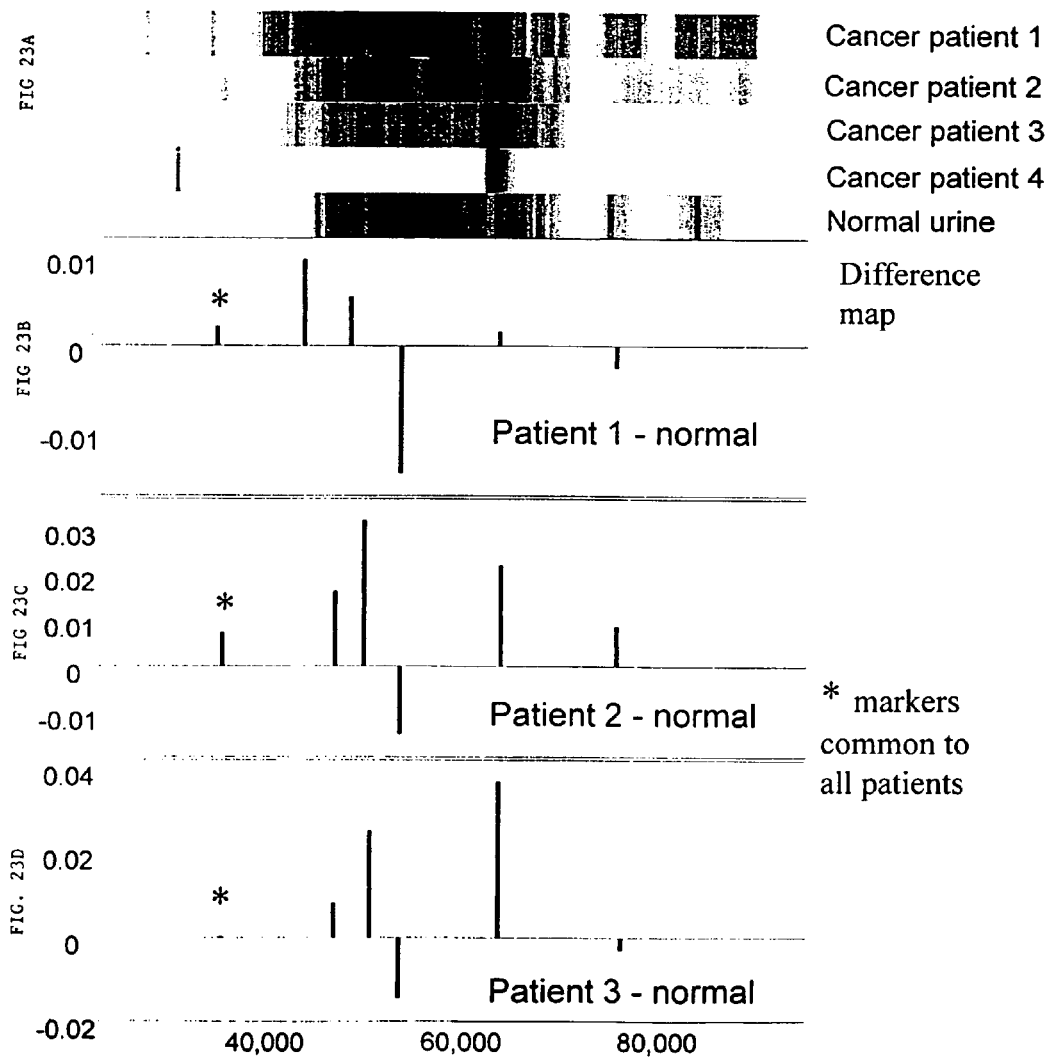
FIGS. 23A-23D show retentate maps of analytes in urine from four human cancer patients shown in "gel view" format. Difference maps between patients 1, 2 and 3 show two common analytes that are present in increased amounts in these patients.

The retentate maps of urines of four cancer patients and a normal human are shown FIG. 23A. Multiple protein peaks were retained on the adsorbent array hydrophobic site after washing with 50% ethylene glycol in Tris/NaCl buffer. To identify possible disease markers, difference maps between individual patient urine and normal urine are plotted. Each bar in the difference plot above the baseline represents an analyte present in higher quantity in the patient urine. (FIG. 23B-23D.) Variations in the patterns of difference map of the patients reflect individual fluctuations in a population. However, one analyte around 5000 Da (marked with *) and a cluster of analytes around 7500 Da (marked with *), are found to be consistently present in higher quantities in all patients, therefore these can be identified as potential disease markers.

X. Capture of Phage from Phage Display Library

Viruses adsorbed to the surface of a protein chip can be detected by desorption spectrometry. Antibodies against viral coat proteins, used as adsorbents, can capture viruses. A target protein used as an adsorbent can capture phage displaying a single-chain antibody against the target.

A. Detection Sensitivity of Phage Display Antibody by Adsorbent Substrate

M13 phage ($10^{12}$ particle/ml) in growth medium was serially diluted into 0.01% Triton X100 in 25 mM HEPES, pH 7.4. An aliquot of 0.25 µl of each of the diluted phage suspension was added to a spot of an adsorbent array aliphatic hydrophobic site. An aliquot of 0.3 µl of CHCA in 50% acetonitrile, 0.5% trifluoroacetic acid was added. The samples were analyzed by laser desorption/ionization time-of-flight mass spectrometer.

The M13 phage Gene VIII protein was detected with high sensitivity on the array. FIGS. 24A-24E. A detectable signal (signal/noise>2) was obtained when the phage suspension was diluted 10,000,000 times.

B. Identification of M13 Phage by Adsorbent Array

Rabbit anti-M13 antibody (Strategene) was immobilized on Protein A Hyper D (BioSepra), and washed with phosphate buffered saline, pH 7 extensively. An aliquot of 1-10 µl suspension of M13 phage ($10^{12}$ particle/ml) in growth medium was incubated with 1 µl aliquot of immobilized anti-M13 antibody at 4° C. overnight. After washing with 0.05% Tween 20 in phosphate buffered saline, pH 7 and then with water to remove detergent and buffer, an aliquot of the captured phage was analyzed with laser desorption/ionization time-of-flight mass spectrometer in the presence of sinapinic acid.

Figures 25A, 25B:
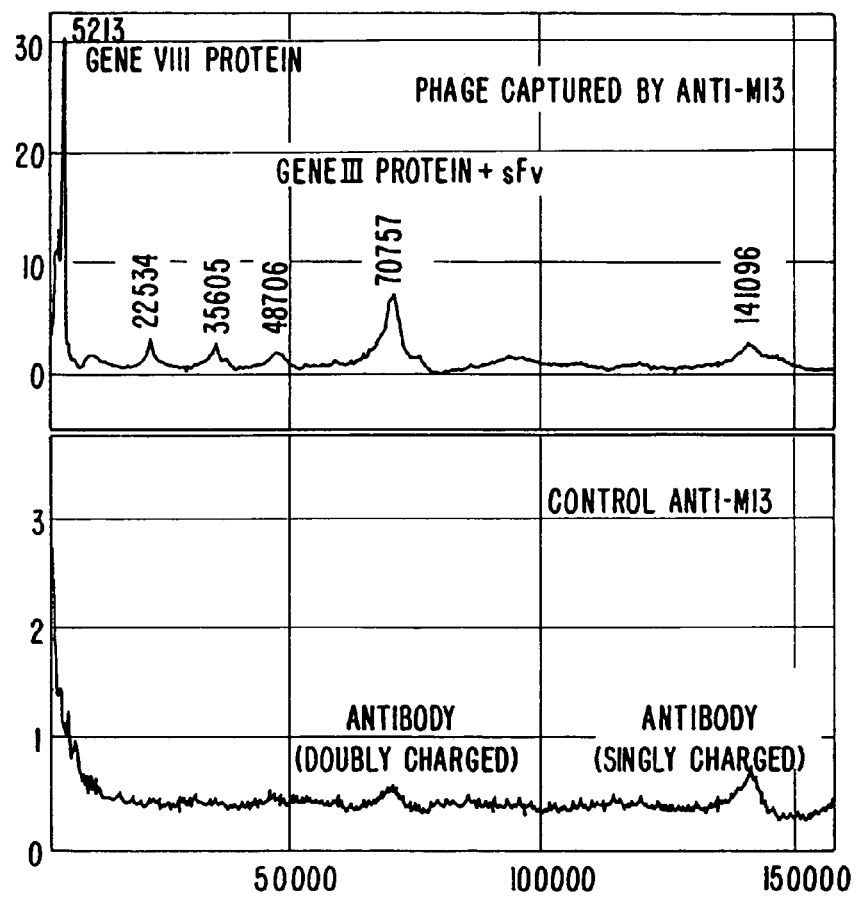
FIGS. 25A-25B show the capture of M13 by desorption spectrometry using anti-M13 antibody as an adsorbent.

The anti-M13 antibody control shows only the antibody signal (singly and doubly charged). FIG. 25A. When the M13 phage was captured by the antibody, the most easily identifiable protein peaks from the phage are the Gene VIII protein and the Gene III protein fusion with single chain antibody. FIG. 25B. Since the M13 phage Gene VIII protein is detected with high efficiency by the method, it can be used as a sensitive monitor of phage capture.

C. Specific Capture of M13 Phage Displaying Single Chain Antibody

HIV-1 Tat protein (McKesson BioServices) was coupled to a preactivated substrate. After blocking with ethanolamine, the array was washed with 0.005% Tween20 in phosphate buffered saline, pH 7, and then 0.1% BSA in phosphate buffered saline, pH 7. A serial dilution of M13 phage displaying single chain antibody against the Tat protein was incubated with the Tat protein adsorbent array at 4° C. overnight. A negative control of a serial dilution of M13 phage not displaying the single chain antibody against the Tat protein was also incubated with the Tat protein adsorbent array the same way. The arrays were washed with 0.05% Tween20 in phosphate buffered saline, followed by 1 M urea in phosphate buffered saline, pH 7.0 and finally with water to remove buffer and urea. An aliquot of 0.3 µl of CHCA in 50% acetonitrile 0.5% trifluoroacetic acid was added. The retained phage was analyzed by laser desorption/ionization time-of-flight mass spectrometer.

A specific binding of M13 phage displaying single chain antibody against Tat protein was observed in a concentration dependent manner (solid line). FIGS. 26A-26D. Nonspecific binding by a nonspecific M13 phage was minimal on the adsorbent array (dashed line). These results illustrate a very sensitive method of detecting a phage containing a gene that encodes a single chain antibody specifically recognizing a target analyte.

XI. Screening to Determine Whether a Compound Inhibits Binding Between Receptor and Ligand The methods of this invention can be used to determine whether a test agent modulates the binding of a ligand for a receptor. In this example, we show that retentate chromatography can detect the inhibition of binding between TGF-β and bound TGF-β receptor used as an adsorbent by free TGF-β receptor.

TGF-β recombinant receptor-Fc fusion protein (R&D, Minnesota) was specifically bound on a Protein G adsorbent array. TGF-β (R&D, Minnesota) was serially diluted into cell conditioned medium (2.5× concentrated) and incubated with the receptor-Fc Protein G adsorbent array at 4° C. overnight. Another set of serially diluted TGF-β in cell conditioned medium was incubated with the receptor-Fc Protein G adsorbent array in the presence of a modulating agent. In this illustration, the modulating agent was the free TGF-β receptor. After incubation under the same conditions, the chips were washed with 0.05% Triton X100 in PBS and then 3M urea in PBS. An aliquot of 0.3 µl of sinapinic acid was added to each spot and analyzed by laser desorption/ionization time-of-flight mass spectrometry.

Figure 27A:
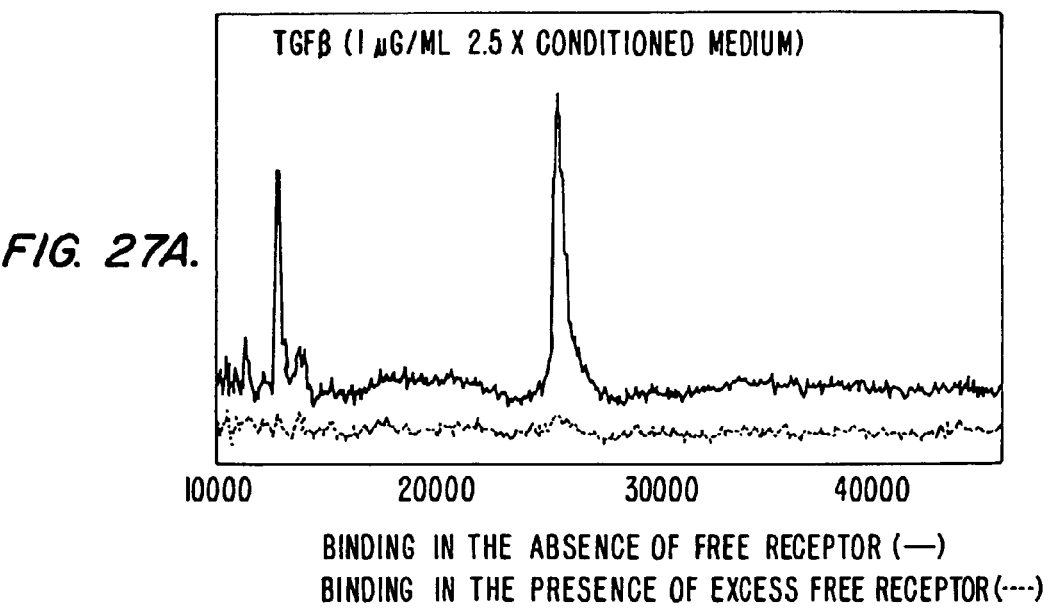
FIGS. 27A-27B show retention maps of TGF-β binding to docked TGF-β receptor fusion protein at 1 µg/ml (FIG. 27A) and at 100 ng/ml (FIG. 27B). The solid line shows binding without the presence of free TGF-β receptor. The dashed line shows binding in the presence TGF-β receptor.
Figure 27B:
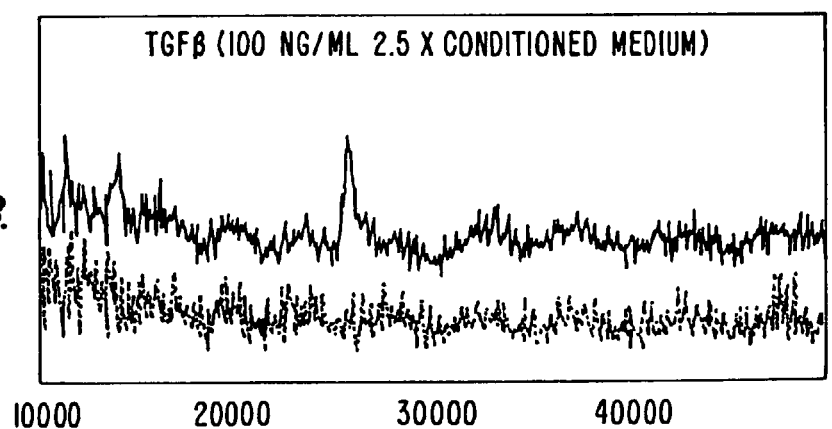
Figure 28A:
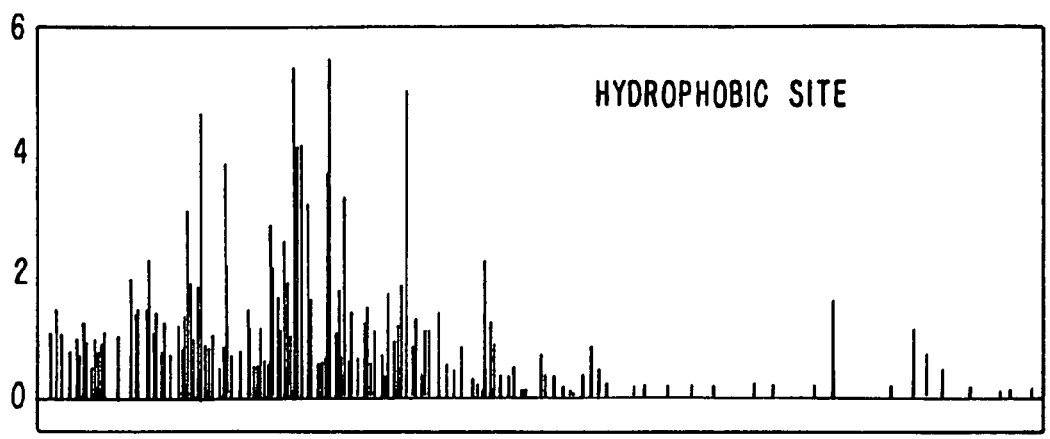
FIGS. 28A-28C show resolution of proteins from *Hemophilus* lysate using hydrophobic, cationic and Cu(II) adsorbents at molecular masses from 0 kD to 30 kD. Each retained analyte is represented by a bar, the height of the bar represents the intensity of the retained analyte.
Figure 28B:
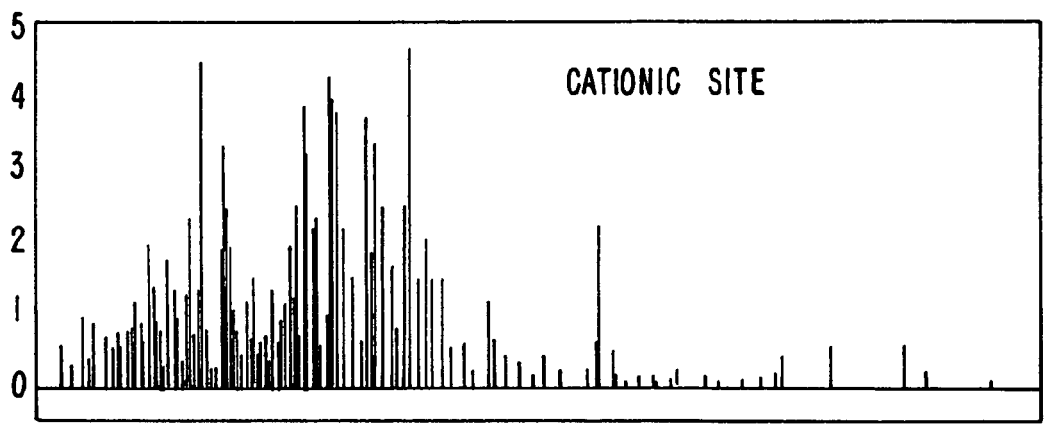
Figure 28C:
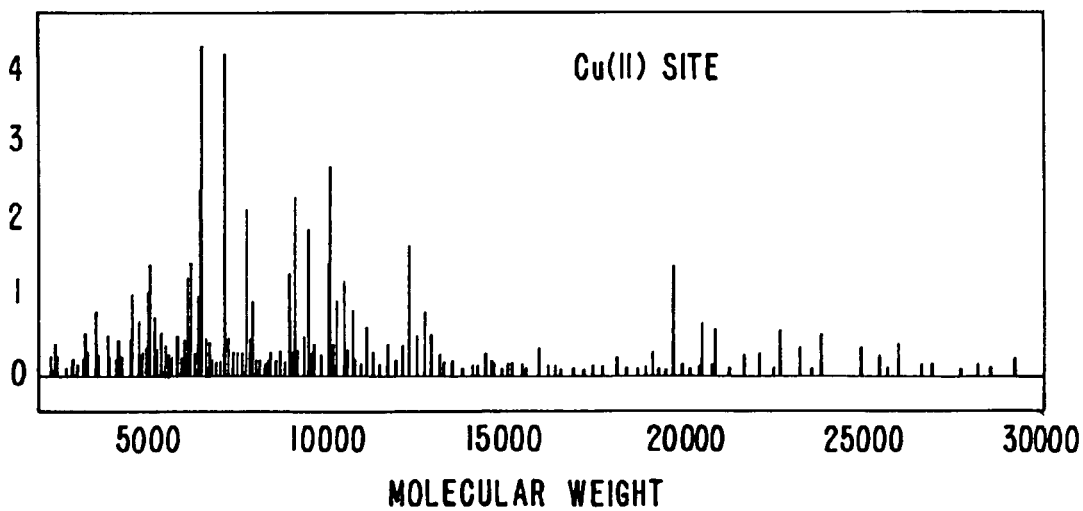
Figure 29A:
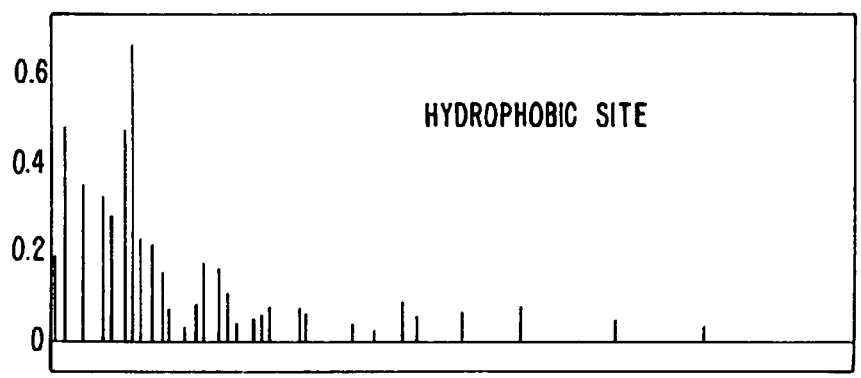
FIGS. 29A-29C show resolution of proteins from *Hemophilus* lysate using hydrophobic, cationic and Cu(II) adsorbents at molecular masses from about 30 kD to about 100 kD.
Figure 29B:
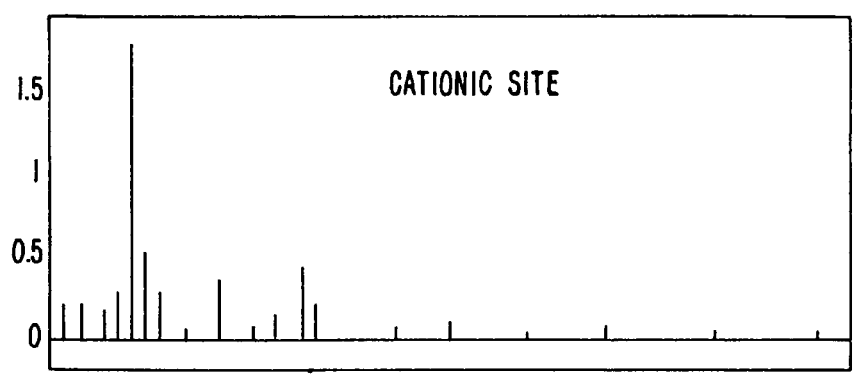
Figure 29C:
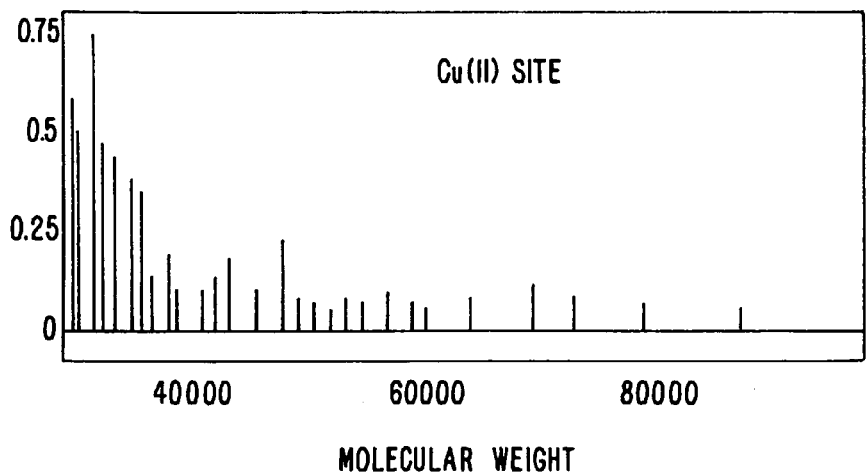
Figure 30:
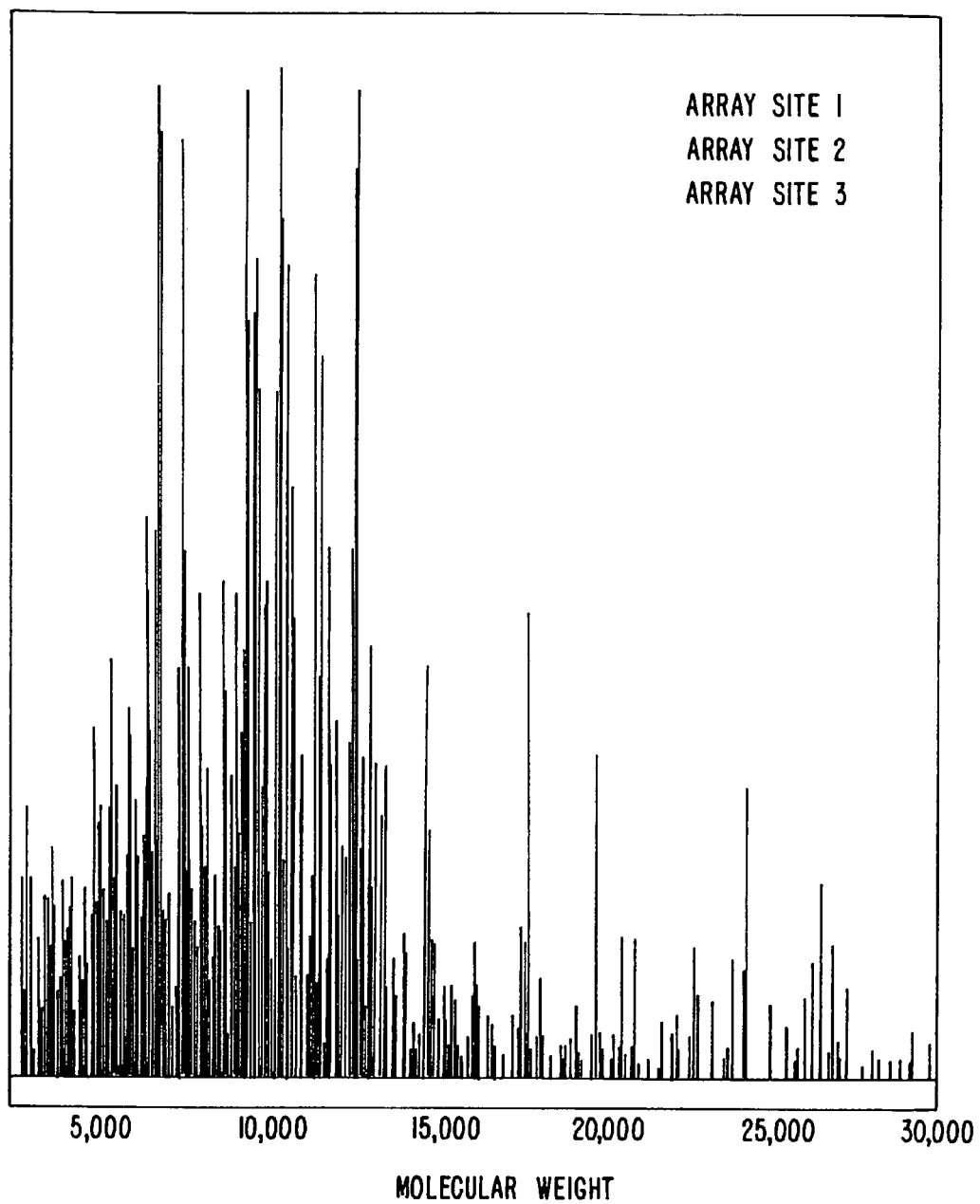
Figure 31:
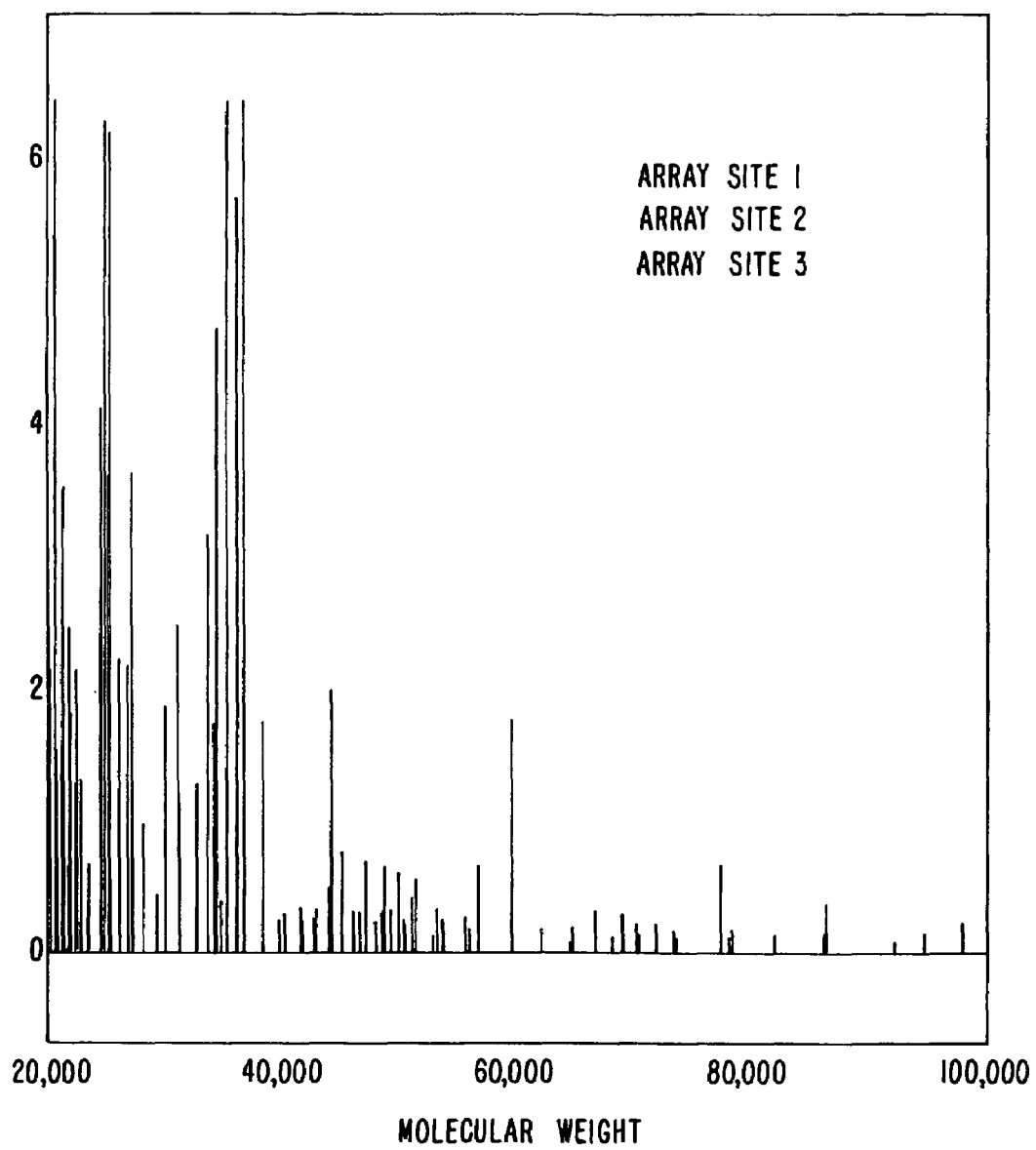

FIG. 27A shows the specific binding of 1 µg/ml TGF-β to the receptor-Fc Protein G adsorbent array (solid line). Little or no proteins in the cell conditioned medium were found to bind. FIG. 27B shows the specific binding of 100 ng/ml of TGF-β to the receptor-Fc Protein G adsorbent array (solid line). When the incubation of TGF-β and the receptor-Fc Protein G adsorbent array was performed in the presence of a modulating agent (free TGF-β receptor), the binding was completely eliminated when there was 100 ng/ml of TGF-β (FIG. 27A, dashed line) and only a trace of binding where there was 1 µg/ml of TGF-β (FIG. 27B, dashed line). In this illustration, the modulating agent (the same receptor) has high specific binding affinity for the ligand, thus offering a very effective competition of the target analyte binding event. In the other cases, the ratio of the target analyte bound to the adsorbent in the present and absence of the modulating agent gives an indication of the efficacy of the modulating agent.

XII. Resolving Power of Retentate Chromatography

This example demonstrates the ability of retentate chromatography, with its parallel processing of a sample under different selectivity conditions, to resolve proteins in a sample.

*Hemophilus influenzae* lysate was prepared in 10% glycerol. After centrifugation, the supernate was diluted 1:3 in 0.01% Triton X100 in 25 mM HEPES, pH 7.4. An aliquot of 2 µl of the diluted sample was added to a spot of adsorbent array cationic site. After incubation at room temperature for 30 min, the spot was washed with 25 mM HEPES, pH 7.4. A second aliquot of 2 µl of the dilute sample as added to a spot of adsorbent array aliphatic hydrophobic site. After incubation at room temperature for 30 min, the spot was washed with water. A third aliquot of 2 µl of the diluted sample was added to a spot of adsorbent array Cu(II) site. After incubation at room temperature for 30 min, the spot was washed with 0.05% Triton X100 in phosphate buffered saline, pH 7.4. An aliquot of 0.3 of sinapinic acid solution in 50% acetonitrile 0.5% trifluoroacetic acid was added to each spot. The retained analytes on each site was analyzed with laser desorption/ionization time-of-flight mass spectrometer.

Results are shown in FIGS. 28-31. The total retained analyte count was around 550. The result illustrates a method for combinatorial separation, including separation and detection of multiple analytes in parallel.

XIII. Sequential Assembly of Multimeric Structures

This example illustrates a method of building a secondary adsorbent on a primary adsorbent. The secondary adsorbent then acts as a specific adsorbent for a target analyte.

Figure 32:
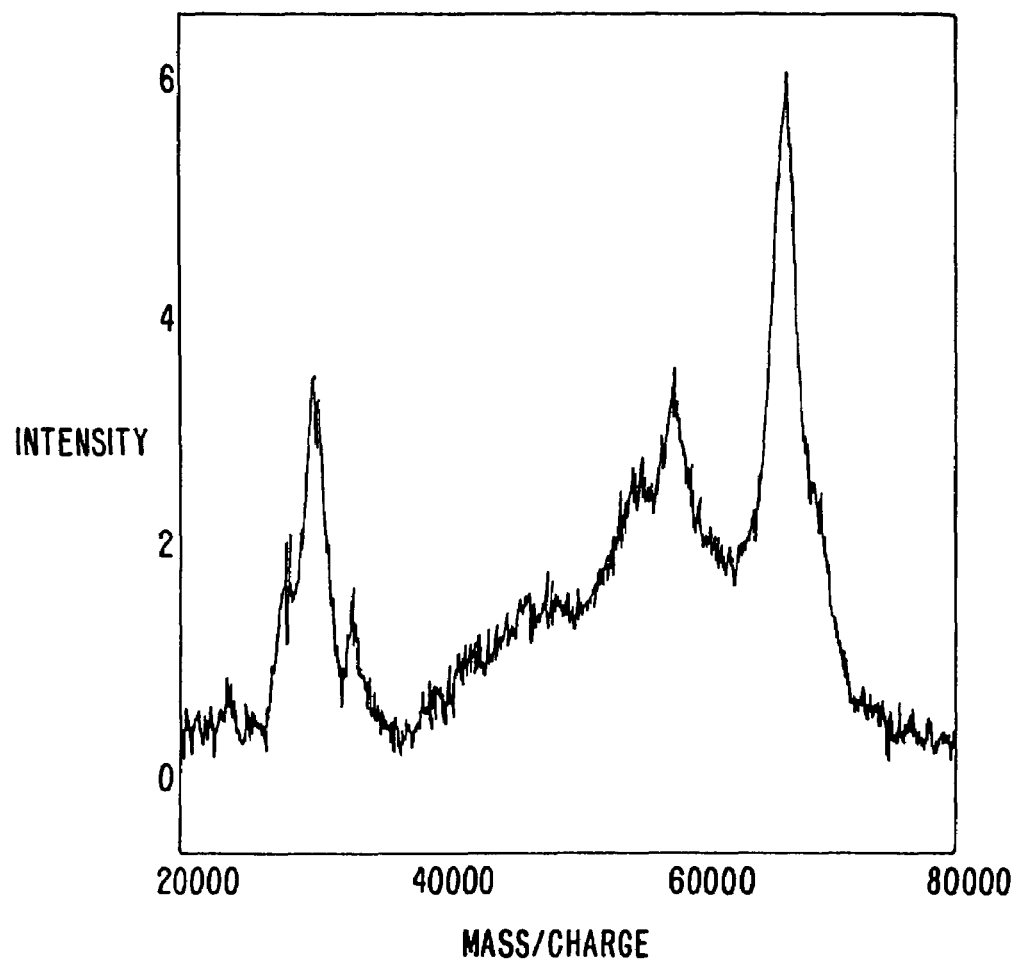
FIG. 32 shows the binding of GST fusion protein to a normal adsorbent.

An aliquot of 0.5 µl of GST fusion receptor diluted in 20 mM Tris 100 mM, sodium chloride. 0.4% NP40, pH 7.2, was added to a spot of an adsorbent array normal site. The solution was allowed to concentrate on the spot until almost dryness. The spot was washed with 2 µl of 10 mM Tris, 50 mM sodium chloride, pH 7.2, three times. Each wash was accomplished by pipeting the wash solution in and out of the spot five times. The spot was finally washed with 2 µl of water two times to remove remaining buffer. An aliquot of 0.3 µl of sinapinic acid solution in 50% acetonitrile, 0.5% trifluoroacetic acid was added to the spot. The retained GST fusion receptor was analyzed with laser desorption/ionization time-of-flight mass spectrometer. (FIG. 32.) An aliquot of 0.5 µl of GST fusion receptor in 20 mM Tris, 100 mM sodium chloride, 0.4% NP40, pH 7.2, was added to a spot of an adsorbent array normal site. A sample containing only GST protein (with no receptor) was applied to another spot as a negative control. The solution was allowed to concentrate on the spot until almost dryness. 0.5 µl of 10 mM Tris, 50 mM sodium chloride, pH 7.2, was added to each spot. The solution was removed using a pipet after 10 seconds of standing at room temperature.

An aliquot of 1 µl of a solution containing one specific ligand in a library of 96 other ligands was immediately added to each spot. The adsorbent array was incubated in a moist chamber at room temperature for 1 hour. Each spot was washed with 2 µl of 30% isopropanol:acetonitrile (1:2) in water, two times. Each wash was accomplished by pipeting the wash solution in and out of the spot ten times. An aliquot of 0.3 µl of α-cyano-4-hydroxycinnamic acid solution in 50% acetonitrile, 0.5% trifluoroacetic acid was added to the spot. The captured ligand on the receptor was analyzed with laser desorption/ionization time-of-flight mass spectrometer.

FIG. 33A shows the binding of a specific ligand out of a library of 96 other ligands to the GST fusion receptor which is captured on an adsorbent array normal site. FIG. 33B shows that there is no binding of the ligand to GST protein alone (with no receptor) captured on the same array, which serves as a negative control of the experiment.

The present invention provides novel materials and methods for retentate chromatography. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

The invention claimed is:

1. A method for preparing a substrate for detecting at least one analyte in a sample comprising the steps of:
    a) exposing the sample to at least two different selectivity conditions, each selectivity condition defined by the combination of an adsorbent and an eluant, to allow retention of the analyte by the adsorbent;
    b) identifying by desorption spectrometry at least one selectivity condition under which the analyte is retained; and
    c) immobilizing at least one adsorbent of an identified selectivity condition on the substrate, whereby the substrate for detecting at least one analyte is prepared.

2. The method of claim 1 wherein the step of identifying comprises identifying at least one selectivity condition under which a plurality of analytes are retained.

3. The method of claim 1 wherein the step of immobilizing comprises immobilizing on the substrate a plurality of adsorbents that retain the analyte under an elution condition as a multiplex adsorbent.

4. The method of claim 1, comprising exposing the sample to at least sixteen different selectivity conditions.

5. The method of claim 1, wherein the at least two different selectivity conditions comprise at least two different adsorbents.

6. The method of claim 1, wherein the at least one adsorbent has a basis of attraction selected from the group consisting of a hydrophobic interaction; a hydrophilic interaction; an anionic interaction; a cationic interaction, a coordinate covalent interaction, a thiophilic interaction, a biospecific interaction and a glycoprotein interaction adsorbent.

7. The method of claim 1, wherein at least two different adsorbents are immobilized on the substrate.

8. The method of claim 1, wherein the eluant in the different selectivity conditions is the same.

9. The method of claim 1, wherein the eluant is selected from the group consisting of a pH-based eluant, an ionic-strength-based eluant, a water structure-based eluant, a detergent-based eluant and a hydrophobicity-based eluant.

10. The method of claim 1, wherein the substrate is a mass spectrometry probe.

11. The method of claim 1, wherein the substrate is a bead that is positioned on a mass spectrometry probe.

12. The method of claim 1, wherein the at least one adsorbent is immobilized on the substrate in predetermined addressable locations.

13. The method of claim 1, wherein the substrate is comprised of a material selected from the group consisting of glass, ceramic, electrically conducting polymers, TEFLON® (polytetrafluoroethylene) coated materials, organic polymers, biopolymers, metals, films; beads of cross-linked polymers, and combinations thereof.

14. The method of claim 1, wherein the substrate is in the form of a strip or plate.

15. The method of claim 1, wherein the substrate is removably insertable into a mass spectrometry probe.

16. The method of claim 1, wherein the adsorbent is immobilized on the substrate through covalent bonding.

17. The method of claim 1, wherein the adsorbent is immobilized on the substrate through non-covalent bonding.

18. The method of claim 1, wherein the adsorbent is immobilized on a bifunctional linker that is immobilized on the substrate.

19. The method of claim 18, wherein the bifunctional linker is immobilized on the substrate through an inorganic oxide or a sulfhydryl functional group.

20. The method of claim 18, wherein the bifunctional linker is a residue of aminopropyl triethoxysilane or aminoethyl disulfide.

21. The method of claim 18, wherein the bifunctional linker is a residue of carbodiimide or N-hydroxysuccinimide.

22. The method of claim 1, wherein the adsorbent is immobilized on a cross-linked polymer that is immobilized on the substrate.

23. The method of claim 22, wherein the cross-linked polymer is selected from the group consisting of cellulose, dextran, carboxymethyl dextran, polyacrylamide and mixtures thereof.

* * * * *